United States Patent
Crew et al.

(10) Patent No.: US 12,208,095 B2
(45) Date of Patent: Jan. 28, 2025

(54) METHODS OF TREATING BREAST CANCER WITH TETRAHYDRONAPHTHALENE DERIVATIVES AS ESTROGEN RECEPTOR DEGRADERS

(71) Applicant: Arvinas Operations, Inc., New Haven, CT (US)

(72) Inventors: Andrew P. Crew, Guilford, CT (US); John Flanagan, Belmont, MA (US); Sheryl Maxine Gough, Stratford, CT (US); Royal J. Haskell, III, Durham, CT (US); Marcia Dougan Moore, Suffield, CT (US); Yimin Qian, Plainsboro, NJ (US); Ian Charles Anthony Taylor, Madison, CT (US); Jing Wang, Milford, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 17/001,519

(22) Filed: Aug. 24, 2020

(65) Prior Publication Data
US 2021/0060008 A1    Mar. 4, 2021

Related U.S. Application Data

(60) Provisional application No. 63/023,067, filed on May 11, 2020, provisional application No. 62/942,663, (Continued)

(51) Int. Cl.
*A61K 31/496*    (2006.01)
*A61K 31/519*    (2006.01)
(Continued)

(52) U.S. Cl.
CPC .......... *A61K 31/496* (2013.01); *A61K 31/519* (2013.01); *A61K 47/02* (2013.01); (Continued)

(58) Field of Classification Search
CPC .............. A61K 31/454; A61K 31/4545; A61K 31/496; A61P 35/00
See application file for complete search history.

(56) References Cited

U.S. PATENT DOCUMENTS 5,492,922 A    2/1996 Palkowitz et al.
5,665,772 A    9/1997 Cottens et al.
(Continued)

FOREIGN PATENT DOCUMENTS

CA    2274381 A1    12/1999
CN    1844118 A    10/2006
(Continued)

OTHER PUBLICATIONS

Beaver (Clinical Cancer Research vol. 21 pp. 4760-4766 published 2015) (Year: 2015).*
(Continued)

*Primary Examiner* — Theodore R. Howell
*Assistant Examiner* — George W Kosturko
(74) *Attorney, Agent, or Firm* — COOLEY LLP

(57) ABSTRACT

The present application relates to treating and/or preventing breast cancer, including locally advanced or metastatic, ER+, HER2– breast cancer, in a subject in need of treatment, comprising administering a compound of Formula (I), (Continued)

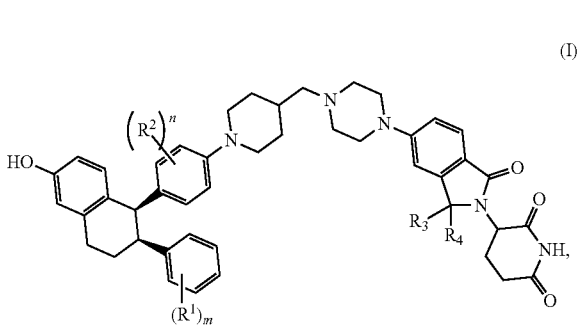

or a pharmaceutically acceptable salt, enantiomer, stereoisomer, solvate, polymorph, isotopic derivative, or prodrug thereof, wherein $R^1$, $R^2$, $R_3$, $R_4$, m, and n are defined herein.

31 Claims, 15 Drawing Sheets

Related U.S. Application Data filed on Dec. 2, 2019, provisional application No. 62/924,653, filed on Oct. 22, 2019, provisional application No. 62/891,648, filed on Aug. 26, 2019.

(51) Int. Cl.
*A61K 47/02* (2006.01)
*A61K 47/22* (2006.01)
*A61K 47/26* (2006.01)
*A61K 47/38* (2006.01)
*A61P 35/00* (2006.01)

(52) U.S. Cl.
CPC .............. *A61K 47/22* (2013.01); *A61K 47/26* (2013.01); *A61K 47/38* (2013.01); *A61P 35/00* (2018.01)

(56) References Cited

U.S. PATENT DOCUMENTS

| | | | |
|---|---|---|---|
| 5,681,835 A | 10/1997 | Willson | |
| 5,877,219 A | 3/1999 | Willson | |
| 5,916,916 A | 6/1999 | Hauser et al. | |
| 5,985,890 A | 11/1999 | Cottens et al. | |
| 6,200,985 B1 | 3/2001 | Cottens et al. | |
| 6,207,716 B1 | 3/2001 | Willson | |
| 6,306,663 B1 | 10/2001 | Kenten et al. | |
| 6,440,990 B1 | 8/2002 | Cottens et al. | |
| 6,670,348 B1 | 12/2003 | Rosen et al. | |
| 7,030,141 B2 | 4/2006 | Bigge et al. | |
| 7,041,298 B2 | 5/2006 | Deshaies et al. | |
| 7,208,157 B2 | 4/2007 | Sakamoto et al. | |
| 7,244,851 B2 | 7/2007 | Cohen et al. | |
| 7,345,081 B2 | 3/2008 | Cohen et al. | |
| 7,419,975 B2 | 9/2008 | Palermo et al. | |
| 7,517,906 B2 | 4/2009 | Condon et al. | |
| 7,915,293 B2 | 3/2011 | Ramesh | |
| 8,012,997 B2 | 9/2011 | Robarge et al. | |
| 8,101,623 B2 | 1/2012 | Luke et al. | |
| 8,227,462 B2 | 7/2012 | Fairhurst et al. | |
| 8,362,065 B2 | 1/2013 | Liu et al. | |
| 8,410,158 B2 | 4/2013 | Seefeld et al. | |
| 8,476,268 B2 | 7/2013 | Fairhurst et al. | |
| 8,481,568 B2 | 7/2013 | Muller et al. | |
| 8,946,278 B2 | 2/2015 | Seefeld et al. | |
| 9,163,007 B2 | 10/2015 | Akritopoulou-Zanze et al. | |
| 9,500,653 B2 | 11/2016 | Crews et al. | |
| 9,632,089 B2 | 4/2017 | Crews et al. | |
| 9,650,393 B2 | 5/2017 | Braun et al. | |
| 9,655,857 B2 | 5/2017 | Chong et al. | |
| 9,796,698 B2 | 10/2017 | Muller et al. | |
| 9,801,868 B2 | 10/2017 | Muller et al. | |
| 9,867,801 B2 | 1/2018 | Srinivasan et al. | |
| 10,047,151 B2 | 8/2018 | Lopez-Girona et al. | |
| 10,059,714 B2 | 8/2018 | Johnson et al. | |
| 10,112,932 B2 | 10/2018 | Braun et al. | |
| 10,647,698 B2 | 5/2020 | Crew et al. | |
| 10,654,855 B2 | 5/2020 | Johnson et al. | |
| 10,766,884 B2 | 9/2020 | Chen et al. | |
| 10,781,219 B2 | 9/2020 | Gosselin et al. | |
| 10,851,091 B2 | 12/2020 | Braun et al. | |
| 10,899,742 B1* | 1/2021 | Crew | A61K 31/551 |
| 10,940,135 B2 | 3/2021 | Wan et al. | |
| 11,028,100 B2 | 6/2021 | Chakravarty et al. | |
| 11,104,666 B2 | 8/2021 | Crew et al. | |
| 11,220,494 B2 | 1/2022 | Chen et al. | |
| 11,236,095 B2 | 2/2022 | Johnson et al. | |
| 11,261,178 B2 | 3/2022 | Fan et al. | |
| 11,597,720 B2 | 3/2023 | Qian et al. | |
| 2006/0128632 A1 | 6/2006 | Sharma et al. | |
| 2007/0218138 A1* | 9/2007 | Bittorf | A61K 9/146 |
| | | | 514/6.9 |
| 2008/0051432 A1 | 2/2008 | Zhang | |
| 2008/0098104 A1 | 4/2008 | Kong | |
| 2008/0214501 A1 | 9/2008 | Pan et al. | |
| 2008/0269140 A1 | 10/2008 | Wang et al. | |
| 2009/0047563 A1 | 2/2009 | Hase et al. | |
| 2010/0203012 A1 | 8/2010 | Laurent et al. | |
| 2010/0240748 A1 | 9/2010 | Stock et al. | |
| 2011/0195043 A1 | 8/2011 | Sun et al. | |
| 2011/0230457 A1 | 9/2011 | Berghausen et al. | |
| 2012/0270800 A1 | 10/2012 | Verdine et al. | |
| 2013/0029993 A1 | 1/2013 | Stadtmueller | |
| 2014/0235629 A1 | 8/2014 | Bartberger et al. | |
| 2014/0243372 A1 | 8/2014 | Rew | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0141470 A1 | 5/2015 | Garraway et al. | |
| 2015/0258080 A1 | 9/2015 | Hager et al. | |
| 2015/0291562 A1 | 10/2015 | Crew et al. | |
| 2015/0344473 A1 | 10/2015 | Du et al. | |
| 2016/0022642 A1 | 1/2016 | Crews et al. | |
| 2016/0045607 A1 | 2/2016 | Crew et al. | |
| 2016/0058872 A1 | 3/2016 | Crew et al. | |
| 2016/0136230 A1 | 5/2016 | Campos et al. | |
| 2016/0214972 A1 | 7/2016 | Jin et al. | |
| 2016/0243247 A1 | 8/2016 | Bradner et al. | |
| 2016/0272639 A1 | 9/2016 | Crew et al. | |
| 2016/0368911 A1 | 12/2016 | Campos et al. | |
| 2017/0008904 A1 | 1/2017 | Crew et al. | |
| 2017/0037004 A1 | 2/2017 | Crew et al. | |
| 2017/0065719 A1 | 3/2017 | Qian et al. | |
| 2017/0121321 A1 | 5/2017 | Crews et al. | |
| 2017/0281784 A1 | 10/2017 | Wang et al. | |
| 2017/0307614 A1 | 10/2017 | Crews et al. | |
| 2017/0327469 A1 | 11/2017 | Crew et al. | |
| 2017/0348298 A1 | 12/2017 | Carrancio et al. | |
| 2018/0015087 A1 | 1/2018 | Liu et al. | |
| 2018/0072711 A1 | 3/2018 | Crew et al. | |
| 2018/0099940 A1 | 4/2018 | Crew et al. | |
| 2018/0125821 A1 | 5/2018 | Crew et al. | |
| 2018/0147202 A1 | 5/2018 | Crew et al. | |
| 2018/0155322 A1* | 6/2018 | Crew | A61K 31/501 |
| 2018/0177750 A1 | 6/2018 | Crew et al. | |
| 2018/0179183 A1 | 6/2018 | Crew et al. | |
| 2018/0193470 A1 | 7/2018 | Crew et al. | |
| 2018/0215731 A1 | 8/2018 | Crew et al. | |
| 2018/0228907 A1 | 8/2018 | Crew et al. | |
| 2018/0237418 A1 | 8/2018 | Crew et al. | |
| 2018/0256586 A1 | 9/2018 | Crew et al. | |
| 2020/0231567 A1 | 7/2020 | Man et al. | |
| 2021/0238193 A1 | 8/2021 | Mainolfi et al. | |
| 2022/0022011 A1 | 1/2022 | Bhatnagar et al. | |
| 2022/0081416 A1 | 3/2022 | Boulton et al. | |
| 2022/0089580 A1 | 3/2022 | Chen et al. | |
| 2022/0193072 A1 | 6/2022 | Chen et al. | |
| 2022/0274955 A1 | 9/2022 | Crew et al. | |

(56) References Cited

U.S. PATENT DOCUMENTS

| | | |
|---|---|---|
| 2022/0388984 A1 | 12/2022 | Crew et al. |
| 2023/0069491 A1 | 3/2023 | Chen et al. |
| 2023/0357211 A1 | 11/2023 | Clark et al. |

FOREIGN PATENT DOCUMENTS

| | | |
|---|---|---|
| CN | 102477017 A | 5/2012 |
| CN | 102477033 A | 5/2012 |
| CN | 103688176 A | 3/2014 |
| CN | 103159736 B | 5/2015 |
| CN | 113816927 A | 12/2021 |
| CN | 114085213 A | 2/2022 |
| EA | 19041 B1 | 12/2013 |
| EP | 2985285 A1 | 2/2016 |
| JP | H10-204028 A | 8/1998 |
| JP | 2004-525889 A | 8/2004 |
| JP | 2010-502627 A | 1/2010 |
| RU | 2008112221 A | 10/2009 |
| RU | 2448101 C2 | 4/2012 |
| RU | 2011121567 A | 10/2012 |
| RU | 2487873 C2 | 7/2013 |
| RU | 2012138709 A | 3/2014 |
| RU | 2535347 C2 | 12/2014 |
| WO | WO 1998/003502 A1 | 1/1998 |
| WO | WO 1998/045287 A1 | 10/1998 |
| WO | WO 1999/015521 A1 | 4/1999 |
| WO | WO 2000/066119 A1 | 11/2000 |
| WO | WO 2002/066512 A1 | 8/2002 |
| WO | WO 2002/100845 A1 | 12/2002 |
| WO | WO-03062236 A1 | 7/2003 |
| WO | WO-2005005426 A1 | 1/2005 |
| WO | WO 2005/097791 A1 | 10/2005 |
| WO | WO 2006/069063 A1 | 6/2006 |
| WO | WO-2006084015 A2 | 8/2006 |
| WO | WO 2006/113942 A2 | 10/2006 |
| WO | WO 2007/101347 A1 | 9/2007 |
| WO | WO 2007/106670 A2 | 9/2007 |
| WO | WO 2007/130626 A2 | 11/2007 |
| WO | WO-2007140222 A2 | 12/2007 |
| WO | WO 2008/011392 A2 | 1/2008 |
| WO | WO 2008/014236 A1 | 1/2008 |
| WO | WO-2008032157 A2 | 3/2008 |
| WO | WO 2008/109057 A1 | 9/2008 |
| WO | WO 2008/128121 A1 | 10/2008 |
| WO | WO 2008/128171 A2 | 10/2008 |
| WO | WO 2008/134679 A1 | 11/2008 |
| WO | WO 2009/015254 A1 | 1/2009 |
| WO | WO-2009019274 A1 | 2/2009 |
| WO | WO 2009/060292 A2 | 5/2009 |
| WO | WO-2010020675 A1 | 2/2010 |
| WO | WO-2010075074 A1 | 7/2010 |
| WO | WO 2010/107485 A1 | 9/2010 |
| WO | WO 2010/141805 A1 | 12/2010 |
| WO | WO-2010138588 A2 | 12/2010 |
| WO | WO 2011/008260 A2 | 1/2011 |
| WO | WO-2011076786 A1 | 6/2011 |
| WO | WO 2012/003281 A2 | 1/2012 |
| WO | WO 2012/040527 A2 | 3/2012 |
| WO | WO-2012064805 A1 | 5/2012 |
| WO | WO 2012/078559 A2 | 6/2012 |
| WO | WO 2012/090104 A1 | 7/2012 |
| WO | WO 2013/071035 A1 | 5/2013 |
| WO | WO 2013/071039 A1 | 5/2013 |
| WO | WO 2013/106643 A2 | 7/2013 |
| WO | WO 2013/106646 A2 | 7/2013 |
| WO | WO-2013097224 A1 | 7/2013 |
| WO | WO 2013/170147 A1 | 11/2013 |
| WO | WO 2013/175417 A1 | 11/2013 |
| WO | WO 2013/178570 A1 | 12/2013 |
| WO | WO 2014/011712 A1 | 1/2014 |
| WO | WO 2014/020502 A2 | 2/2014 |
| WO | WO 2014/025759 A1 | 2/2014 |
| WO | WO-2014025964 A2 | 2/2014 |
| WO | WO 2014/038606 A1 | 3/2014 |
| WO | WO 2014/047024 A1 | 3/2014 |
| WO | WO 2014/055461 A1 | 4/2014 |
| WO | WO 2014/074658 A1 | 5/2014 |
| WO | WO 2014/100065 A1 | 6/2014 |
| WO | WO 2014/100071 A2 | 6/2014 |
| WO | WO 2014/107713 A1 | 7/2014 |
| WO | WO 2014/108452 A1 | 7/2014 |
| WO | WO 2014/123418 A1 | 8/2014 |
| WO | WO-2014128588 A1 | 8/2014 |
| WO | WO 2014/134201 A1 | 9/2014 |
| WO | WO 2014/151863 A1 | 9/2014 |
| WO | WO 2015/000867 A1 | 1/2015 |
| WO | WO 2015/000868 A1 | 1/2015 |
| WO | WO 2015/006524 A1 | 1/2015 |
| WO | WO-2015092420 A1 | 6/2015 |
| WO | WO 2015/160845 A2 | 10/2015 |
| WO | WO 2016/097071 A1 | 6/2016 |
| WO | WO 2016/105518 A1 | 6/2016 |
| WO | WO 2016/118666 A1 | 7/2016 |
| WO | WO 2016/146985 A1 | 9/2016 |
| WO | WO-2016149668 A1 | 9/2016 |
| WO | WO 2016/169989 A1 | 10/2016 |
| WO | WO 2016/172134 A2 | 10/2016 |
| WO | WO-2016166703 A1 | 10/2016 |
| WO | WO 2016/197114 A1 | 12/2016 |
| WO | WO 2017/011590 A1 | 1/2017 |
| WO | WO 2017/024318 A1 | 2/2017 |
| WO | WO 2017/024319 A1 | 2/2017 |
| WO | WO 2017/030814 A1 | 2/2017 |
| WO | WO 2017/046036 A1 | 3/2017 |
| WO | WO 2017/079267 A1 | 5/2017 |
| WO | WO 2017/160990 A1 | 9/2017 |
| WO | WO 2017/161119 A1 | 9/2017 |
| WO | WO 2017/185036 A1 | 10/2017 |
| WO | WO-2017176957 A1 | 10/2017 |
| WO | WO 2017/197051 A1 | 11/2017 |
| WO | WO-2018098280 A1 | 5/2018 |
| WO | WO-2018102725 A1 | 6/2018 |
| WO | WO-2020118213 A1 | 6/2020 |
| WO | WO-2021041348 A1 | 3/2021 |
| WO | WO-2021061204 A1 | 4/2021 |
| WO | WO-2022056368 A1 | 3/2022 |
| WO | WO-2022132652 A1 | 6/2022 |
| WO | WO-2023009521 A1 | 2/2023 |
| WO | WO-2023102379 A1 | 6/2023 |
| WO | WO-2023213197 A1 | 11/2023 |
| WO | WO-2024049926 A1 | 3/2024 |
| WO | WO-2024083716 A1 | 4/2024 |
| WO | WO-2024167904 A1 | 8/2024 |

OTHER PUBLICATIONS

U.S. Appl. No. 16/932,072, filed Jul. 17, 2020, Crew et al.
U.S. Appl. No. 17/359,424, filed Jun. 25, 2021, Crew et al.
Abraham, R.T. "Phosphatidylinositol 3-kinase related kinases" (1996) Current Opinion in Immunology. 8 (3) 412-418.
Ahn, et al. "HIF-1alpha peptide derivatives with modifications at the hydroxyproline residue as activators of HIF-1alpha" Bioorg Med Chem Lett. 19(15), 2009, 4403-4405.
Ali, S. et al. "Molecular mechanisms and mode of tamoxifen resistance in breast cancer" Bioinformation 12, 135-139 (2016).
Ardecky, RJ, et al. "Design, synthesis and evaluation of inhibitor of apoptosis protein (IAP) antagonists that are highly selective for the BIR2 domain of XIAP" Bioorg. Med. Chem. 23(14): 4253-4257 (2013).
Asano M, et al. "Design, sterioselective synthesis, and biological evaluation of novel tri-cyclic compounds as inhibitor of apoptosis proteins (IAP) antagonists" Bioorg. Med. Chem. 21(18): 5725-5737 (2013).
Bargagna-Mohan, et al. "Use of PROTACS as molecular probes of angiogenesis" Bioorg Med Chem Left. 15(11) 2005, 2724-2727.
Battista, M. J. & Schmidt, M. "Fulvestrant for the treatment of endometrial cancer" Expert Opin Investig Drugs 25, 475-483 (2016).
Bondeson, et al. "Targeted Protein Degradation by Small Molecules" (2017) Annu Rev Pharmacol. Toxicol. 57:107-123.
Bondeson, et al. "Catalytic in vivo protein knockdown by small-molecule PROTACS" National Chem Biol. 11(8) Aug. 2015, 611-617.

(56) References Cited

OTHER PUBLICATIONS

Buckley, et al. "HaloPROTACS: use of small molecule PROTACS to induce degradation of HaloTag fusion proteins" ACS Chem Biol. 10(8), 2015, 1831-1837.
Buckley, et al. "Small-molecule inhibitors of the interaction between the E3 ligase VHL and HIF1α" Anew Chem Int Ed Engl.51(46), Nov. 12, 2012, 11463-11467.
Buckley, et al. "Targeting the von Rippel-Lindau E3 ubiquitin ligase usingsmall molecules to disrupt the VHL/HIF-1α interaction" Journal of the American Chemical Society, Feb. 27, 2012, 134(10): 4465-4468.
Burke, et al. "Design, Synthesis and Biological Evaluation of Doxorubicin-Formaldehyde Conjugates Targeted to Breast Cancer Cells" Journal of Medicinal Chemistry, Jan. 24, 2004, vol. 47, No. 5, pp. 1193-1206.
Burslem, et al. (2017) "Small-Molecule Modulation of Protein Homeostasis" Chem Rev 117(17):11269-11301.
Capitosti, S. et al. "Thalidomide analogues demonstrate dual inhibition of both angiogenesis and prostate cancer" Bioorganic & Medicinal Chemistry 12, (2004) 327-336.
Carmony, KC, et al. "PROTAC-Induced Proteolytic Targeting" Methods Mol. Biol. 2012, vol. 832, pp. 627-638.
CAS Registry No. 1004933-70-3, which entered STN on Feb. 21, 2008.
CAS Registry No. 871986-52-6 entered STN Jan 16, 2006.
Chene, P., et al. "Inhibiting the p53-MDM2 interaction: an important target for cancer therapy" Nat. Rev. Cancer (2003), 3, 102-109.
Cheng-Gen., Feng, et al. "Progress in Antiestrogens for the Treatment of Breast Cancer" Chinese Journal of New Drugs, vol. 15. No. 13, pp. 1051-1057, Dec. 31, 2006.
Cohen, F., et al. "Orally bioavailable antagonists of inhibitor of apoptosis proteins based on an azabicyclooctane scaffold" J. Med. Chem. 52(6), 1723-1730 (2009).
Cohen, F., et al. "Antagonists of inhibitors of apoptosis proteins based on thiazole amide isosteres" Bioorg. Med. Chem. Lett. 20(7), 2229-2233 (2010).
Connor, C.E., et al. "Circumventing tamoxifen resistance in breast cancers using antiestrogens that induce unique conformational changes in the estrogen receptor" Cancer Res. 61: 2917-2922 (2001).
Contino-Pepin, Christiane, et al. "Preliminary biological evaluations of new thalidomide analogues for multiple sclerosis application" Bioorganic & Medicinal Chemistry Letter 19 (2009), 878-881.
Corson, et al. "Design and applications of bifunctional small molecules: why two heads are better than one" ACS Chemical Biology vol. 3 No. 11, pp. 677-692; Nov. 21, 2008.
Crews, C. M. "Targeting the undruggable proteome: the small molecules of my dreams" Chem Biol 17, 551-555, doi:S1074-5521(10)00196-1 [pii] 10.1016/j.chembiol.2010.05.011 (2010).
Cromm, et al. (2017) "Targeted Protein Degradation: from Chemical Biology to Drug Discovery" Cell Chem Biol 24(9):1181-1190.
Cyrus, et al. "Jostling for position: optimizing linker location in the design of estrogen receptor-targeting PROTACs" Chem Med Chem. 5(7), Jul. 5, 2010, 979-985.
Cyrus, K. et al, "Impact of Linker Length on the Activity of PROTACs" Mol. Biosyst. 2011, vol. 7, No. 2, pp. 359-364.
Cyrus, K. et al, "Two-Headed PROTAC: An Effective New Tool for Targeted Protein Degradation" Chembiochem. 2010, vol. 11, pp. 1531-1534.
Deroo, B.J. et al. "Estrogen receptors and human disease" Journal of Clinical Investigation, (2006), vol. 116(3), pp. 561-570.
Di, J. et al. "Reactivation of p53 by inhibiting Mdm2 E3 Ligase: a novel antitumor approach" Current Cancer Drug Targets (2011), 11(8), 987-994.
Ding, Q., et al. "Discovery of RG7388, a potent and selective p53-MDM2 inhibitor in clinical development" J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).

Dixon, S. J., et al. "Identifying druggable disease-modifying gene products" Curr Opin Chem Biol 13, 549-555, doi:S1367-5931(09)00107-0 [pii] 10.1016/j.cbpa.2009.08.003 (2009).
Fischer, et al. "Structure of the DDBl-DRBN E3 Ubiquitin ligase in complex with thalidomide" Nature, vol. 000, pp. 1-5 (2014).
Flygare, J.A., et al. "Small-molecule pan-IAP antagonists: a patent review" Expert Opin. Ther. Pat. 20 (2), 251-267 (2010).
Gadd, M.S., et al. "Structural basis of PROTAC cooperative recognition for selective protein degradation" Nat Chem Biol 13, 514-521 (2017).
Galdeano, et al. "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities" Journal Med Chem, Aug. 2014, vol. 157, pp. 8657-8663.
Garner, F., Shomali, M. Paquin, D. Lyttle, C.R. & Hattersley, G. "RAD1901: a novel, orally bioavailable selective estrogen receptor degrader that demonstrates antitumor activity in breast cancer xenograft models" Anticancer Drugs 26, 948-956 (2015).
Golub, et al. "Molecular classification of cancer: class discovery and class prediction by gene expression monitoring" Science 286, 531-537 (1991).
Gosink, M., et al. "Redirecting the specificity of ubiquitination by modifying ubiquitin-conjugating enzymes" Pro. Natl. Acad Sci, vol. 92, pp. 9117-9121, 1995.
Haupt, Y., et al. "Mdm2 promotes the rapid degradation of p53" Nature 387, 296-299 (1997).
Heldring, et al. "Estrogen Receptors: How Do They Signal and What are Their Targets" Physiological Reviews (2007), vol. 87, pp. 905-931.
Hennessy, E. J., et al. "Discovery of aminopiperidine-based Smac mimetics as IAP antagonists" Bioorg. Med. Chem. Lett. 22(4), 1690-1694 (2012).
Hines, J., et al. "Posttranslational protein knockdown coupled to receptor tyrosine kinase activation with phosphoPROTACs" Proc Natl Acad Sci USA 110, 8942-8947 (2013).
Hird et al. "Structure-based design and synthesis of tricyclic IAP (Inhibitors of Apoptosis Proteins) inhibitors" Bioorg. Med. Chem. Lett. 24(7): 1820-1824 (2014).
Hoffmann, J., et al. "Characterization of New Estrogen Receptor Destabilizing Compounds: Effects on Estrogen-Sensitive and Tamoxifen-Resistant Breast Cancer" JNCI Journal of the National Cancer Institute 96, 210-218 (2004).
Hon, et al. "Structural basis for the recognition of hydroxyproline in HIF-1α by pVHL" Nature 417, Jun. 27, 2002, 975-978.
Huang, et al. (2016) "Drugging the undruggables: exploring the ubiquitin system for drug development" Cell Res 26(4):484-498.
Hughes, et al. (2017) "Molecular recognition of ternary complexes: a new dimension in the structure-guided design of chemical degraders" Essays Biochem 61(5):505-516.
Ivan, M. et al. "HIFα Targeted for VHL-Mediated Destruction by Proline Hydroxylation: Implications for $O_2$ Sensing" Science, vol. 292, No. 5516, pp. 464-468, 2001.
Jang, E.R. et al. "Targeted Degradation of Proteins by PROTACs" Curr. Protoc. Chem. Biol. 2010, vol. 2, No. 2, pp. 71-87.
Jiang, et al. "Synthesis of 7alpha-substituted derivatives of 17beta-estradiol" Steroids 71(5), May 2006, 334-342 (Abstract).
Jordan, V.C. et al. "A monohydroxylated metabolite of tamoxifen with potent antioestrogenic activity" Endocrinol 75: 305-316 (1977).
Kim, K.S. "Discovery of tetrahydroisoquinoline-based bivalent heterodimeric IAP antagonists" Bioorg. Med. Chem. Lett. 24(21), 5022-5029 (2014).
Knott, Edward (1955). "Compounds containing sulphur chromophores. Part I. The action of bases on heterocyclic sulphide quartemary salts" Journal of the Chemical Society (resumed). 10.1039/jr9550000916. 949-954.
Kronke, et al, "Lenalidomide Causes Selective Degradation of IKZFl and IKZF3 in Multiple Myeloma Cells" Science 343, 301-305 (2014).
Lai, A., et al. "Identification of GDC-0810 (ARN-810), an Orally Bioavailable Selective Estrogen Receptor Degrader (SERD) that Demonstrates Robust Activity in Tamoxifen-Resistant Breast Cancer Xenografts" J. Med. Chem. 58, 4888-4904 (2015).

(56) References Cited

OTHER PUBLICATIONS

Lai, A.C. et al. "Modular PROTAC Design for the Degradation of Oncogenic BCR-ABL" Agnew Chem Int Ed Engl 55, 807-810 (2016).

Lai, et al. (2017) "Induced protein degradation: an emerging drug discovery paradigm" Nat Rev Drug Discov 16(2):101-114.

Lala, et al. "Role of nitric oxide in tumor progression: Lessons from experimental tumors" Cancer and Metastasis Reviews 17:91-106 (1998).

Lebraud, H., et al. "Protein Degradation by In-Cell Self-Assembly of Proteolysis Targeting Chimeras" ACS Central Science, 2: 927-934 (2016).

Lee, et al. "Targeted Degradation of the Aryl Hydrocarbon Receptor by the PROTAC Approach: A Useful Chemical Genetic Tool" ChemBioChem vol. 8, Issue 17, pp. 2058-2062, Nov. 23, 2007.

Levine, et al. "Targeting the androgen receptor with steroid conjugates" J. Med. Chem. vol. 57. No. 20. pp. 8224-8237, (2014).

Li, Yan, et al. "Single polymer-drug conjugate carrying two drugs for fixed-dose co-delivery" Medicinal Chemistry, 2014, vol. 4(10): 676-683.

Liu, Hong, et al. "Bioactivation of the selective estrogen receptor modulator desmethylated arzoxifene to quinoids: 4'-fluoro substitution prevents quinoid formation" Chem. Res. Toxicol. 2005, 18, 162-173.

Liu, K. et al. "Design and biological characterization of hybrid compounds of curcumin and thalidomide for multiple myeloma" Org. Biomol. Chem. 2013, 11, 4757-4763.

Lopez-Girona, A., et al. Cereblon is a direct protein target for immunomodulatory and antiproliferative activities of lenalidomide and pomalidomide Leukemia 26: 2326-2335, 2012.

Lu, et al. "Hijacking the E3 ubiquitin ligase cereblon to efficiently target BRD4"Chem Biol 22(6), 2015, 755-763.

Lu, et al. "The myeloma drug lenalidomide promotes the cereblon-dependent destruction of ikaros proteins" Science 343, 305-309 (2014).

Mahalingam, D., et al. "Targeting HSP90 for cancer therapy" Br J Cancer 100, 1523-1529 (2009).

Maniaci C., et al. (2017) "Homo-PROTACs: bivalent small-molecule dimerizers of the VHL E3 ubiquitin ligase to induce self-degradation" Nat Commun 8(1):830 1-13.

Mannhold, R., et al. "IAP antagonists: promising candidates for cancer therapy" Drug Discov. Today, 15 (5-6), 210-219 (2010).

Maximov, et al. "The Discovery and Development of Selective Estrogen Receptor Modulators (SERMs) for Clinical Practice" Curr Clin Pharmacol. May 2013; 8(2): 135-155.

McGuire, et al. "Taxol: A unique antineoplastic agent with significant activity in advanced ovarian epithelial neoplasms" Ann. Intern, Med. 111:273-279, 1989.

MEDLINE Plus Trusted Health Information for You, www.nlm.nih.gov/medlineplus/cancer.html pp. 1-10, (2007).

Min, Jung-hyun, et al. "Structure of an HIF-1-alpha-pVHL complex: hydroxyproline recognition in signaling" Jun. 7, 2002, 296: 1886-1889.

Miyazaki, M., et al. "Discovery of DS-5272 as a promising candidate: a potent and orally active p53-MDM2 interaction inhibitor" Bioorg. Med. Chem. Lett. (2015) 23, 2360-2367.

Muller, G. et al. "Amino-Substituted Thalodomide Analogs: Potent Inhibitors of TNF-α Production"Bioorganic & Medicinal Chemistry Letters 9 (1999) 1625-1630.

Ndubaku, C, et al. "Antagonism of c-IAP and XIAP proteins is required for efficient induction of cell death by small-molecule IAP antagonists" ACS Chem Biol. Jul. 17, 2009;4(7):557-566.

Neklesa, T.K., et al. "Chemical biology: Greasy tags for protein removal" Nature 487, 308-309 (2012).

Neklesa. "Targeted protein degradation by PROTACs" Pharmacology & Therapeutics 174, 138-144 (2017).

Nikolovska-Coleska, et al. "Interaction of a cyclic, Bivalent Smac Mimetic with the X-linked inhibitor of apoptosis protein" Biochemistry, 2008, 47(37), pp. 9811-9824.

Notice of Grounds of Rejection for JP Application No. 2020-033150, filing date of Oct. 11, 2017, dated Aug. 18, 2020, English Translation, 4 pages.

Ohoka, N., et al. "SNIPER(TACC3) induces cytoplasmic vacuolization and sensitizes cancer cells to Bortezonlib" Cancer Sci. 108, 1032-1041 (2017).

Ohoka, et al. "In Vivo Knockdown of Pathogenic Proteins via Specific and Nongenetic Inhibitor of Apoptosis Protein (IAP)-dependent Protein Erasers (SNIPERs)" J Biol Chem. Mar. 17, 2017; 292(11): 4556-4570.

Office Action and Prior Art Search Report for RU Application No. 2020106142, filing date of Dec. 1, 2017, dated Aug. 7, 2020, English Translation, 7 pages.

Oost, T.K., et al. "Discovery of potent antagonists of the antiapoptotic protein XIAP for the treatment of cancer" Journal of Medicinal Chemistry 2004, 47, 4417-4426.

Ottis P, et al. (2017) "Assessing Different E3 Ligases for Small Molecule Induced Protein Ubiquitination and Degradation" ACS Chem Biol 12(10):2570-2578.

Ottis, et al. (2017) "Proteolysis-Targeting Chimeras: Induced Protein Degradation as a Therapeutic Strategy" ACS Chem Biol 12(4):892-898.

Perez, H. L., et al. "Discovery of potent heterodimeric antagonists of inhibitor of apoptosis proteins (IAPs) with sustained antitumor activity" J. Med. Chem. 58(3), 1556-1562 (2015).

Poutiainen, P.K., et. al. "Design, synthesis, and biological evaluation of nonsteroidal cycloalkane[d]isoxazole-containing androgen receptor modulators" J. Med. Chem. 55, 6316-6327 (2012).

Puppala, D., et al. "Development of an Aryl Hydrocarbon Receptor Antagonist Using the Proteolysis-Targeting chimeric Molecules Approach: A Potential Tool for Chemoprevention," Mol. Pharmacol. 2008, vol. 73, No. 4, pp. 1064-1071.

Qin, Zhihui, et al. "Benzothiophene selective estrogen receptor modulators with modulated oxidative activity and receptor affinity" J. Med Chem 2007, 50, 2682-2692.

Raina, et al. (2017) "Targeted protein knockdown using small molecule degraders" Curr. Opin Chem Biol 39:46-53.

Raina, K. et al. "PROTAC-induced BET protein degradation as a therapy for castration-resistant prostate cancer" Proc Natl Acad Sci USA 113, 7124-7129 (2016).

Remillard D., et al. (2017) "Degradation of the BAF Complex Factor BRD9 by Heterobifunctional Ligands" Angew Chem Int Ed Engl 56(21):5738-5743.

Rew, Y., et al. "Discovery of AM-7209, a potent and selective 4-amidobenzoic acid inhibitor of the MDM2-p53 interaction" J Med Chem. Dec. 26, 2014;57(24):10499-10511. doi: 10.1021/jm501550p. Epub Dec. 4, 2014. PubMed PMID: 25384157.

Robertson, J. F. R. "Fulvestrant (Faslodex)—how to make a good drug better" Oncologist 12, 774-784(2007).

Rodriguez-Gonzalez, et al. "Targeting steroid hormone receptors for ubiquitination and degradation in breast and prostate cancer" Oncogene. 27 (57), Dec. 4, 2008, 7201-7211.

Rotili, D., et al. "Photoactivable peptides for identifying enzyme-substrate and protein-protein interactions" Chem. Commun. 47(5), Feb. 2011, 1488-1490.

Ruchelman, A., et al. "Isosteric analogs of lenalidominde and pomalidomide: Synthesis and biological activity" Bioorganic & Medicinal Chemistry Letters 23 (2013) 360-365.

Sakamoto, et al. "Development of Protacs to target cancer-promoting proteins for ubiquitination and degradation" Mol Cell Proteomics. 2(12), Dec. 2003, 1350-1358.

Sakamoto, et al. "Protacs: chimeric molecules that target proteins to the Skp 1-Cullin-F box complex for ubiquitination and degradation" Proc Natl Acad Sci USA 98(15), Jul. 17, 2001, 8554-8559.

Salami, J. & Crews, C. M. "Waste disposal—An attractive strategy for cancer therapy" Science 355, 1163-1167 (2017).

Schiedel, M., et al. "Chemically Induced Degradation of Sirtuin 2 (Sirt2) by a Proteolysis Targeting Chimera (PROTAC) Based on Sirtuin Rearranging Ligands (SirReals)" J Med Chem. (2017), 61:482-491.

Scott, et al. "Tetrahydroisoquinoline Phenols: Selective Estrogen Receptor Downregulator Antagonists with Oral Bioavailability in Rat" ACS Med Chem Lett. Jan. 14, 2016; 7(1): 94-99.

(56) References Cited

OTHER PUBLICATIONS

Schneekloth, et al. "Chemical Genetic Control of Protein Levels: Selective in Vivo Targeted Degradation" J Am Chem Soc. 126(12), Mar. 31, 2004, 3748-3754.
Schneekloth, et al. "Targeted intracellular protein degradation induced by a small molecule: En Route to chemical proteomics," Bioorg. Med. Chem. Lett. 18 (2008) 5904-5908.
Smith, et al. "Targeted Intracellular Protein Degradation Induced by a Small Molecule: En Route to Chemical Proteomics" Bioorg Med Chem Lett. 18(22), Nov. 15, 2008, 5904-5908.
Stewart, Scott G. et al. "Efforts toward elucidating Thalidomide's molecular target: An Expedient Synthesis of the first Thalidomide Biotin Analogue" Org. Biomol. Chem. 2010, 8, 4059-4062.
STN transcript excerpt Nov. 24, 2017 "Compounds containing sulfur Chromophores v. Complex cyanines".
Stoppler, Melissa Conrad. Endometriosis [online], "Endometriosis Definition and Facts" URL http://www.medicinenet.com/endometriosis/article.htm, retrieved on Apr. 5, 2017.
Stoppler, Melissa Conrad. Endometriosis [online], "What about surgery for Endometriosis?" URL http://www.medicinenet.com/endometriosis/article.htm, retrieved on Apr. 5, 2017.
Suh, N. et al. "Arzoxifene, a new selective estrogen receptor modulator for chemoprevention of experimental breast cancer" Cancer Res. 61, 8412-8415 (2001).
Sun, D., et al. "Discovery of AMG 232, a potent, selective, and orally bioavailable MDM2-p53 inhibitor in clinical development" J Med Chem. Feb. 27, 2014;57(4):1454-72. doi: 10.1021/jm401753e. Epub Feb. 5, 2014. PubMed PMID: 24456472.
Sun, et al. "Potent bivalent Smac mimetics: effect of the linker on binding to inhibitor apoptosis proteins (IAPs) and anticancer activity" J. Med. Chem. 53, 3306-3318 (2011).
Toure, et al. (2016) "Small-Molecule PROTACS: New Approaches to Protein Degradation" Angew Chem Int Ed Engl 55(6):1966-1973.
Trewartha, D. and Carter, K. "Advances in prostate cancer treatment" Nat Rev Drug Discov. Nov. 2013;12(11):823-824. doi: 10.1038/nrd4068. PubMed PMID: 24172327.
Turk, B. E. "Binding of thalidomide to $\alpha_1$-acid glycoprotein may be involved in its inhibition of tumor necrosis factor alpha production" Proc. Natl. Acad. Sci. U.S.A. 1996, 93, 7552-7556.
Vamos, M., et al. "Expedient synthesis of highly potent antagonists of inhibitor of apoptosis proteins (IAPs) with unique selectivity for ML-IAP" ACS Chem. Biol. 8(4), 725-732 (2013).
Van Molle, et al. "Dissecting fragment-based lead discovery at the von Rippel-Lindau protein:hypoxia inducible factor 1α protein-protein interface" Chem Biol. 19(10), Oct. 26, 2012, 1300-1312.
Vassilev, et al. "In vivo activation of the p53 pathway by small-molecule antagonists of MDM2" Science 303, Feb. 6, 2004, 844-848.
Vazquez, A., et al. "The genetics of the p53 pathway, apoptosis and cancer therapy" Nat. Rev. Drug. Dis. 7, 979-987 (2008).
Vu, B., et al. "Discovery of RG7112: a small-molecule MDM2 inhibitor in clinical development" ACS Med. Chem. Lett. (2013) 4, 466-469.
Wang, J., et al. "Discovery of novel second mitochondrial-derived activator of caspase mimetics as selective inhibitor or apoptosis protein inhibitors" J .Pharmacol. Exp. Ther. 349(2): 319-29 (2014).
Wang, C., et al. "Estrogen induces c-myc gene expression via an upstream enhancer activated by the estrogen receptor and the AP-1 transcription factor" Mol. Endocrinol. 25, 1527-1538 (2011).
Wang, S., et al. "Small-molecule inhibitors of the MDM2-p53 protein-protein interaction (MDM2 inhibitors) in clinical trials for cancer treatment" J. Med. Chem. (2015) 58, 1038-1052.
Wang, S., et al. "Temporal activation of p53 by a specific MDM2 inhibitor is selectively toxic to tumors and leads to complete tumor growth inhabitation" PNAS USA (2008) 105, 3933-3938.
Weir, H. M., et al. "AZD9496: An Oral Estrogen Receptor Inhibitor That Blocks the Growth of ER-Positive and ESRl-Mutant Breast Tumors in Preclinical Models" Cancer Res. 76, 3307-3318 (2016).
Wijayaratne, et al. "The Human Estrogen Receptor-α is a Ubiquintinated Protein whose Stability is Affected Differentially by Agonists, Antagonists, and Selective Estrogen Receptor Modulators" J. Biol. Chem. Sep. 21, 2001; 276(38): 35684-35692.
Willson, T.M., et al. "3-[4-(1,2-Diphenylbut-1-Enyl)Phenyl] Acrylic Acid: A non-steroidal estrogen with functional selectivity for bone over uterus in rats" Journal of Medicinal Chemistry, American Chemical Society, US May 25, 1994, vol. 37 No. 11, pp. 1550-1552.
Winter, et al. "Phthalimide Conjugation as a strategy for in vivo target protein degradation" Science, 2015 vol. 348 (6241), pp. 1376-1381 [Pub online: May 21, 2015].
Yu, F. & Bender, W. "The mechanism of tamoxifen in breast cancer prevention" Breast Cancer Research 3, A74 (2001).
Zengerle, et al. "Selective Small Molecule Induced Degradation of the BET Bromodomain Protein BRD4" ACS Chemical Biology, Jun. 2, 2015, vol. 10, pp. 1770-1777.
Zhang B., et al. "Small-molecule MDM2-p53 inhibitors: recent advances" Future Med. Chem. (2015) 7, 631-645.
Zhang, D., et al. "Targeted Degradation of Proteins by Small Molecules: A Novel Tool for Functional Proteomics" Comb. Chem. High Throughput Screen. 2004, vol. 7, No. 7, pp. 689-697.
Zhong, H., et al. "Modulation of Hypoxia-inducible Factor 1a Expression by the Epidermal Growth Factor/Phosphatidylinositol 3-Kinase/PTEN/AKT/FRAP Pathway in Human Prostate Cancer Cells: Implications for Tumor Angiogenesis and Therapeutics" Cancer Res, (2000) 60(6), 1541-1545.
Zhou, B., et al. "Discovery of a Small-Molecule Degrader of Bromodomain and Extra-Terminal (BET) Proteins with Picomolar Cellular Potencies and Capable of Achieving Tumor Regression" J Med Chem. 61(2), 462-481 (2018) (DOI:10.1021/acs.jmedchem.6b01816) (2017).
Byrn et al. "Pharmaceutical Solids: A Strategic Approach to Regulatory Considerations" Pharmaceutical Research, 1995, 12(7):945-954.
Hansen, et al., "Potent and selective pyrazole-based inhibitors of B-Raf kinase", Bioorganic & Medicinal Chemistry Letters, 2008, 18(16):4692-4695.
Yudong et, al., "PROTAC and its application in the treatment of cancer" Chemistry of Life, 2014, 34:549-554 (English Abstract included).
ClinicalTrials.gov Identifier: NCT01740427, "A Study of Palbociclib (PD-0332991) + Letrozole vs. Letrozole for 1st Line Treatment of Postmenopausal Women With ER+/HER2-Advanced Breast Cancer (PALOMA-2)" [online] https://clinicaltrials.gov/ct2/show/NCT01740427?term=NCT01740427&draw=2&rank=1 (First Posted—Dec. 4, 2012, Access Date—Jun. 7, 2023); 13 pages.
ClinicalTrials.gov Identifier: NCT01942135, "Palbociclib (PD-0332991) Combined With Fulvestrant in Hormone Receptor+ HER2-Negative Metastatic Breast Cancer After Endocrine Failure (PALOMA-3)" [online] https://clinicaltrials.gov/ct2/show/NCT01942135?term=NCT01942135&draw=2&rank=1 (First Posted—Sep. 13, Access Date—Jun. 7, 2023); 14 pages.
ClinicalTrials.gov Identifier: NCT04072952, "A Phase 1/2 Trial of ARV-471 Alone and in Combination With Palbociclib (IBRANCER) in Patients With ER+/HER2—Locally Advanced or Metastatic Breast Cancer (mBC)" [online] https://www.clinicaltrials.gov/ct2/history/NCT04072952?V_7=View#StudyPageTop (First Posted—Aug. 27, 2019, Access Date—Jun. 7, 2023); 7 pages.
Co-pending U.S. Appl. No. 18/070,408, inventors Qian; Yimin et al., filed Nov. 28, 2022.
Feng, C., "Anti-estrogens: current status and trends in the treatment of breast cancer", Chinese Journal of New Drugs (2006); 15(13):1051-1057.
Guranda, D. T., et al., "Preparation of Drug Polymorphs (A Review)", Khim. Farm. Zhurnal (2010); 44(5): 22-28; 7 pages with English Abstract.
Loibl, S., et al., "Palbociclib combined with fulvestrant in premenopausal women with advanced breast cancer and prior progression on endocrine therapy: PALOMA-3 results", The Oncologist (2017); 22(9): 1028-1038.
Mullard, A., "First targeted protein degrader hits the clinic", Nature Reviews, Drug Discovery (Apr. 2019); 18: 237-239.

(56) References Cited

OTHER PUBLICATIONS

Scudellari, M., "The protein slayers", Nature (Mar. 21, 2019); 567: 298-300.
Yamamoto-Ibusuki, M., et al., "Targeted therapies for ER+/HER2- metastatic breast cancer", BMC Medicine (2015); 13: 137; 12 pages.
Belikov, V.G, "Pharmaceutical Chemistry. Chapter 2.6 Relationship between the chemical structure, properties of substances and their effect on the body", MEDpress-inform (2007); pp. 27-29; 14 pages with English translation.
Database STN, CAS Registry No. 2614417-50-2, "2,6- Piperidinedione, 3-[1,3-dihydro-1-oxo-5-[4-[[1-[4-[(1R,2S)-1,2,3,4- tetrahydro-6-hydroxy-2-phenyl-1-naphthalenyl]phenyl]-4- piperidinyl]methyl]-1-piperazinyl]-2H-isoindol-2-yl]-, rel-", Chemical Abstracts Service, American Chemical Society; entered Mar. 19, 2021; 1 page.
Dyson, G. et al., "Chemistry of Synthetic Drugs", Moscow, MIR (1964); pp. 12-19; 25 pages with English machine translation.
Kharkevich D.A., "Pharmacology/Textbook", 10th edition, (2010); pp. 72-82; 14 pages with English Summary.
Mashkovsky, M.D., "Medicaments (Doctor's Manual)", 14th Edition, vol. 1., Moscow. (2001), pp. 11; 6 pages.
Ohoka., "Supplemental Experimental Procedure" [online] https://www.jbc.org/lookup/suppl/doi:10.1074/jbc.M116.768853/-/DC1/jbc.M116.768853-1.docx (2017); 48 pages.
Patel, H. K., et al., "Elacestrant (RAD1901) exhibits anti-tumor activity in multiple ER+ breast cancer models resistant to CDK4/6 inhibitors", Breast Cancer Research (2019); 21(1): 1-17.
Pokrovsky, V.I., "Small Medical Encyclopedia", Medicine (1996); V5: 90-96; 12 pages with English translation of relevant portion.
Xi, J., et al., "Sequencing endocrine therapy for metastatic breast cancer: what do we do after disease progression on a CDK4/6 inhibitor?", Current Oncology Reports (2020); 22(6): 1-12.
Database STN, CAS Registry No. 2229711-68-4, "2,6- Piperidinedione, 3-[1,3-dihydro- 1-oxo-5-[4-[1-[4-[(1R,2S)-1,2,3,4- tetr ahydro-6-hydroxy-2-phenyl-1- naphthalenyl]phenyl]-4- piperidinyl]methyl]-1-piperaz inyl]-2H-isoindol-2-yl]-, (3S)-", Chemical Abstracts Service, American Chemical Society; entered Jun. 29, 2018; 2 pages.
Chou, T-C., "Drug combination studies and their synergy quantification using the Chou-Talalay method", Cancer Research (2010); 70(2): 440-446.
Iwamoto, N., et al., "Efficacy and toxicity of palbociclib in heavily treated patients with metastatic breast cancer", Annals of Cancer Research and Therapy (2018); 26(2): 105-109.
Flanagan, J., et al., "Identification of Oral Estrogen Receptor PROTAC Degraders for Breast Cancer", Arvinas meeting poster, San Antonio Breast Cancer Symposium (Dec. 5-9, 2017); 1 page.
Arvinas, Inc., "Arvinas Announces ARV-471 Achieves a Clinical Benefit Rate of 38% in Evaluable Patients and Continues to Show a Favorable Tolerability Profile in its Phase 2 Expansion Trial (VERITAC)", Press Release (Nov. 22, 2022); 3 pages.
Arvinas, Inc. "Clinical Program Update: ARV-471 & ARV-110", Presentation (Dec. 14, 2020) [Online] https://web.archive.org/web/20201216092611/https://ir.arvinas.com/static-files/a e52b7dd-e872-483a-bd26-070bae7d56b8 (Access Date: Nov. 9, 2023); 43 pages.
Cordon-Cardo, C., "Mutations of cell cycle regulators. Biological and clinical implications for human neoplasia", The American Journal of Pathology (1995); 147(3): 545-560.
Cristofanilli, M., et al., "Fulvestrant plus palbociclib versus fulvestrant plus placebo for treatment of hormone-receptor-positive, HER2- negative metastatic breast cancer that progressed on previous endocrine therapy (PALOMA-3): final analysis of the multicentre, double-blind, phase 3 randomised controlled trial", The Lancet Oncology (2016); 17(4): 425-439.
Database STN, CAS Registry No. 2229711-68-4, "2,6- Piperidinedione, 3-[1,3-dihydro-1-oxo-5-[4-[1-[4-[(1R,2S)-1,2,3,4- tetr ahydro-6-hydroxy-2-phenyl-1-naphthalenyl]phenyl]-4- piperidinyl]methyl]-1-piperaz inyl]-2H-isoindol-2-yl]-, (3S)-", Chemical Abstracts Service, American Chemical Society; entered Jun. 2, 20189; 2 pages.
Demichele, A., et al., "CDK 4/6 inhibitor palbociclib (PD0332991) in Rb+ advanced breast cancer: phase II activity, safety, and predictive biomarker assessment", Clinical Cancer Research (2015); 21(5): 995-1001.
Durairaj, C., et al., "Palbociclib has no clinically relevant effect on the QTc interval in patients with advanced breast cancer", Anti-Cancer Drugs (2018); 29(3): 271-280.
Finn, R., S., et al., "Palbociclib and letrozole in advanced breast cancer", New England Journal of Medicine (2016); 375(20): 1925-1936.
Flanagan, J., et al., "ARV-471, an oral estrogen receptor PROTAC™ protein degrader for breast cancer", Arvinas meeting poster, San Antonio Breast Cancer Symposium (Dec. 4-8, 2018); 1 page.
Hall, M., et al., "Genetic alterations of cyclins, cyclin-dependent kinases, and Cdk inhibitors in human cancer", Advances in Cancer Research (1996); 68: 67-108.
Hamilton, E. P., et al., "ARV-471, an estrogen receptor (ER) Protac degrader, combined with palbociclib in advanced ER+/human epidermal growth factor receptor 2-negative breast cancer: Phase Ib cohort (part C) of a phase 1/2 study", Journal of Clinical Oncology (Jun. 1, 2022); 1 page.
IBRANCE® (palbociclib) capsules and tablets—Capsules: 75 mg, 100 mg and 125 mg; Tablets: 75 mg, 100 mg and 125 mg; Product Monograph Including Patient Medication Information, Revised Date: Jul. 1, 20215, Submission Control No. 4414444, Prepared by: Pfizer Canada ULC, 17300 Trans-Canada Highway, Kirkland, Quebec H9J 2M5 Canada; 55 pages.
IBRANCE® (palbociclib) capsules, for oral use—Capsules: 125 mg, 100 mg, and 75 mg.; Label; Highlights of Prescribing Information, Patient Information approved by the U.S. Food and Drug Administration, Revised: Apr. 2019 (Apr. 2019), Initial U.S. Approval: 2015, Reference ID: 4414444, Distributed by: Pfizer Labs, Division of Pfizer Inc., New York, NY 10017 USA, 24 pages.
Johnson, D. G., et al., "Cyclins and cell cycle checkpoints", Annual Review of Pharmacology and Toxicology (1999); 39(1): 295-312.
Karp, J. E., et al., "Molecular foundations of cancer: new targets for intervention", Nature Medicine (1995); 1(4): 309-320.
Knudsen, E. S., et al., "The strange case of CDK4/6 inhibitors: mechanisms, resistance, and combination strategies", Trends in Cancer (2017); 3(1): 39-55.
Morgan, D. O., "Cyclin-dependent kinases: engines, clocks, and microprocessors", Annual Review of Cell and Developmental Biology (1997); 13(1): 261-291.
O'Leary, B., et al., "Treating cancer with selective CDK4/6 inhibitors", Nature Reviews Clinical Oncology (2016); 13(7): 417-430.
World Health Organization, "Palbociclib", WHO Drug Information, Proposed INN: List 109 (2013); 27(1); p. 172; 1 page.
Wu, Y., et al., "Current therapeutic progress of CDK4/6 inhibitors in breast cancer", Cancer Management and Research (2020); 12: 3477-3487.
ClinicalTrials.gov Identifier: NCT05501769, "Researcher View | ARV-471 in Combination With Everolimus for the Treatment of Advanced or Metastatic ER+, HER2-Breast Cancer (TACTIVE-E)" [online] https://clinicaltrials.gov/study/NCT05501769?tab=table (First Submitted—Aug. 9, 2022, Access Date—Jul. 2, 2024); 9 pages.
Shah, V., V., et al., "Mammary-specific expression of Trim24 establishes a mouse model of human metaplastic breast cancer", Nature Communications (2021); 12(1): 5389; 15 pages.
Arriola Apelo, S. I., et al., "Alternative rapamycin treatment regimens mitigate the impact of rapamycin on glucose homeostasis and the immune system", Aging Cell (2016); 15(1): 28-38.
Ashai, N., et al., "Post-CDK 4/6 Inhibitor Therapy: Current Agents and Novel Targets", Cancers (2023); 15(1855): 1-26. DOI: 10.3390/cancers15061855.
Backman, S. A., et al., "PTEN function in mammalian cell size regulation", Current Opinion in Neurobiology (2002); 12(5): 516-522.
Bellacosa, A., et al., "Molecular alterations of the AKT2 oncogene in ovarian and breast carcinomas", International Journal of Cancer (1995); 64(4): 280-285.

(56) References Cited

OTHER PUBLICATIONS

Brown, E. J., et al., "A mammalian protein targeted by G1-arresting rapamycin-receptor complex", Nature (1994); 369(6483): 756-758.
Cantley, L. C., et al., "Oncogenes and signal transduction", Cell (1991); 64(2): 281-302.
Chandarlapaty, S., et al., "Prevalence of ESR1 mutations in cell-free DNA and outcomes in metastatic breast cancer: a secondary analysis of the BOLERO-2 clinical trial", JAMA Oncology (2016); 2(10): 1310-1315.
Chen, W., et al., "Growth retardation and increased apoptosis in mice with homozygous disruption of the Akt1 gene", Genes & Development (2001); 15(17): 2203-2208.
Cheng, J. Q., et al., "AKT2, a putative oncogene encoding a member of a subfamily of protein-serine/threonine kinases, is amplified in human ovarian carcinomas", Proceedings of the National Academy of Sciences (1992); 89(19): 9267-9271.
Cheng, J. Q., et al., "Amplification of AKT2 in human pancreatic cells and inhibition of AKT2 expression and tumorigenicity by antisense RNA", Proceedings of the National Academy of Sciences (1996); 93(8): 3636-3641.
Cooper, A. B., et al., "A unique function for cyclin D3 in early B cell development", Nature Immunology (2006); 7(5): 489-497.
Dientsmann, R., et al., "Picking the point of inhibition: a comparative review of PI3K/ AKT/mTOR pathway inhibitors", Molecular Cancer Therapeutics (2014); 13(5): 1021-1031.
Escobedo, J. A., et al., "A PDGF receptor domain essential for mitogenesis but not for many other responses to PDGF", Nature (1988); 335(6185): 85-87.
Fantl, W. J., et al., "Distinct phosphotyrosines on a growth factor receptor bind to specific molecules that mediate different signaling pathways", Cell (1992); 69(3): 413-423.
Fruman, D. A., et al., "Phosphoinositide kinases", Annual Review of Biochemistry (1998); 67(1): 481-507.
Guldberg, P., et al., "Disruption of the MMAC1/PTEN gene by deletion or mutation is a frequent event in malignant melanoma", Cancer Research (1997); 57(17): 3660-3663.
Hay, N., et al., "Upstream and downstream of mTOR", Genes & Development (2004); 18(16): 1926-1945.
Jacinto, E., et al., "Mammalian TOR complex 2 controls the actin cytoskeleton and is rapamycin insensitive", Nature Cell Biology (2004); 6(11): 1122-1128.
Kang, S., et al., "Phosphatidylinositol 3-kinase mutations identified in human cancer are oncogenic", Proceedings of the National Academy of Sciences (2005); 102(3): 802-807.
Kaplan, B., et al., "Strategies for the management of adverse events associated vvith mTOR inhibitors", Transplantation Reviews (2014); 28(3): 126-133.
Katso, R., et al., "Cellular function of phosphoinositide 3-kinases: implications for development, immunity, homeostasis, and cancer", Annual Review of Cell and Developmental Biology (2001); 17(1): 615-675.
Li, J., et al., "PTEN, a putative protein tyrosine phosphatase gene mutated in human brain, breast, and prostate cancer", Science (1997); 275(5308): 1943-1947.
Liaw, D., et al., "Germline mutations of the PTEN gene in Cowden disease, an inherited breast and thyroid cancer syndrome", Nature Genetics (1997); 16(1): 64-67.
Lipton, J. O., et al., "The neurology of mTOR", Neuron (2014); 84(2): 275-291.
Maehama, T., et al., "PTEN and myotubularin: novel phosphoinositide phosphatases", Annual Review of Biochemistry (2001); 70(1): 247-279.
Magaway, C., et al., "Targeting mTOR and Metabolism in Cancer: Lessons and Innovations", Cells (2019); 8(12): 1584; 51 pages.
Malumbres, M., "Mammalian Cells Cycle without the D-type Cyclin-Dependent Kinases Cdk4 and Cdk6", Cell (2004); 118(4): 493-504.
Mitra, A., et al., "Dual mTOR inhibition is required to prevent TGF-β-mediated fibrosis: implications for scleroderma", The Journal of Investigative Dermatology (2015); 135(11): 2873-2876.
Pallet, N., et al., "Adverse events associated with mTOR inhibitors", Expert Opinion on Drug Safety (2013); 12(2): 177-186.
Pópulo, H., et al., "The mTOR signalling pathway in human cancer." International Journal of Molecular Sciences (2012); 13(2): 1886-1918.
Risinger, J. I., et al., "PTEN/MMAC1 mutations in endometrial cancers", Cancer Research (1997); 57(21): 4736-4738.
Sabatini, D, M., et al., "RAFT1: a mammalian protein that binds to FKBP12 in a rapamycin-dependent fashion and is homologous to yeast TORs", Cell (1994); 78(1): 35-43.
Sabers, C. J., et al., "Isolation of a protein target of the FKBP12-rapamycin complex in mammalian cells (*)", Journal of Biological Chemistry (1995); 270(2): 815-822.
Samuels, Y., et al., "High frequency of mutations of the PIK3CA gene in human cancers", Science (2004); 304(5670): 554-554.
Samuels, Y., et al., "Mutant PIK3CA promotes cell growth and invasion of human cancer cells", Cancer Cell (2005); 7(6): 561-573.
Sicinska, E., et al. "Essential Role for Cyclin D3 in Granulocyte Colony-Stimulating Factor-Driven Expansion of Neutrophil Granulocytes", Molecular and Cellular Biology (2006); 26(21): 8052-8060.
Staal, S., et al. "Isolation of transforming murine leukemia viruses from mice with a high incidence of spontaneous lymphoma", Proceedings of the National Academy of Sciences of the United States of America (1977); 74(7): 3065-3067.
Stambolic, V., et al., "Negative regulation of PKB/Akt-dependent cell survival by the tumor suppressor PTEN", Cell (1998); 95(1): 29-39.
Stephens, L. R., et al., "The Gβγ sensitivity of a PI3K is dependent upon a tightly associated adaptor, p. 101", Cell (1997); 89(1): 105-114.
Suire, S., et al., "p84, a new Gβγ-activated regulatory subunit of the type IB phosphoinositide 3-kinase p110β", Current Biology (2005); 15(6): 566-570.
Sun, H., et al., "PTEN modulates cell cycle progression and cell survival by regulating phosphatidylinositol 3, 4, 5,-trisphosphate and Akt/protein kinase B signaling pathway", Proceedings of the National Academy of Sciences (1999); 96(11): 6199-6204.
Sun, M., et al., "AKT1/PKBα kinase is frequently elevated in human cancers and its constitutive activation is required for oncogenic transformation in NIH3T3 cells", The American Journal of Pathology (2001); 159(2): 431-437.
Vanhaesebroeck, B., et al., "Synthesis and function of 3-phosphorylated inositol lipids", Annual Review of Biochemistry (2001); 70(1): 535-602.
Wang, S., et al. "Selective inhibition of mTORC1 in tumor vessels increases antitumor immunity", JCI Insight (2020); 5(15): e139237; 17 pages.
Yin, Y., et al., "mTORC2 promotes type I insulin-like growth factor receptor and insulin receptor activation through the tyrosine kinase activity of mTOR", Cell research (2016); 26(1): 46-65.
Hanan, E. J., et al., "Discovery of GDC-0077 (inavolisib), a highly selective inhibitor and degrader of mutant PI3Ka", Journal of Medicinal Chemistry (2022); 65(24): 16589- 16621.
Nakatani, K., et al., "Up-regulation of Akt3 in estrogen receptor-deficient breast cancers and androgen-independent prostate cancer lines", Journal of Biological Chemistry (1999); 274(31): 21528-21532.

\* cited by examiner

METHODS OF TREATING BREAST CANCER WITH TETRAHYDRONAPHTHALENE DERIVATIVES AS ESTROGEN RECEPTOR DEGRADERS

CROSS REFERENCE TO RELATED APPLICATIONS

This application claims priority to, and the benefit of, U.S. Application No. 63/023,067, filed May 11, 2020, U.S. Application No. 62/942,663, filed Dec. 2, 2019, U.S. Application No. 62/924,653, filed Oct. 22, 2019, and U.S. Application No. 62/891,648, filed Aug. 26, 2019, the entirety of each of which is incorporated by reference herein.

FIELD OF THE DISCLOSURE

This application relates to treating breast cancer, including locally advanced or metastatic ER+, HER2− breast cancer, comprising administering a compound of Formula (I) to a subject in need of treatment.

BACKGROUND OF THE DISCLOSURE

In the United States (US), breast cancer is the second leading cause of cancer death in women, with approximately 41,000 women expected to die from breast cancer in 2018. While breast cancer is less common in men, men account for approximately 1% of all newly diagnosed cases, and almost 500 men are projected to die from their disease in 2018 (Seigel R. L. et al. Cancer Statistics, CA Cancer J Clin. 2018, 68(1); 7-30).

It is estimated that as of January 2017, approximately 155,000 women with metastatic breast cancer (mBC) were living in the US. It was also reported that the number of women living with mBC is increasing primarily because of improvements in treatment and the aging of the US population. The estimated number of women living with mBC increased by 17% from 2000 to 2010 and is projected to increase by 31% from 2010 to 2020 (Mariotto A. B. et al. "Estimation of the Number of Women Living with Metastatic Breast Cancer in the United States" Cancer Epidemiol. Biomarkers Prev. 2017, 26(6):809-815).

Treatment options for advanced breast cancer or mBC depend on many different factors, including whether the tumors express hormone receptors, i.e., estrogen receptor (ER) and/or progesterone receptor, or human epidermal growth factor receptor 2 (HER2). The standard of care for women with mBC is endocrine therapy, chemotherapy and/or targeted therapy alone or in combination. Patients with ER positive (ER+) and HER2 negative (HER2−) mBC are treated with endocrine therapy, sometimes in combination with targeted drugs such as CDK4/6 inhibitors (CDKi). In patients with aggressive disease or whose disease continues to progress on endocrine therapy, chemotherapy may be prescribed.

The current standard of care for women with ER+, HER2−, mBC is endocrine therapy+/−CDKi or mTOR inhibitor. Endocrine therapies include ovarian ablation or suppression (for pre-menopausal women), tamoxifen (a selection ER modulator), aromatase inhibitors, and fulvestrant (a SERD). Metastatic breast cancer remains incurable, and sequencing of endocrine therapies is the recommended approach for the treatment of ER+ breast cancer. The addition of targeted agents including CDKi and mTOR inhibitors to a backbone of endocrine therapy further improves patient outcomes.

Fulvestrant is considered the cornerstone component of ER-targeted endocrine regimens in the advanced disease setting, and works via an indirect mechanism of protein degradation, resulting in destabilization of the ER. Single-agent fulvestrant is dosed at 500 mg IM on days 1, 15, and 29 and once monthly thereafter. Efficacy of fulvestrant was established by comparison to the selective aromatase inhibitor anastrozole in 2 randomized, controlled clinical trials in postmenopausal women with locally advanced or mBC (Astra Zeneca Faslodex Full Prescribing Information, revised March 2019). All patients had progressed after previous therapy with an antiestrogen or progestin for breast cancer in the adjuvant or advanced disease setting. In both trials, eligible patients with measurable and/or evaluable disease were randomized to receive either fulvestrant 250 mg IM once a month (28 days+3 days) or anastrozole 1 mg orally once a day. Results of the trials, after a minimum follow-up duration of 14.6 months, ruled out inferiority of fulvestrant to anastrozole. There was no statistically significant difference in overall survival (OS) between the 2 treatment groups after a follow-up duration 2 years or more. A third study compared fulvestrant 500 mg dose to fulvestrant 250 mg dose. Results of this study after a minimum follow-up duration of 18 months showed that progression free survival (PFS) was statistically significantly superior with fulvestrant 500 mg vs fulvestrant 250 mg (6.5 months versus 5.4 months respectively). There was no statistically significant difference in OS between the 2 treatment groups (25.1 months for fulvestrant 500 mg and 22.8 months for fulvestrant 250 mg). Overall response rates were similar; the response rate for the 500 mg dose was 13.8%. (95% confidence intervals [CI] 9.7-18.8%) and for the 250 mg dose was 14.6% (CI 10.5-19.4%) (Astra Zeneca Faslodex Full Prescribing Information, revised March 2019).

SUMMARY OF THE DISCLOSURE

In one aspect, this application pertains to a method of treating breast cancer in a subject in need thereof, comprising administering to the subject a therapeutically effective amount of a compound of Formula (I),

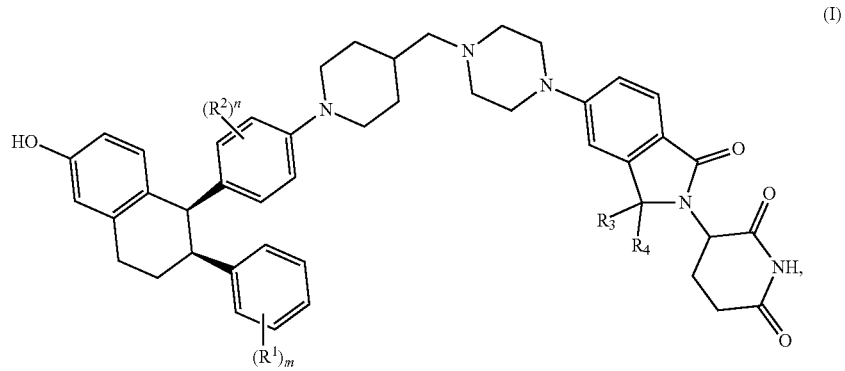

or a pharmaceutically acceptable salt, enantiomer, stereoisomer, solvate, polymorph, isotopic derivative, or prodrug thereof, wherein:
- each $R^1$ and each $R^2$ is independently selected from the group consisting of halo, $OR_5$, $N(R_5)(R_6)$, $NO_2$, CN, $SO_2(R_5)$, $C_1$-$C_6$ alkyl and $C_3$-$C_6$ cycloalkyl;
- $R_3$ and $R_4$ are either both hydrogen or, taken together with the carbon to which they are attached, form a carbonyl;
- each $R_5$ and each $R_6$ is independently selected from the group consisting of hydrogen, $C_1$-$C_6$ alkyl and $C_3$-$C_6$ cycloalkyl;
- m is 0, 1, 2, 3, 4, or 5; and
- n is 0, 1, 2, 3, or 4.

In one embodiment, the breast cancer is ER+, HER2−.

In one embodiment, the breast cancer is metastatic or locally advanced.

In one embodiment, each $R^1$ and each $R^2$ is independently selected from the group consisting of halo and $OR_5$.

In one embodiment, $R_3$ and $R_4$ are both hydrogen.

In one embodiment, $R_3$ and $R_4$, taken together with the carbon to which they are attached, form a carbonyl.

In one embodiment, m and n are each 0. In one embodiment, m and n are each 1. In one embodiment, one of m and n is 0 and the other is 1. For example, in one embodiment m is 0 and n is 1. In another embodiment, m is 0 and n is 1.

In one embodiment, the compound of Formula (I) is:

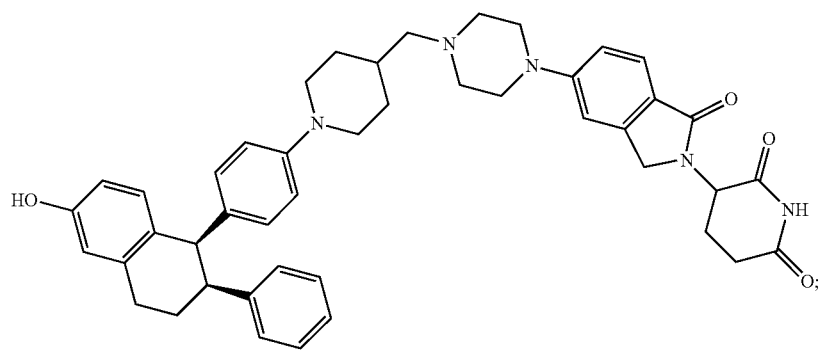

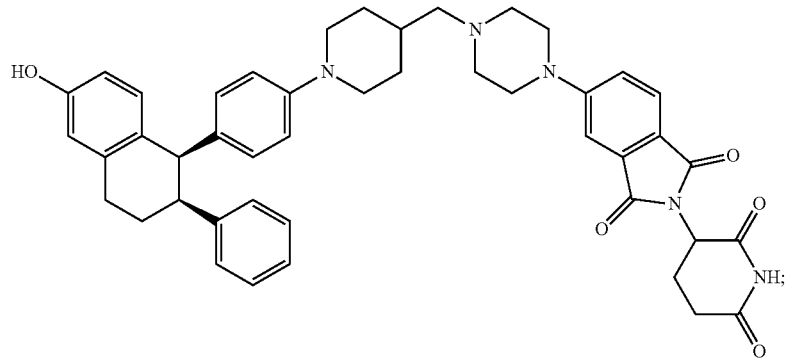 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

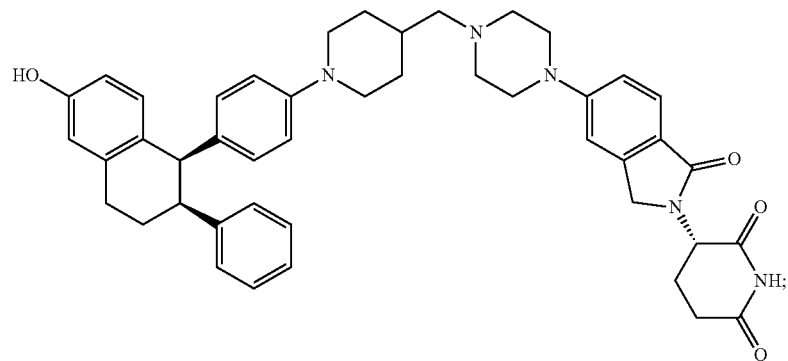 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]
(I-c)
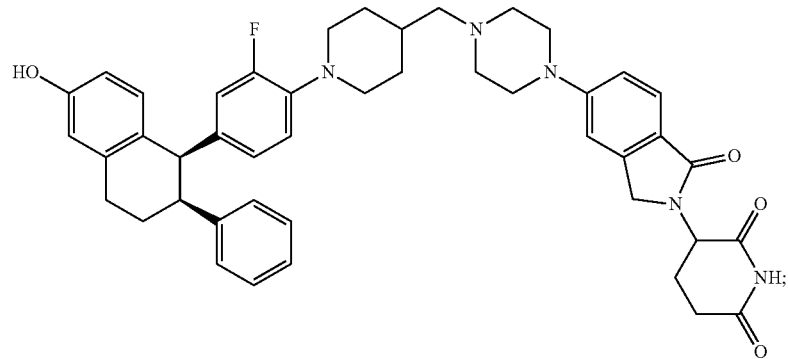 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]
(I-d)
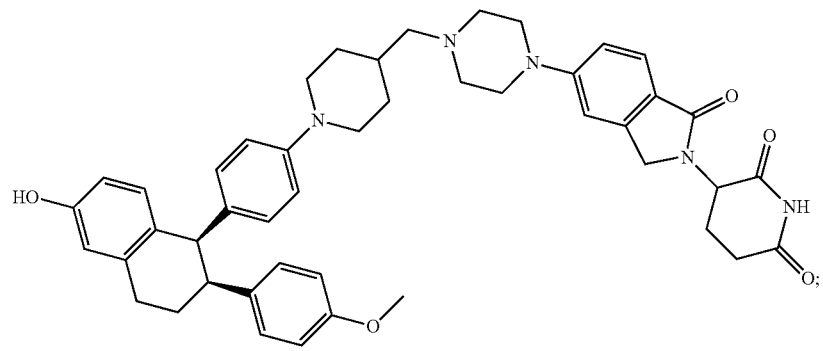
(I-e)
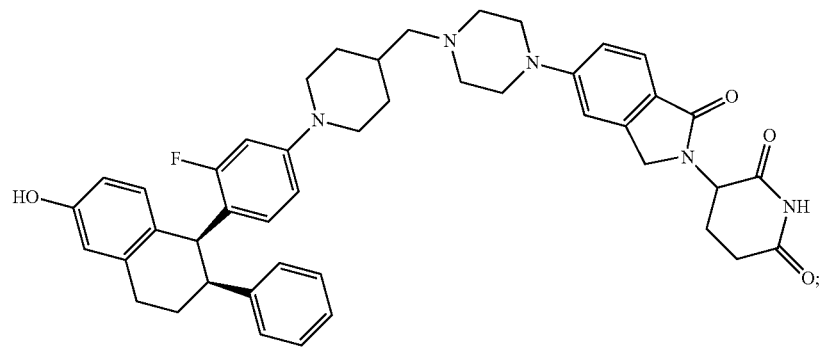
(I-f)

-continued

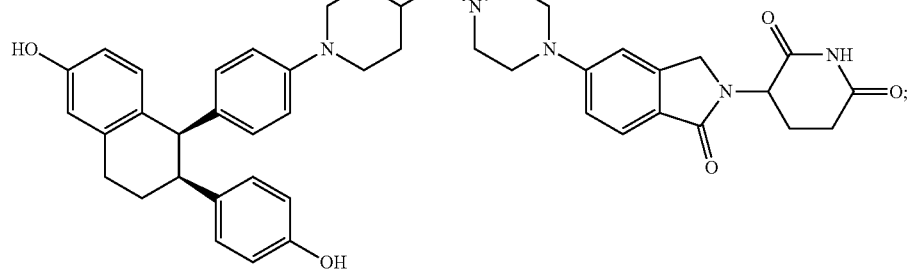
(I-g)

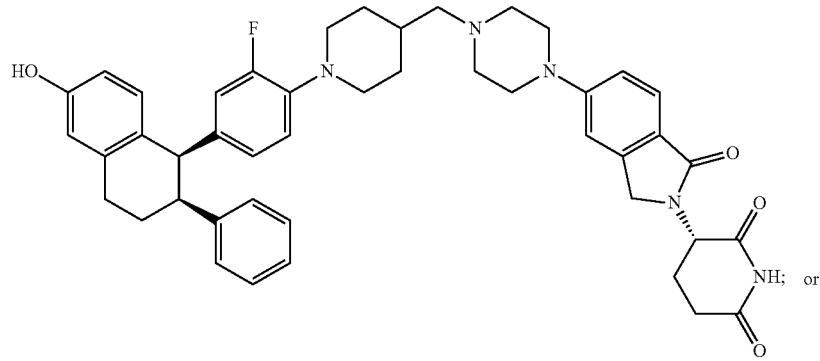
(I-h)

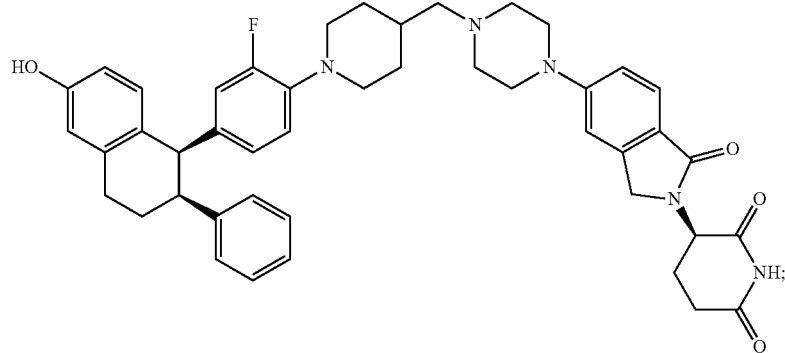
(I-i)

or a pharmaceutically acceptable salt, enantiomer, stereoisomer, solvate, polymorph, isotopic derivative, or prodrug of any of the foregoing.

In one embodiment, the method comprises administering to the subject a therapeutically effective amount of a compound of Formula (I) or a pharmaceutically acceptable salt, enantiomer, stereoisomer, solvate, polymorph, or isotopic derivative thereof.

In one embodiment, the compound of Formula (I) is administered orally to the subject.

In one embodiment, the therapeutically effective amount of the compound of Formula (I) is administered to the subject once a day, twice a day, three times a day, or four times a day. In one embodiment, the therapeutically effective amount of the compound of Formula (I) is administered to the subject once a day. In one embodiment, the therapeutically effective amount of the compound of Formula (I) is administered to the subject all at once or is administered in two, three, or four portions.

In one embodiment, the therapeutically effective amount of the compound of Formula (I) is about 3 mg, 5 mg, 10 mg, 15 mg, 20 mg, 25 mg, or 30 mg.

In one embodiment, the therapeutically effective amount of the compound of Formula (I) is about 10 mg to about 1000 mg.

In one embodiment, the therapeutically effective amount of the compound of Formula (I) is about 20 mg to about 700 mg.

In one embodiment, the therapeutically effective amount of the compound of Formula (I) is about 30 mg to about 500 mg.

In one embodiment, the therapeutically effective amount of the compound of Formula (I) is about 30 mg to about 120 mg.

In one embodiment, the therapeutically effective amount of the compound of Formula (I) is about 10 to about 40 mg, about 20 to about 50 mg, about 30 to about 60 mg, about 40 to about 70 mg, about 50 to about 80 mg, about 60 to about 90 mg, about 70 to about 100 mg, about 80 to about 110 mg, about 90 to about 120 mg, about 100 to about 130 mg, about 110 to about 140 mg, about 120 to about 150 mg, about 130 to about 160 mg, about 140 to about 170 mg, about 150 to about 180 mg, about 160 to about 190 mg, about 170 to about 200 mg, about 180 to about 210 mg, about 190 to about 220 mg, about 200 to about 230 mg, about 210 to about 240 mg, about 220 to about 250 mg, about 230 to about 260 mg, about 240 to about 270 mg, about 250 to about 280 mg, about 260 to about 290 mg, about 270 to about 300 mg, about 280 to about 310 mg, about 290 to about 320 mg, about 300 to about 330 mg, about 310 to about 340 mg, about 320 to about 350 mg, about 330 to about 360 mg, about 340 to about 370 mg, about 350 to about 380 mg, about 360 to about 390 mg, or about 370 to about 400 mg.

In one embodiment, the therapeutically effective amount of the compound of Formula (I) results in a mean day 15 $AUC_{TAU}$ of greater than about 3,500 ng*hr/mL, about 3,600 ng*hr/mL, about 3,700 ng*hr/mL, about 3,800 ng*hr/mL, about 3,900 ng*hr/mL, about 4,000 ng*hr/mL, about 4,100 ng*hr/mL, about 4,200 ng*hr/mL, about 4,300 ng*hr/mL, 4,400 ng*hr/mL, about 4,500 ng*hr/mL, about 4,600 ng*hr/mL, about 4,700 ng*hr/mL, about 4,800 ng*hr/mL, about 4,900 ng*hr/mL, or about 5,000 ng*hr/mL.

In one embodiment, the therapeutically effective amount of the compound of Formula (I) results in a mean day 15 $AUC_{TAU}$ of greater than about 3,500 ng*hr/mL and less than about 4,000 ng*hr/mL. In one embodiment, the therapeutically effective amount of the compound of Formula (I) results in a mean day 15 $AUC_{TAU}$ of greater than about 3,600 ng*hr/mL and less than about 4,100 ng*hr/mL. In one embodiment, the therapeutically effective amount of the compound of Formula (I) results in a mean day 15 $AUC_{TAU}$ of greater than about 3,700 ng*hr/mL and less than about 4,200 ng*hr/mL. In one embodiment, the therapeutically effective amount of the compound of Formula (I) results in a mean day 15 $AUC_{TAU}$ of greater than about 3,800 ng*hr/mL and less than about 4,300 ng*hr/mL. In one embodiment, the therapeutically effective amount of the compound of Formula (I) results in a mean day 15 $AUC_{TAU}$ of greater than about 3,900 ng*hr/mL and less than about 4,400 ng*hr/mL. In one embodiment, the therapeutically effective amount of the compound of Formula (I) results in a mean day 15 $AUC_{TAU}$ of greater than about 4,000 ng*hr/mL and less than about 4,500 ng*hr/mL. In one embodiment, the therapeutically effective amount of the compound of Formula (I) results in a mean day 15 $AUC_{TAU}$ of greater than about 4,100 ng*hr/mL and less than about 4,600 ng*hr/mL. In one embodiment, the therapeutically effective amount of the compound of Formula (I) results in a mean day 15 $AUC_{TAU}$ of greater than about 4,200 ng*hr/mL and less than about 4,700 ng*hr/mL. In one embodiment, the therapeutically effective amount of the compound of Formula (I) results in a mean day 15 $AUC_{TAU}$ of greater than about 4,300 ng*hr/mL and less than about 4,800 ng*hr/mL. In one embodiment, the therapeutically effective amount of the compound of Formula (I) results in a mean day 15 $AUC_{TAU}$ of greater than about 4,400 ng*hr/mL and less than about 4,900 ng*hr/mL. In one embodiment, the therapeutically effective amount of the compound of Formula (I) results in a mean day 15 $AUC_{TAU}$ of greater than about 4,500 ng*hr/mL and less than about 5,000 ng*hr/mL. In one embodiment, the therapeutically effective amount of the compound of Formula (I) results in a mean day 15 $AUC_{TAU}$ of greater than about 4,600 ng*hr/mL and less than about 5,100 ng*hr/mL. In one embodiment, the therapeutically effective amount of the compound of Formula (I) results in a mean day 15 $AUC_{TAU}$ of greater than about 4,700 ng*hr/mL and less than about 5,200 ng*hr/mL. In one embodiment, the therapeutically effective amount of the compound of Formula (I) results in a mean day 15 $AUC_{TAU}$ of greater than about 4,800 ng*hr/mL and less than about 5,300 ng*hr/mL. In one embodiment, the therapeutically effective amount of the compound of Formula (I) results in a mean day 15 $AUC_{TAU}$ of greater than about 4,900 ng*hr/mL and less than about 5,400 ng*hr/mL. In one embodiment, the therapeutically effective amount of the compound of Formula (I) results in a mean day 15 $AUC_{TAU}$ of greater than about 5,000 ng*hr/mL and less than about 5,500 ng*hr/mL.

In one embodiment, the therapeutically effective amount of the compound of Formula (I) results in a mean day 15 $AUC_{TAU}$ of greater than about 4,000 ng*hr/mL and less than about 4,200 ng*hr/mL. In one embodiment, the therapeutically effective amount of the compound of Formula (I) results in a mean day 15 $AUC_{TAU}$ of greater than about 3,900 ng*hr/mL and less than about 4,300 ng*hr/mL. In one embodiment, the therapeutically effective amount of the compound of Formula (I) results in a mean day 15 $AUC_{TAU}$ of greater than about 3,800 ng*hr/mL and less than about 4,400 ng*hr/mL. In one embodiment, the therapeutically effective amount of the compound of Formula (I) results in a mean day 15 $AUC_{TAU}$ of greater than about 3,700 ng*hr/mL and less than about 4,500 ng*hr/mL. In one embodiment, the therapeutically effective amount of the compound of Formula (I) results in a mean day 15 $AUC_{TAU}$ of greater than about 3,600 ng*hr/mL and less than about 4,600 ng*hr/mL.

In one embodiment, the therapeutically effective amount of the compound of Formula (I) results in a mean day 15 $C_{max}$ of greater than about 200 ng/mL, about 205 ng/mL, about 210 ng/mL, about 215 ng/mL, about 220 ng/mL, about 225 ng/mL, about 230 ng/mL, about 235 ng/mL, about 240 ng/mL, about 245 ng/mL, or about 250 ng/mL.

In one embodiment, the therapeutically effective amount of the compound of Formula (I) results in a mean day 15 $C_{max}$ of greater than about 200 ng/mL and less than about 220 ng/mL. In one embodiment, the therapeutically effective amount of the compound of Formula (I) results in a mean day 15 $C_{max}$ of greater than about 205 ng/mL and less than about 225 ng/mL. In one embodiment, the therapeutically effective amount of the compound of Formula (I) results in a mean day 15 $C_{max}$ of greater than about 210 ng/mL and less than about 230 ng/mL. In one embodiment, the therapeutically effective amount of the compound of Formula (I) results in a mean day 15 $C_{max}$ of greater than about 215 ng/mL and less than about 235 ng/mL. In one embodiment, the therapeutically effective amount of the compound of Formula (I) results in a mean day 15 $C_{max}$ of greater than about 220 ng/mL and less than about 240 ng/mL. In one embodiment, the therapeutically effective amount of the compound of Formula (I) results in a mean day 15 $C_{max}$ of greater than about 225 ng/mL and less than about 245 ng/mL. In one embodiment, the therapeutically effective amount of the compound of Formula (I) results in a mean day 15 $C_{max}$ of greater than about 230 ng/mL and less than about 250 ng/mL. In one embodiment, the therapeutically effective amount of the compound of Formula (I) results in a mean day 15 $C_{max}$ of greater than about 235 ng/mL and less than about 255 ng/mL. In one embodiment, the therapeutically effective amount of the compound of Formula (I) results in a mean day 15 $C_{max}$ of greater than about 240 ng/mL and less than about 260 ng/mL. In one embodiment, the therapeutically effective amount of the compound of Formula (I) results in a mean day 15 $C_{max}$ of greater than about 245 ng/mL and less than about 265 ng/mL. In one embodiment, the therapeutically effective amount of the compound of Formula (I) results in a mean day 15 $C_{max}$ of greater than about 250 ng/mL and less than about 270 ng/mL.

In one embodiment, the therapeutically effective amount of the compound of Formula (I) results in a mean day 15 $C_{max}$ of greater than about 214 ng/mL and less than about 236 ng/mL. In one embodiment, the therapeutically effective amount of the compound of Formula (I) results in a mean day 15 $C_{max}$ of greater than about 213 ng/mL and less than about 237 ng/mL. In one embodiment, the therapeutically effective amount of the compound of Formula (I) results in a mean day 15 $C_{max}$ of greater than about 212 ng/mL and less than about 238 ng/mL. In one embodiment, the therapeutically effective amount of the compound of Formula (I) results in a mean day 15 $C_{max}$ of greater than about 211 ng/mL and less than about 239 ng/mL. In one embodiment, the therapeutically effective amount of the compound of Formula (I) results in a mean day 15 $C_{max}$ of greater than about 210 ng/mL and less than about 240 ng/mL. In one embodiment, the therapeutically effective amount of the compound of Formula (I) results in a mean day 15 $C_{max}$ of greater than about 205 ng/mL and less than about 245 ng/mL. In one embodiment, the therapeutically effective amount of the compound of Formula (I) results in a mean day 15 $C_{max}$ of greater than about 200 ng/mL and less than about 250 ng/mL.

In one embodiment, the therapeutically effective amount of the compound of Formula (I) results in a mean day 15 $C_{max}$ of greater than about 223 ng/mL and less than about 225 ng/mL. In one embodiment, the therapeutically effective amount of the compound of Formula (I) results in a mean day 15 $C_{max}$ of greater than about 222 ng/mL and less than about 226 ng/mL. In one embodiment, the therapeutically effective amount of the compound of Formula (I) results in a mean day 15 $C_{max}$ of greater than about 221 ng/mL and less than about 227 ng/mL. In one embodiment, the therapeutically effective amount of the compound of Formula (I) results in a mean day 15 $C_{max}$ of greater than about 220 ng/mL and less than about 228 ng/mL. In one embodiment, the therapeutically effective amount of the compound of Formula (I) results in a mean day 15 $C_{max}$ of greater than about 219 ng/mL and less than about 229 ng/mL. In one embodiment, the therapeutically effective amount of the compound of Formula (I) results in a mean day 15 $C_{max}$ of greater than about 218 ng/mL and less than about 230 ng/mL. In one embodiment, the therapeutically effective amount of the compound of Formula (I) results in a mean day 15 $C_{max}$ of greater than about 217 ng/mL and less than about 231 ng/mL. In one embodiment, the therapeutically effective amount of the compound of Formula (I) results in a mean day 15 $C_{max}$ of greater than about 216 ng/mL and less than about 232 ng/mL. In one embodiment, the therapeutically effective amount of the compound of Formula (I) results in a mean day 15 $C_{max}$ of greater than about 215 ng/mL and less than about 233 ng/mL. In one embodiment, the therapeutically effective amount of the compound of Formula (I) results in a mean day 15 $C_{max}$ of greater than about 214 ng/mL and less than about 234 ng/mL.

In one embodiment, the compound of Formula (I) is formulated as a tablet. In one embodiment, the tablet comprises a compound of Formula (I) and, optionally, one or more of the following: emulsifier; surfactant; binder; disintegrant; glidant; and lubricant. In one embodiment, the emulsifier is hypromellose. In one embodiment, the surfactant is Vitamin E polyethylene glycol succinate. In one embodiment, the binder is microcrystalline cellulose or lactose monohydrate. In one embodiment, the disintegrant is croscarmellose sodium. In one embodiment, the glidant is silicon dioxide. In one embodiment, the lubricant is sodium stearyl fumarate. In one embodiment, the subject in need of treatment is in a fed state. In one embodiment, the subject in need of treatment is in a fasted state.

In one aspect, this application pertains to a method of treating breast cancer in a subject in need thereof, comprising administering to the subject a therapeutically effective amount of a compound of Formula (I) as defined herein, further comprising the administration of a therapeutically effective amount of a CDK4/6 inhibitor to the subject in need thereof. In one embodiment, the CDK4/6 inhibitor is SHR6390, trilaciclib, lerociclib, AT7519M, dinaciclib, ribociclib, abemaciclib, or palbociclib. In one embodiment, the CDK4/6 inhibitor is palbociclib.

In one embodiment, for the method of treating breast cancer in a subject in need thereof, comprising administering to the subject a therapeutically effective amount of a compound of Formula (I) and further comprising the administration of a therapeutically effective amount of palbociclib, the therapeutically effective amount of palbociclib is administered to the subject once a day. In one embodiment, the therapeutically effective amount of palbociclib is 60 mg, 75 mg, 100 mg, or 125 mg. In one embodiment, the palbociclib is administered once daily for up to 21 consecutive days, followed by up to 7 consecutive days off treatment, wherein the cycle of treatment with palbociclib followed by off treatment is repeated one, two, three, four, five, or more times. In one embodiment, the compound of formula (I) is administered once daily for 21 up to consecutive days, followed by up to 7 consecutive days off treatment, wherein the cycle of treatment with the compound of formula (I) followed by off treatment is repeated one, two, three, four, five, or more times. In one embodiment, the administration of the compound of Formula (I) and palbociclib to the subject in need thereof occurs when the subject is in a fed state. In one embodiment, the administration of the compound of Formula (I) and palbociclib to the subject in need thereof occurs when the subject is in a fasted state.

In one aspect, this application pertains to a method of treating metastatic breast cancer in a subject in need thereof, comprising once a day, oral administration of a therapeutically effective amount of the compound of Formula (I), or a pharmaceutically acceptable salt, enantiomer, stereoisomer, solvate, polymorph, isotopic derivative, or prodrug thereof, wherein the compound of Formula (I), is selected from the group consisting of:

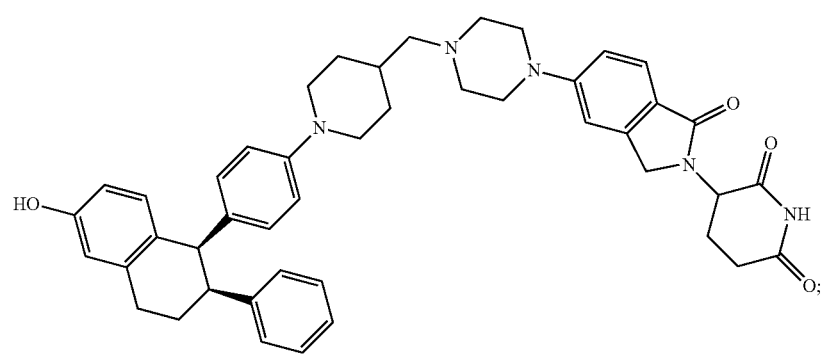

(I-a)

-continued
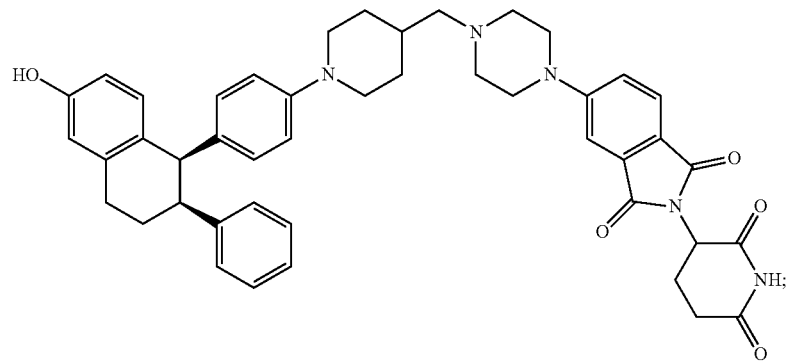
(I-b)
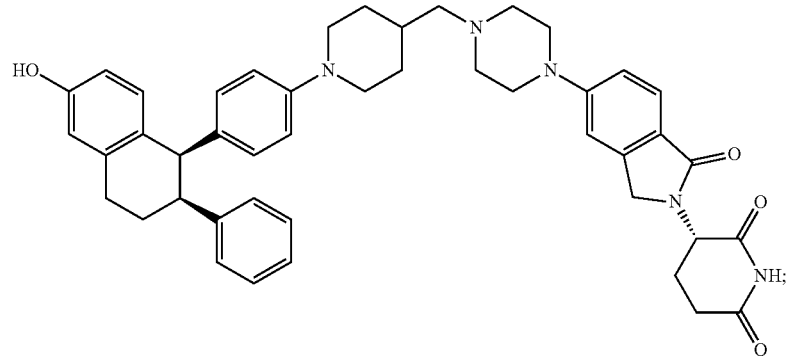 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]
(I-c)
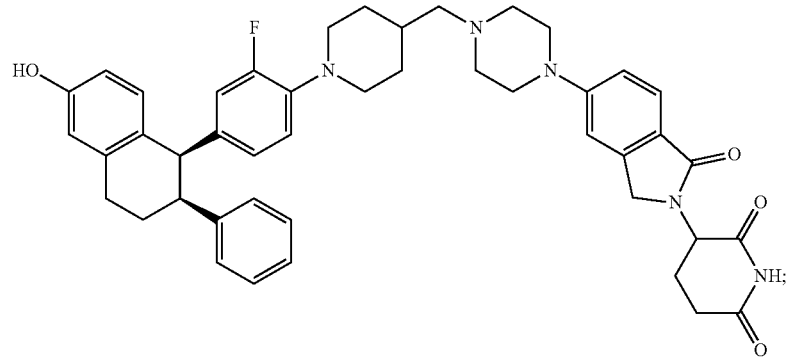
(I-d)
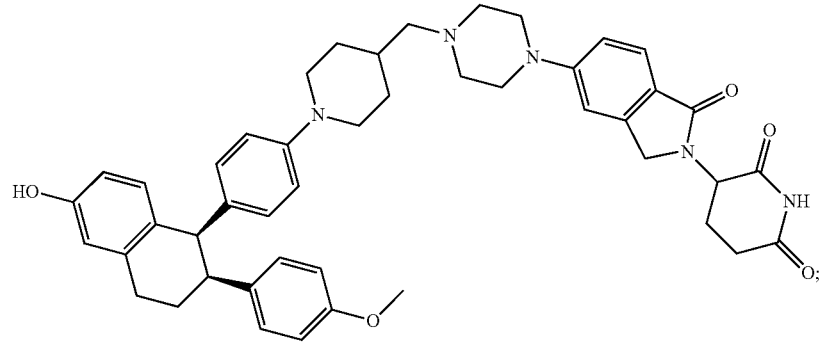
(I-e)

-continued

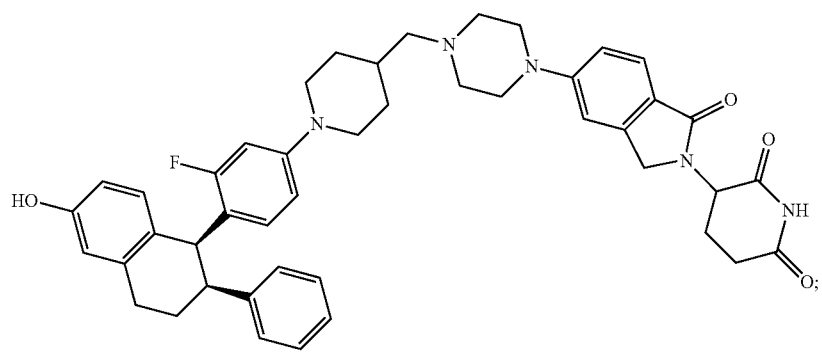
(I-f)

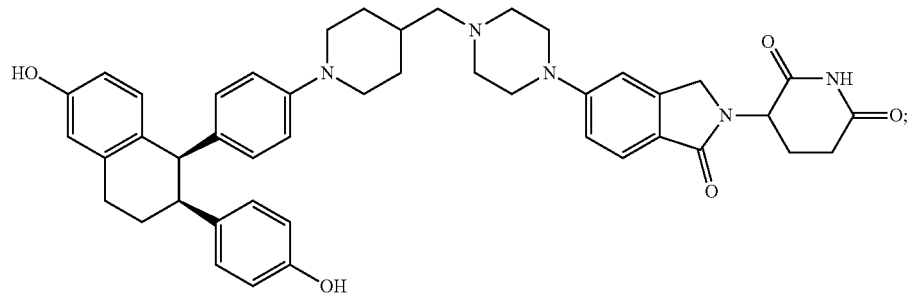
(I-g)

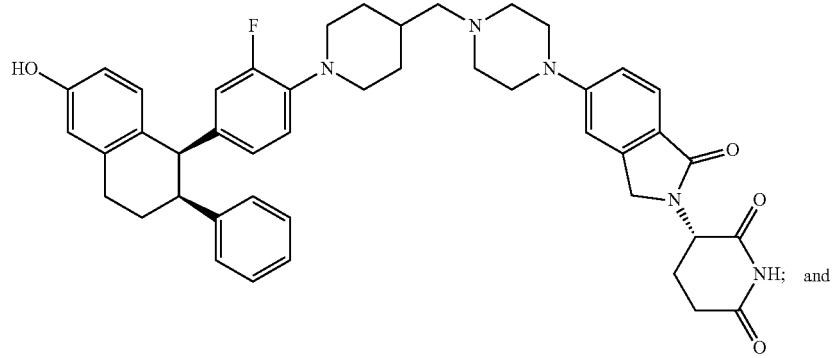
(I-h)

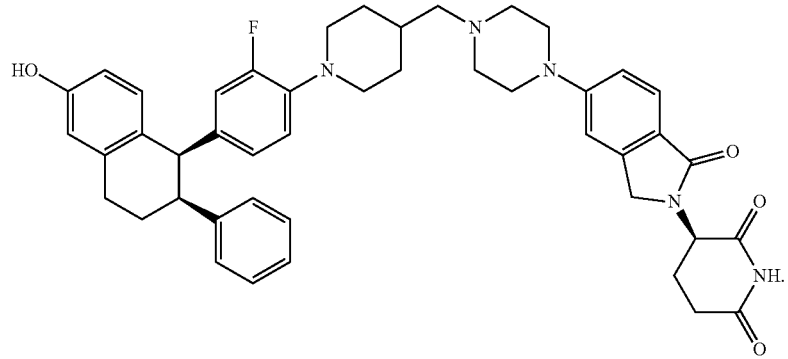
(I-i)

In one embodiment, the therapeutically effective amount of the compound of Formula (I) is administered to the subject all at once or is administered in two, three, or four portions.

In one embodiment, the therapeutically effective amount of the compound of Formula (I) is about 30 mg to about 1000 mg.

In one embodiment, the therapeutically effective amount of the compound of Formula (I) is about 10 to about 40 mg, about 20 to about 50 mg, about 30 to about 60 mg, about 40 to about 70 mg, about 50 to about 80 mg, about 60 to about 90 mg, about 70 to about 100 mg, about 80 to about 110 mg, about 90 to about 120 mg, about 100 to about 130 mg, about 110 to about 140 mg, about 120 to about 150 mg, about 130 to about 160 mg, about 140 to about 170 mg, about 150 to about 180 mg, about 160 to about 190 mg, about 170 to about 200 mg, about 180 to about 210 mg, about 190 to about 220 mg, about 200 to about 230 mg, about 210 to about 240 mg, about 220 to about 250 mg, about 230 to about 260 mg, about 240 to about 270 mg, about 250 to about 280 mg, about 260 to about 290 mg, about 270 to about 300 mg, about 280 to about 310 mg, about 290 to about 320 mg, about 300 to about 330 mg, about 310 to about 340 mg, about 320 to about 350 mg, about 330 to about 360 mg, about 340 to about 370 mg, about 350 to about 380 mg, about 360 to about 390 mg, or about 370 to about 400 mg.

In one embodiment, the compound of Formula (I) is formulated as a tablet.

In one aspect, this application pertains to a method of treating breast cancer in a subject in need thereof, comprising administering to the subject a therapeutically effective amount of a compound of Formula (I), wherein the compound of Formula (I) is a compound of Formula (I-a), Formula (I-b), Formula (I-c), Formula (I-d), Formula (I-e), Formula (I-f), Formula (I-g), Formula (I-h), Formula (I-i), or a pharmaceutically acceptable salt, enantiomer, stereoisomer, solvate, polymorph, isotopic derivative, or prodrug thereof, further comprising the administration of a therapeutically effective amount of a CDK4/6 inhibitor to the subject in need thereof. In one embodiment, the CDK4/6 inhibitor is SHR6390, trilaciclib, lerociclib, AT7519M, dinaciclib, ribociclib, abemaciclib, or palbociclib. In one embodiment, the CDK4/6 inhibitor is palbociclib.

In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered at the same time as the administration of a compound of Formula (I-a), Formula (I-b), Formula (I-c), Formula (I-d), Formula (I-e), Formula (I-f), Formula (I-g), Formula (I-h), or Formula (I-i). In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered prior to the administration of a compound of Formula (I-a), Formula (I-b), Formula (I-c), Formula (I-d), Formula (I-e), Formula (I-f), Formula (I-g), Formula (I-h), or Formula (I-i). In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered after the administration of a compound of Formula (I-a), Formula (I-b), Formula (I-c), Formula (I-d), Formula (I-e), Formula (I-f), Formula (I-g), Formula (I-h), or Formula (I-i). In some embodiments for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the administration of a compound of Formula (I-a), Formula (I-b), Formula (I-c), Formula (I-d), Formula (I-e), Formula (I-f), Formula (I-g), Formula (I-h), or Formula (I-i) and the administration of palbociclib are separated in time such that the two compounds, and their respective excipients (if present), do not mix in the subject's stomach.

In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered at least 5, at least 10, at least 15, at least 20, at least 25, or at least 30 minutes prior to the administration of a compound of Formula (I-a), Formula (I-b), Formula (I-c), Formula (I-d), Formula (I-e), Formula (I-f), Formula (I-g), Formula (I-h), or Formula (I-i). In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered at least 30 minutes prior to the administration of a compound of Formula (I-a), Formula (I-b), Formula (I-c), Formula (I-d), Formula (I-e), Formula (I-f), Formula (I-g), Formula (I-h), or Formula (I-i). In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered between 30 and 60 minutes prior to the administration of a compound of Formula (I-a), Formula (I-b), Formula (I-c), Formula (I-d), Formula (I-e), Formula (I-f), Formula (I-g), Formula (I-h), or Formula (I-i).

In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered at least 5, at least 10, at least 15, at least 20, at least 25, or at least 30 minutes after the administration of a compound of Formula (I-a), Formula (I-b), Formula (I-c), Formula (I-d), Formula (I-e), Formula (I-f), Formula (I-g), Formula (I-h), or Formula (I-i). In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered at least 30 minutes after the administration of a compound of Formula (I-a), Formula (I-b), Formula (I-c), Formula (I-d), Formula (I-e), Formula (I-f), Formula (I-g), Formula (I-h), or Formula (I-i). In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered between 30 and 60 minutes after the administration of a compound of Formula (I-a), Formula (I-b), Formula (I-c), Formula (I-d), Formula (I-e), Formula (I-f), Formula (I-g), Formula (I-h), or Formula (I-i).

In one embodiment, for the method of treating breast cancer in a subject in need thereof, comprising administering to the subject a therapeutically effective amount of a compound of Formula (I-a), Formula (I-b), Formula (I-c), Formula (I-d), Formula (I-e), Formula (I-f), Formula (I-g), Formula (I-h), or Formula (I-i), and further comprising the administration of a therapeutically effective amount of palbociclib, the therapeutically effective amount of palbociclib is administered to the subject once a day. In one embodiment, the therapeutically effective amount of palbociclib is 60 mg, 75 mg, 100 mg, or 125 mg. In one embodiment, the palbociclib is administered once daily for up to 21 consecutive days, followed by up to 7 consecutive days off treatment, wherein the cycle of treatment with palbociclib followed by off treatment is repeated one, two, three, four, five, or more times. In one embodiment, the compound of Formula (I-a), Formula (I-b), Formula (I-c), Formula (I-d), Formula (I-e), Formula (I-f), Formula (I-g), Formula (I-h), or Formula (I-i) is administered once daily for up to 21 consecutive days, followed by up to 7 consecutive days off treatment, wherein the cycle of treatment with the compound of Formula (I-a), Formula (I-b), Formula (I-c), Formula (I-d), Formula (I-e), Formula (I-f), Formula (I-g), Formula (I-h), or Formula (I-i) followed by off treatment is repeated one, two, three, four, five, or more times. In one embodiment, the administration of the compound of Formula (I-a), Formula (I-b), Formula (I-c), Formula (I-d), Formula (I-e), Formula (I-f), Formula (I-g), Formula (I-h), or Formula (I-i) and palbociclib to the subject in need thereof occurs when the subject is in a fed state. In one embodiment, the administration of the compound of Formula (I-a), Formula (I-b), Formula (I-c), Formula (I-d), Formula (I-e), Formula (I-f), Formula (I-g), Formula (I-h), or Formula (I-i) and palbociclib to the subject in need thereof occurs when the subject is in a fasted state.

In one aspect, this application pertains to a method of treating breast cancer in a subject in need thereof, comprising: (i) once a day, oral administration of a therapeutically effective amount of a compound of Formula (I-c), or a pharmaceutically acceptable salt, enantiomer, stereoisomer, solvate, polymorph, isotopic derivative, or prodrug thereof, and (ii) once a day, oral administration of palbociclib. In one aspect, this application pertains to a method of treating breast cancer in a subject in need thereof, comprising: (i) once a day, oral administration of a therapeutically effective amount of a compound of Formula (I-c) and (ii) once a day, oral administration of palbociclib. In one embodiment, the therapeutically effective amount of the compound of Formula (I-c) is about 30 mg to about 1000 mg. In one embodiment, the therapeutically effective amount of palbociclib is 60 mg, 75 mg, 100 mg, or 125 mg. In one embodiment, the palbociclib is administered once daily for up to 21 consecutive days, followed by up to 7 consecutive days off treatment, wherein the cycle of treatment with palbociclib followed by off treatment is repeated one, two, three, four, five, or more times. In one embodiment, the compound of formula (I-c) is administered once daily for up to 21 consecutive days, followed by up to 7 consecutive days off treatment, wherein the cycle of treatment with the compound of formula (I-c) followed by off treatment is repeated one, two, three, four, five, or more times. In one embodiment, the administration of the compound of Formula (I-c) and palbociclib to the subject in need thereof occurs when the subject is in a fed state. In one embodiment, the administration of the compound of Formula (I-c) and palbociclib to the subject in need thereof occurs when the subject is in a fasted state.

In one embodiment, for the method of treating breast cancer in a subject in need thereof, comprising once a day, oral administration of a therapeutically effective amount of a compound of Formula (I-c) and further once a day, oral administration of palbociclib, the administration of a compound of Formula (I-c) and the administration of palbociclib are separated in time such that the two compounds, and their respective excipients (if present), do not mix in the subject's stomach. In one embodiment, for the method of treating breast cancer in a subject in need thereof, comprising once a day, oral administration of a therapeutically effective amount of a compound of Formula (I-c) and further once a day, oral administration of palbociclib, the palbociclib is administered prior to the administration of a compound of Formula (I-c). In one embodiment, for the method of treating breast cancer in a subject in need thereof, comprising once a day, oral administration of a therapeutically effective amount of a compound of Formula (I-c) and further once a day, oral administration of palbociclib, the palbociclib is administered at least 5, at least 10, at least 15, at least 20, at least 25, or at least 30 minutes prior to the administration of a compound of Formula (I-c). In one embodiment, for the method of treating breast cancer in a subject in need thereof, comprising once a day, oral administration of a therapeutically effective amount of a compound of Formula (I-c) and further once a day, oral administration of palbociclib, the palbociclib is administered at least 30 minutes prior to the administration of a compound of Formula (I-c). In one embodiment, for the method of treating breast cancer in a subject in need thereof, comprising once a day, oral administration of a therapeutically effective amount of a compound of Formula (I-c) and further once a day, oral admin-

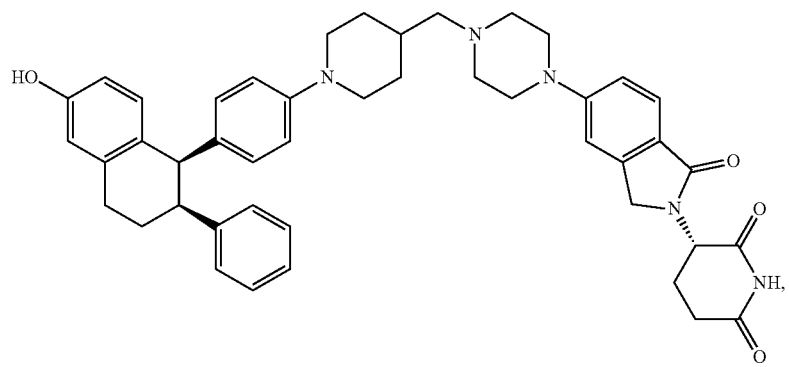

istration of palbociclib, the palbociclib is administered between 30 and 60 minutes prior to the administration of a compound of Formula (I-c).

In one embodiment, for the method of treating breast cancer in a subject in need thereof, comprising once a day, oral administration of a therapeutically effective amount of a compound of Formula (I-c) and further once a day, oral administration of palbociclib, the palbociclib is administered after the administration of a compound of Formula (I-c). In one embodiment, for the method of treating breast cancer in a subject in need thereof, comprising once a day, oral administration of a therapeutically effective amount of a compound of Formula (I-c) and further once a day, oral administration of palbociclib, the palbociclib is administered at least 5, at least 10, at least 15, at least 20, at least 25, or at least 30 minutes after the administration of a compound of Formula (I-c). In one embodiment, for the method of treating breast cancer in a subject in need thereof, comprising once a day, oral administration of a therapeutically effective amount of a compound of Formula (I-c) and further once a day, oral administration of palbociclib, the palbociclib is administered at least 30 minutes after the administration of a compound of Formula (I-c). In one embodiment, for the method of treating breast cancer in a subject in need thereof, comprising once a day, oral administration of a therapeutically effective amount of a compound of Formula (I-c) and further once a day, oral administration of palbociclib, the palbociclib is administered between 30 and 60 minutes after the administration of a compound of Formula (I-c).

In one aspect, this application pertains to a method for selective estrogen receptor degradation in a patient comprising: (i) once a day, oral administration of a therapeutically effective amount of a compound of Formula (I-c),

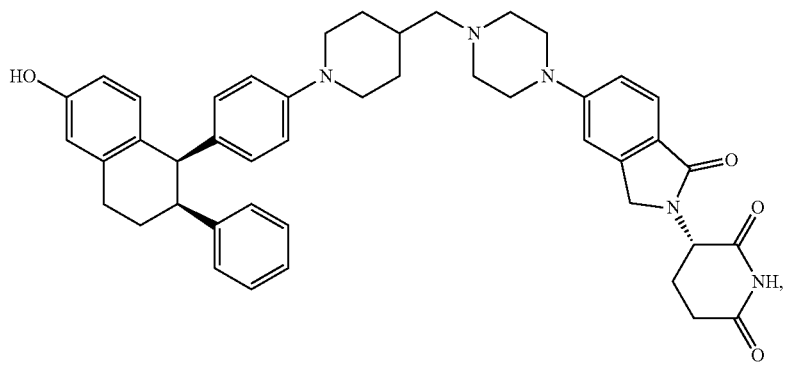

or a pharmaceutically acceptable salt, enantiomer, stereoisomer, solvate, polymorph, isotopic derivative, or prodrug thereof, and (ii) once a day, oral administration of palbociclib.

In one aspect, this application pertains to a method for inhibiting a cyclin-dependent kinase in a subject in need thereof comprising: (i) once a day, oral administration of a therapeutically effective amount of a compound of Formula (I-c),

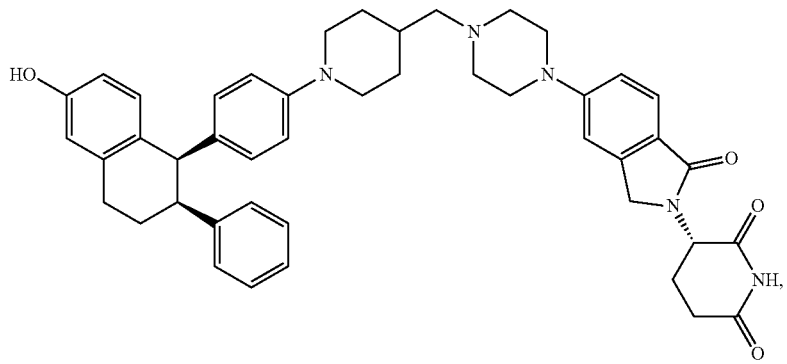

or a pharmaceutically acceptable salt, enantiomer, stereoisomer, solvate, polymorph, isotopic derivative, or prodrug thereof, and (ii) once a day, oral administration of palbociclib.

In one aspect, this application pertains to a kit comprising:
a compound of Formula (I-c),

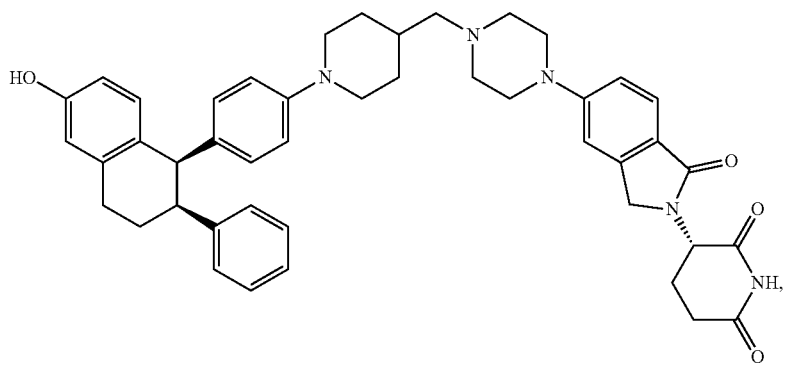 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

palbociclib, and instructions for use.

In one aspect, this application pertains to a liquid composition comprising a surfactant, a solvent, and a compound of Formula (I-c),

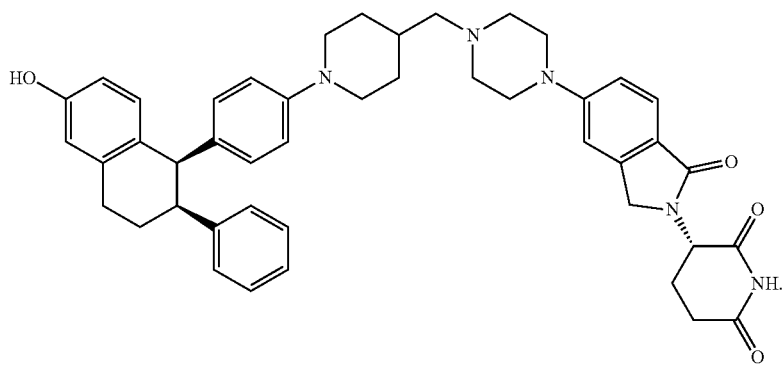

In some embodiments, the surfactant is a sorbitan derivative. In some embodiments, the surfactant is Tween 80. In some embodiments, the solvent is a low molecular weight polyethylene glycol (PEG). In some embodiments, the solvent is polyethylene glycol (PEG)-400.

In one aspect, this application pertains to method of making a liquid composition comprising a surfactant, a solvent, and a compound of Formula (I-c):

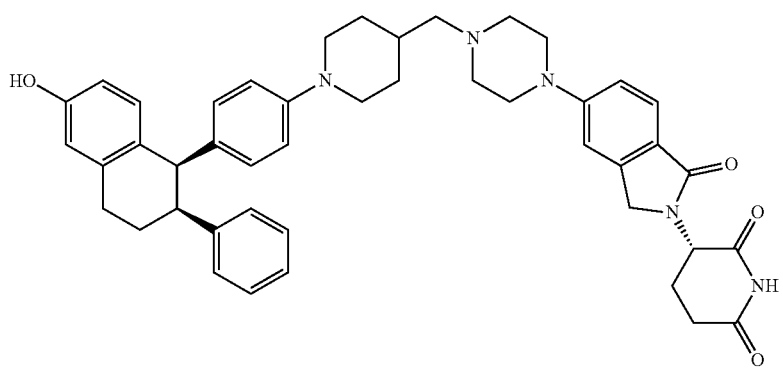 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

comprising the step of adding the solvent to a pre-aliquoted volume of the surfactant. In some embodiments, the method further comprises the step of adding a compound of Formula (I-c) to a mixture of the solvent and the surfactant. In some embodiments, the surfactant is a sorbitan derivative. In some embodiments, the surfactant is Tween 80. In some embodiments, the solvent is a low molecular weight polyethylene glycol (PEG). In some embodiments, the solvent is polyethylene glycol (PEG)-400.

DETAILED DESCRIPTION

Definitions

Figure 1:
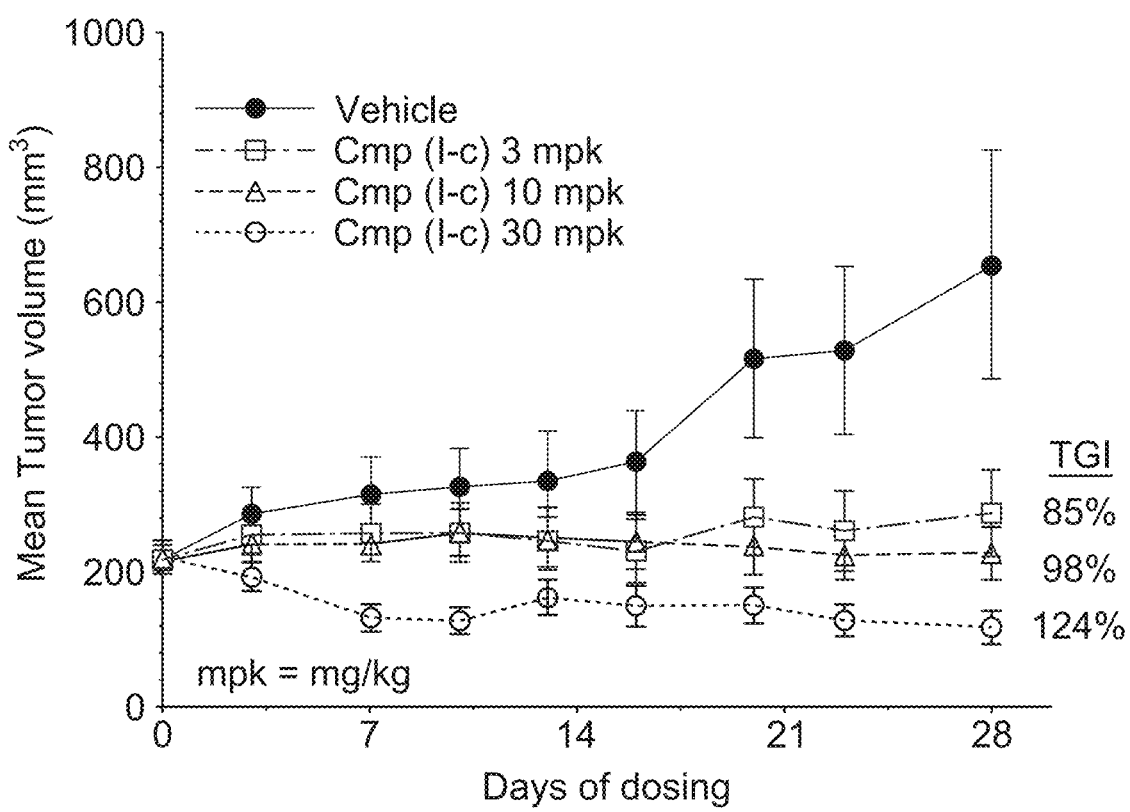
FIG. 1 shows the results of tumor growth inhibition experiments (mean tumor volume (mm$^3$) vs. time) associated with oral, once daily administration of Compound (I-c) at doses of 3 mg/kg, 10 mg/kg, and 30 mg/kg compared to vehicle. At doses of 3 mg/kg, 10 mg/kg, and 30 mg/kg of Compound (I-c), tumor growth inhibition (TGI) of 85%, 98%, and 124%, respectively, was observed compared to a control group in a MCF7 xenograft model.

"H" refers to hydrogen.

Halogen or "halo" refers to fluorine (F), chlorine (Cl), bromine (Br), or iodine (I).

"$C_1$-$C_6$ alkyl" refers to a straight or branched chain saturated hydrocarbon containing 1-6 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"$C_3$-$C_6$ cycloalkyl" means monocyclic saturated carbon rings containing 3-6 carbon atoms, i.e., a cyclopropyl, cyclobutyl, cyclopentyl, or cyclohexyl moiety.

"Pharmaceutically acceptable salt" as used herein with respect to a compound of Formula (I), means a salt form of a compound of Formula (I) as well as hydrates of the salt form with one or more water molecules present. Such salt and hydrated forms retain the biological activity of a compound of Formula (I) and are not biologically or otherwise undesirable, i.e., exhibit minimal, if any, toxicological effects. Representative "pharmaceutically acceptable salts" include, e.g., water-soluble and water-insoluble salts, such as the acetate, amsonate (4,4-diaminostilbene-2,2-di sulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "isomer" refers to salts and/or compounds that have the same composition and molecular weight but differ in physical and/or chemical properties. The structural difference may be in constitution (geometric isomers) or in the ability to rotate the plane of polarized light (stereoisomers). With regard to stereoisomers, the salts of a compound of Formula (I) may have one or more asymmetric carbon atom and may occur as racemates, racemic mixtures and as individual enantiomers or diastereomers.

The compounds of Formula (I) may exist in unsolvated as well as solvated forms such as, for example, hydrates.

"Solvate" means a solvent addition form that contains either a stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the invention.

When a compound is crystallized from a solution or slurry, it can be crystallized in a different arrangement lattice of spaces (this property is called "polymorphism") to form crystals with different crystalline forms, each of which is known as "polymorphs". "Polymorph", as used herein, refers to a crystal form of a compound of Formula (I), where the molecules are localized in the three-dimensional lattice sites. Different polymorphs of the compound of Formula (I) may be different from each other in one or more physical properties, such as solubility and dissolution rate, true specific gravity, crystal form, accumulation mode, flowability and/or solid state stability, etc.

"Isotopic derivative", as referred to herein, relates to a compound of Formula (I) that is isotopically enriched or labelled (with respect to one or more atoms of the compound) with one or more stable isotopes. Thus, in this application, the compounds of Formula (I) include, for example, compounds that are isotopically enriched or labelled with one or more atoms, such as deuterium ($^2$H or D) or carbon-13 ($^{13}$C).

The term "pharmaceutically acceptable prodrugs" as used herein refers to those prodrugs of the compounds of Formula (I) which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention.

"Prodrug", as used herein means a compound which is convertible in vivo by metabolic means (e.g., by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 1 13-191 (1991); Bundgaard, et al., Journal of Drug Delivery Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa &

Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. Combinations of substituents and variables envisioned by this invention are only those that result in the formation of stable compounds.

Metastatic breast cancer, or metastases, refers to breast cancer that has spread beyond the breast and nearby lymph nodes to other parts of the body, e.g., bones, liver, lungs, brain. (https://www.cancer.org/cancer/breast-cancer.)

Locally advanced breast cancer (LABC) is defined by the U.S. National Comprehensive Cancer Network as a subset of breast cancer characterized by the most advanced breast tumors in the absence of distant metastasis, wherein the tumors are more than 5 cm in size with regional lymphadenopathy; tumors of any size with direct extension to the chest wall or skin, or both (including ulcer or satellite nodules), regardless of regional lymphadenopathy; presence of regional lymphadenopathy (clinically fixed or matted axillary lymph nodes, or any of infraclavicular, supraclavicular, or internal mammary lymphadenopathy) regardless of tumor stage. (Garg et al. Curr Oncol. 2015 October; 22(5): e409-e410; National Comprehensive Cancer Network NCCN Clinical Practice Guidelines in Oncology: Breast Cancer. Fort Washington, PA: NCCN; 2015. Ver. 2.2015.)

ER+, estrogen receptor positive, as used herein, refers to breast cancer cells that have a receptor protein that binds the hormone estrogen. Cancer cells that are ER+ may need estrogen to grow, and may stop growing or die when treated with substances that block the binding and actions of estrogen. (https://www.cancer.gov/publications/dictionaries/cancer-terms/def/44404.)

HER2−, human epidermal growth factor receptor 2, as used herein, refers to breast cancer cells that does not have a large amount of a protein called HER2 on their surface. In normal cells, HER2 helps to control cell growth. Cancer cells that are HER2− may grow more slowly and are less likely to recur or spread to other parts of the body than cancer cells that have a large amount of HER2 on their surface. (https://www.cancer.gov/publications/dictionaries/cancer-terms/def/her2-negative.)

As used herein, "treating" describes the management and care of a subject for the purpose of combating a disease, condition, or disorder and includes decreasing or alleviating the symptoms or complications, or eliminating the disease, condition or disorder.

As used herein, "preventing" describes stopping the onset of the symptoms or complications of the disease, condition or disorder.

"Administration" refers to introducing an agent, such as a compound of Formula (I) into a subject. The related terms "administering" and "administration of" (and grammatical equivalents) refer both to direct administration, which may be administration to a subject by a medical professional or by self-administration by the subject, and/or to indirect administration, which may be the act of prescribing a drug. For example, a physician who instructs a patient to self-administer a drug and/or provides a patient with a prescription for a drug is administering the drug to the patient.

"Therapeutically effective amount", as used herein means an amount of the free base of a compound of Formula (I) that is sufficient to treat, ameliorate, or prevent a specified disease (e.g., breast cancer), disease symptom, disorder or condition, or to exhibit a detectable therapeutic or inhibitory effect. The effect can be detected by any assay method known in the art. The effective amount for a particular subject may depend upon the subject's body weight, size, and health; the nature and extent of the condition; and whether additional therapeutics are to be administered to the subject. Therapeutically effective amounts for a given situation can be determined by routine experimentation that is within the skill and judgment of the clinician.

"$C_{max}$", as used herein, refers to the observed maximum (peak) plasma concentration of a specified compound in the subject after administration of a dose of that compound to the subject.

"AUC", as used herein, refers to the total area under the plasma concentration-time curve, which is a measure of exposure to a compound of interest, and is the integral of the concentration-time curve after a single dose or at steady state. AUC is expressed in units of ng*hr/mL (ng×hr/mL).

"$AUC_{tau}$", as used herein, refers to the AUC from 0 hours to the end of a dosing interval.

"Controlled release" or "CR" as used herein with respect to an oral dosage form of the disclosure means that a compound of Formula (I) is released from the dosage form according to a pre-determined profile that may include when and where release occurs after oral administration and/or a specified rate of release over a specified time period. Controlled release may be contrasted with uncontrolled or immediate release.

"Controlled release agent" as used herein with respect to an oral dosage form of the disclosure refers to one or more substances or materials that modulate release of a compound of Formula (I) from the dosage form. Controlled release agents may be materials which are organic or inorganic, naturally occurring or synthetic, such as polymeric materials, triglycerides, derivatives of triglycerides, fatty acids and salts of fatty acids, talc, boric acid and colloidal silica.

"Oral dosage form" as used herein refers to a pharmaceutical drug product that contains a specified amount (dose) of a compound of Formula (I) as the active ingredient, or a pharmaceutically acceptable salt and/or solvate thereof, and inactive components (excipients), formulated into a particular configuration that is suitable for oral administration and drug delivery, such as a tablet, capsule or liquid oral formulation. In one embodiment, the compositions are in the form of a tablet that can be scored.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "about" as part of a quantitative expression such as "about X", includes any value that is 10% higher or lower than X, and also includes any numerical value that falls between X−10% and X+10%. Thus, for example, a weight of about 40 g includes a weight of between 36 to 44 g.

"Comprising" or "comprises" as applied to a particular dosage form, composition, use, method or process described or claimed herein means that the dosage form, composition, use, method, or process includes all of the recited elements in a specific description or claim, but does not exclude other elements. "Consists essentially of" and "consisting essentially of" means that the described or claimed composition, dosage form, method, use, or process does not exclude other materials or steps that do not materially affect the recited physical, pharmacological, pharmacokinetic properties or therapeutic effects of the composition, dosage form, method, use, or process. "Consists of" and "consisting of" means the exclusion of more than trace elements of other ingredients and substantial method or process steps.

"Fasted condition" or "fasted state" as used to describe a subject means the subject has not eaten for at least 4 hours before a time point of interest, such as the time of administering a compound of Formula (I). In an embodiment, a subject in the fasted state has not eaten for at least any of 6, 8, 10 or 12 hours prior to administration of a compound of Formula (I).

"Fed condition" or "fed state" as used to describe a subject herein means the subject has eaten less than 4 hours before a time point of interest, such as the time of administering a compound of Formula (I). In an embodiment, a subject in the fed state has not eaten for at most any of 4, 3, 2, 1 or 0.5 hours prior to administration of a compound of Formula (I).

As used herein, "Tween 80" refers to Polysorbate 80, also known as polyoxyethylene (20) sorbitan monooleate, and sorbitan, mono-9-octadecenoate, poly(oxy-1,2-ethanediyl) derivs, As used herein, "low molecular weight polyethylene glycol" or "low molecular weight PEG" generally refers to polyethylene glycol (PEG) polymers having a molecular weight of less than 1500, 1400, 1300, 1200, 1100, 1000, 900, 800, 700, 600, 500, 400, or 300 Daltons. Examples of low molecular weight PEGs include PEG-200, PEG-400, and PEG-600.

As used herein, the term "CDK4/6 inhibitor" refers to a compound that inhibits the enzymes in humans referred to as cyclin-dependent kinases (CDK) 4 and 6. Examples of a CDK4/6 inhibitor include, without limitation, SHR6390, trilaciclib, lerociclib, AT7519M, dinaciclib, ribociclib, abemaciclib, palbociclib, or any pharmaceutically acceptable salt thereof. In one embodiment, the CDK4/6 inhibitor is palbociclib or a pharmaceutically acceptable salt thereof.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The terms "patient" and "subject" are used interchangeably herein, and refer to a mammal, e.g., a human, mouse, rat, guinea pig, dog, cat, horse, cow, pig, or non-human primate, such as a monkey, chimpanzee, baboon or rhesus.

In one embodiment, the subject is a human.

In one embodiment, the subject is a human who has been diagnosed with breast cancer.

In one embodiment, the subject is a human who has been diagnosed with metastatic breast cancer.

In one embodiment, the subject is a human who has been diagnosed with ER+, HER2− breast cancer.

In one embodiment, the subject is a human who has been diagnosed with metastatic, ER+, HER2− breast cancer.

Compounds of Formula (I)

In one aspect, the application pertains to the methods of treating and/or preventing cancer comprising the administration of a compound of Formula (I) to subject in need thereof.

In one aspect, the application pertains to the use of a compound of Formula (I) in the treatment and/or prevention of breast cancer.

In one aspect, the application pertains to the use of a compound of Formula (I) in the manufacture of a medicament for the treatment and/or prevention of breast cancer.

As referred to herein, a compound of Formula (I) refers to a compound with the following structure:

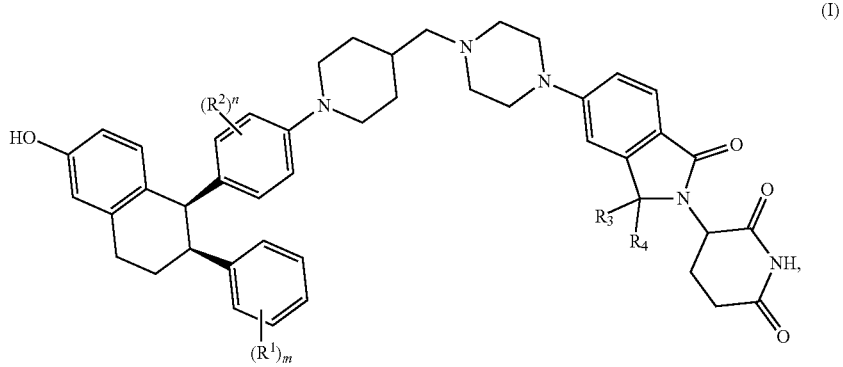

(I)

or a pharmaceutically acceptable salt, enantiomer, stereoisomer, solvate, polymorph, isotopic derivative, or prodrug thereof, wherein:
- each $R^1$ and each $R^2$ is independently selected from the group consisting of halo, $OR_5$, $N(R_5)(R_6)$, $NO_2$, CN, $SO_2(R_5)$, $C_1$-$C_6$ alkyl, and $C_3$-$C_6$ cycloalkyl;
- $R_3$ and $R_4$ are either both hydrogen or, taken together with the carbon to which they are attached, form a carbonyl;
- each $R_5$ and each $R_6$ is independently selected from the group consisting of hydrogen, $C_1$-$C_6$ alkyl, and $C_3$-$C_6$ cycloalkyl;
- m is 0, 1, 2, 3, 4, or 5; and
- n is 0, 1, 2, 3, or 4.

In one embodiment, each $R^1$ and each $R^2$ is independently selected from the group consisting of halo, $OR_5$, and $C_1$-$C_6$ alkyl.

In one embodiment, le is hydrogen, halo, $OR_5$, $N(R_5)(R_6)$, or $C_1$-$C_6$ alkyl. In one embodiment, $R^1$ is hydrogen. In one embodiment, $R^1$ is halo. In one embodiment, $R^1$ is $OR_5$. In one embodiment, le is $N(R_5)(R_6)$. In one embodiment, le is $C_1$-$C_6$ alkyl.

In one embodiment, $R^2$ is hydrogen, halo, $OR_5$, $N(R_5)(R_6)$, or $C_1$-$C_6$ alkyl. In one embodiment, $R^2$ is hydrogen. In one embodiment, $R^2$ is halo. In one embodiment, $R^2$ is $OR_5$. In one embodiment, $R^2$ is $N(R_5)(R_6)$. In one embodiment, $R^2$ is $C_1$-$C_6$ alkyl.

In one embodiment, $R_3$ and $R_4$ are both hydrogen.

In one embodiment, $R_3$ and $R_4$, taken together with the carbon to which they are attached, form a carbonyl.

In one embodiment, each $R_5$ and each $R_6$ is independently selected from the group consisting of hydrogen, and $C_1$-$C_6$ alkyl. In one embodiment, $R_5$ and $R_6$ are each hydrogen.

In one embodiment, m is 0.
In one embodiment, m is 1.
In one embodiment, m is 2.
In one embodiment, m is 3.
In one embodiment, m is 4.
In one embodiment, m is 5.
In one embodiment, n is 0.
In one embodiment, n is 1.
In one embodiment, n is 2.
In one embodiment, n is 3.
In one embodiment, n is 4.
In one embodiment, m and n are each 0.
In one embodiment, m is 0 and n is 1.
In one embodiment, m is 1 and n is 0.
In one embodiment, m is 1 and n is 1.

In one embodiment, the compound of Formula (I) is selected from the group consisting of:

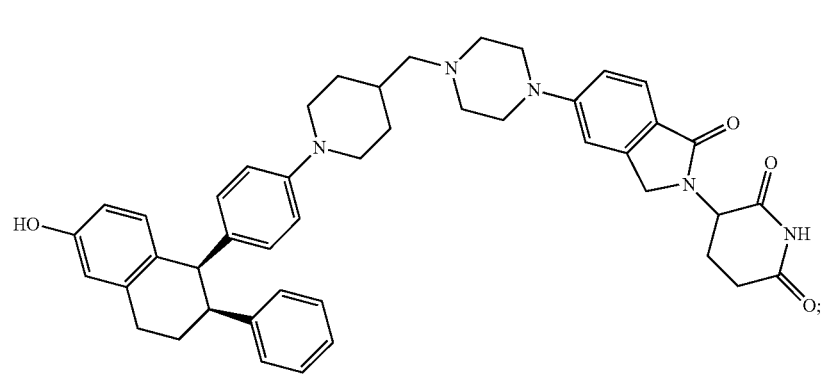

(I-a)

-continued
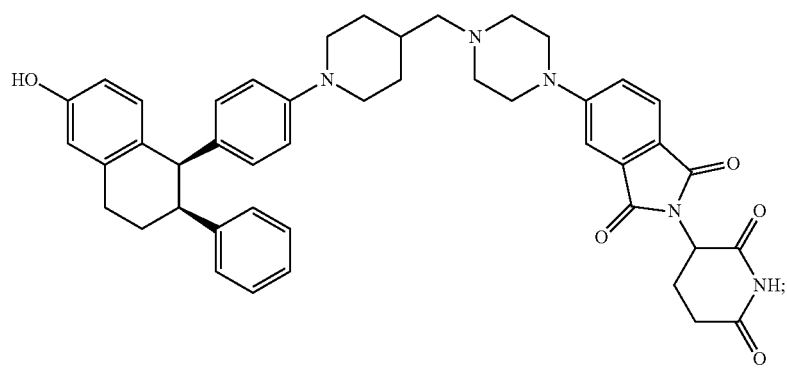
(I-b)
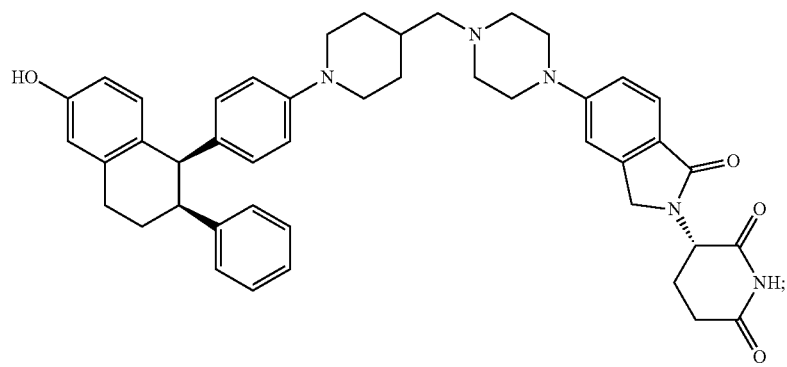
(I-c)
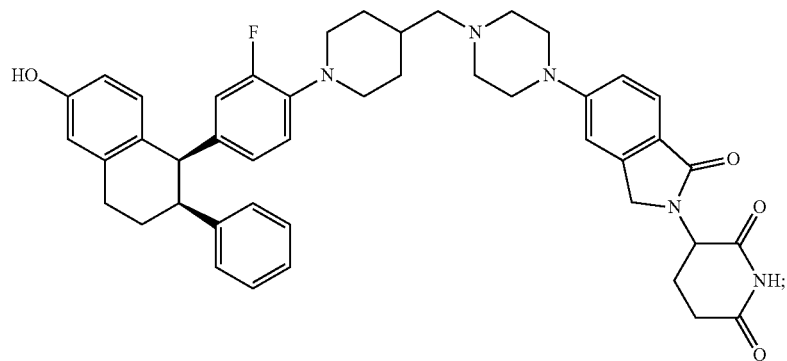
(I-d)
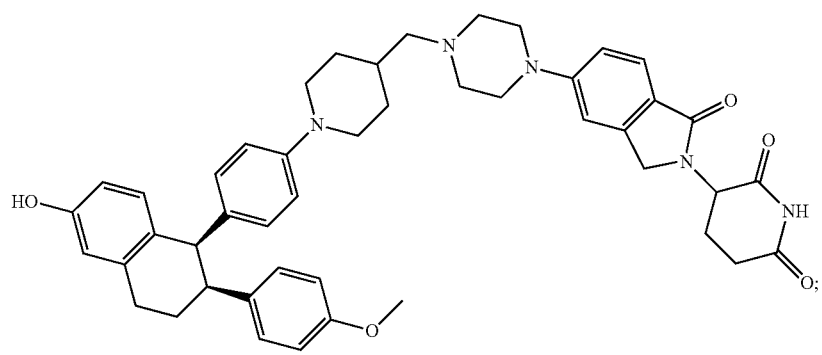
(I-e)

-continued
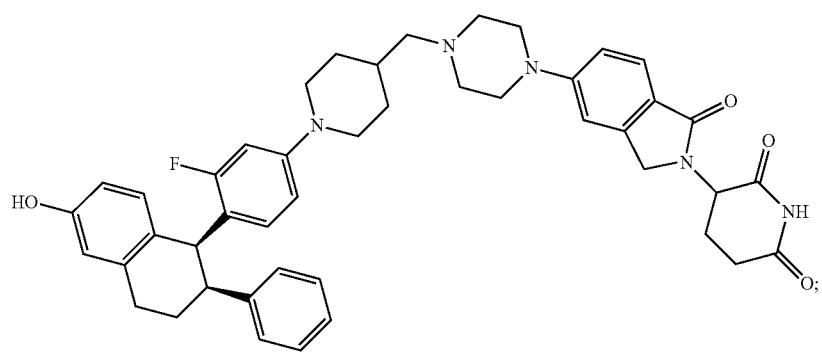
(I-f)
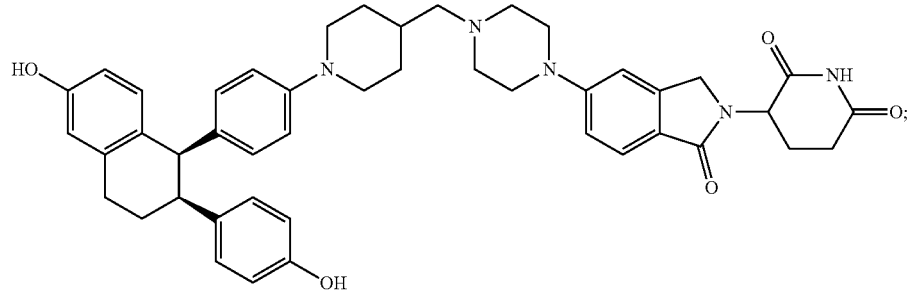
(I-g)
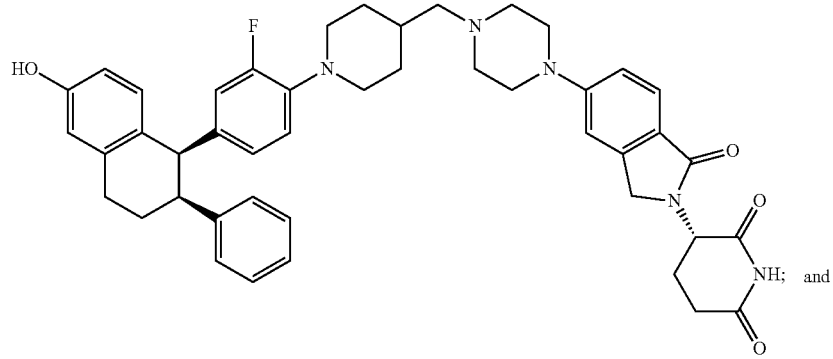
(I-h)
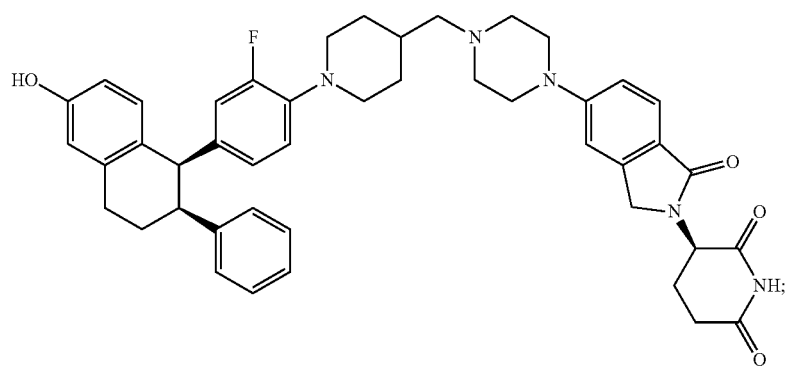
(I-i)
or a pharmaceutically acceptable salt, enantiomer, stereoisomer, solvate, polymorph, isotopic derivative, or prodrug thereof In one embodiment, the compound of Formula (I) is the compound of Formula (I-a):

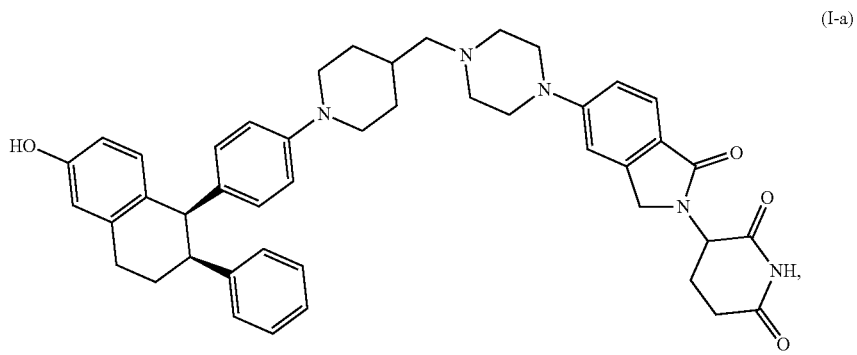 [SMILES: O=C1CCC(N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(I-a)

or a pharmaceutically acceptable salt, enantiomer, stereoisomer, solvate, polymorph, isotopic derivative, or prodrug thereof.

In one embodiment, the compound of Formula (I) is the compound of Formula (I-b):

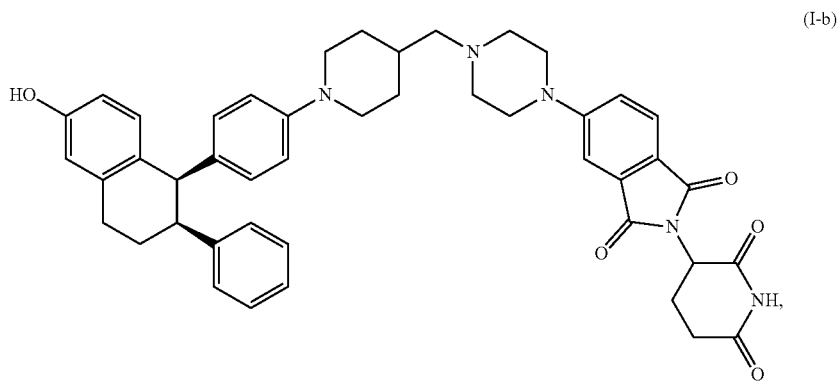 [SMILES: O=C1CCC(N2C(=O)c3ccc(N4CCN(CC5CCN(c6ccc([C@@H]7c8ccc(O)cc8CC[C@@H]7c7ccccc7)cc6)CC5)CC4)cc3C2=O)C(=O)N1]

(I-b)

or a pharmaceutically acceptable salt, enantiomer, stereoisomer, solvate, polymorph, isotopic derivative, or prodrug thereof.

In one embodiment, the compound of Formula (I) is the compound of Formula (I-c), i.e., Compound (I-c) or Cmp (I-c):

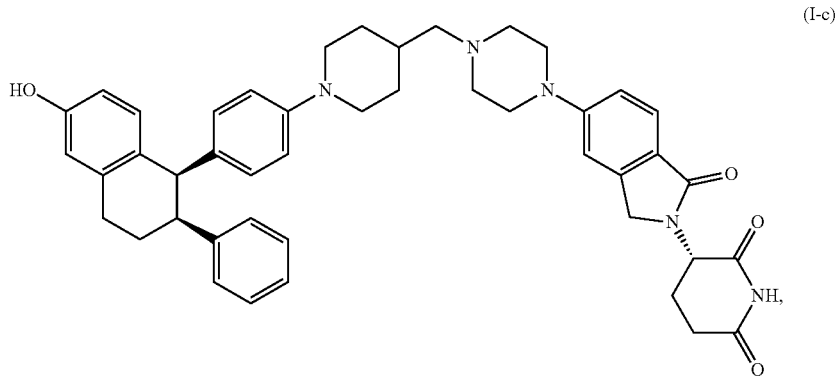 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(I-c)

or a pharmaceutically acceptable salt, enantiomer, stereoisomer, solvate, polymorph, isotopic derivative, or prodrug thereof.

In one embodiment, the compound of Formula (I) is the compound of Formula (I-c), i.e., Compound (I-c) or Cmp (I-c):

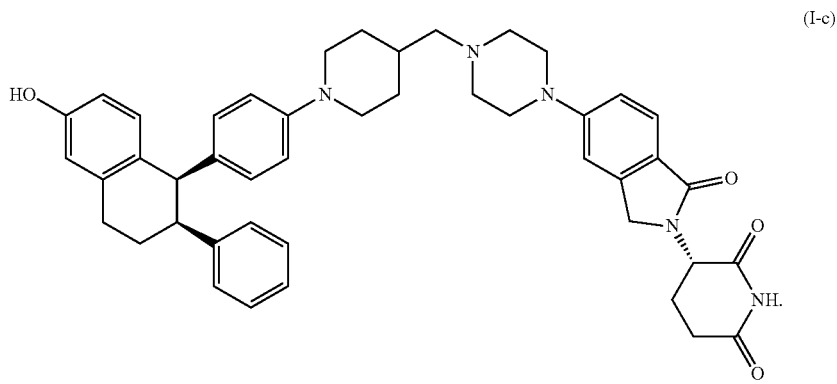 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(I-c)

In one embodiment, the compound of Formula (I) is the compound of Formula (I-d):

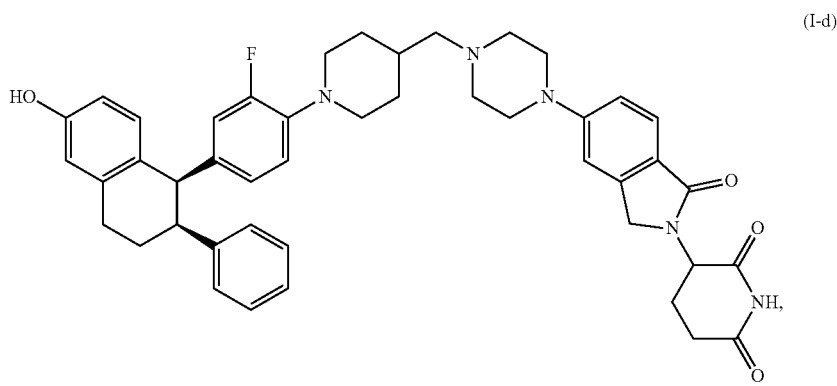

(I-d)

or a pharmaceutically acceptable salt, enantiomer, stereoisomer, solvate, polymorph, isotopic derivative, or prodrug thereof.

In one embodiment, the compound of Formula (I) is the compound of Formula (I-e):

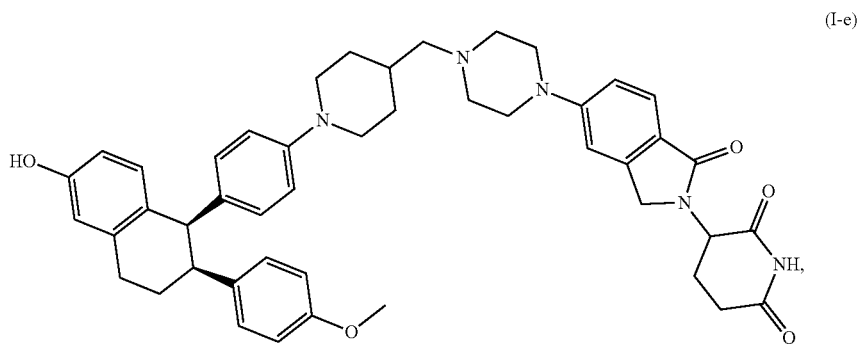 [SMILES: COc1ccc([C@H]2CCc3cc(O)ccc3[C@H]2c2ccc(N3CCC(CN4CCN(c5ccc6c(c5)CN(C5CCC(=O)NC5=O)C6=O)CC4)CC3)cc2)cc1]

(I-e)

or a pharmaceutically acceptable salt, enantiomer, stereoisomer, solvate, polymorph, isotopic derivative, or prodrug thereof.

In one embodiment, the compound of Formula (I) is the compound of Formula (I-f):

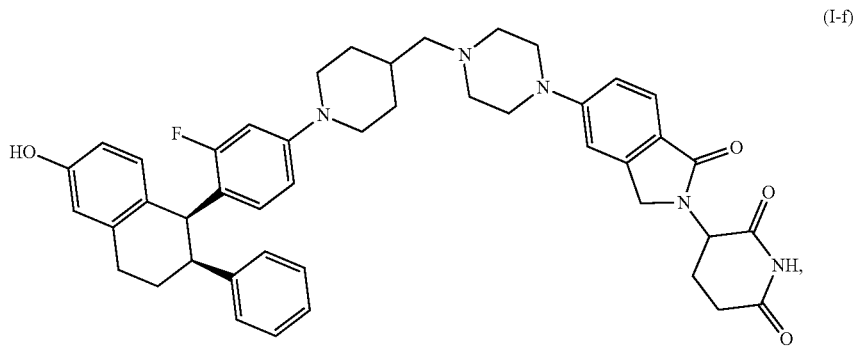 [SMILES: O=C1CCC(N2Cc3cc(N4CCN(CC5CCN(c6ccc([C@@H]7c8ccc(O)cc8CC[C@@H]7c7ccccc7)c(F)c6)CC5)CC4)ccc3C2=O)C(=O)N1]

(I-f)

or a pharmaceutically acceptable salt, enantiomer, stereoisomer, solvate, polymorph, isotopic derivative, or prodrug thereof.

In one embodiment, the compound of Formula (I) is the compound of Formula (I-g):

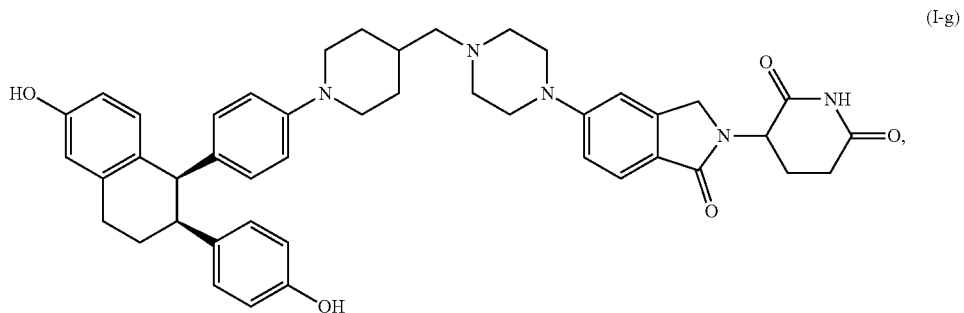 [SMILES: O=C1CCC(N2Cc3cc(N4CCN(CC5CCN(c6ccc([C@@H]7c8ccc(O)cc8CC[C@@H]7c7ccc(O)cc7)cc6)CC5)CC4)ccc3C2=O)C(=O)N1]

(I-g)

or a pharmaceutically acceptable salt, enantiomer, stereoisomer, solvate, polymorph, isotopic derivative, or prodrug thereof.

In one embodiment, the compound of Formula (I) is the compound of Formula (I-h):

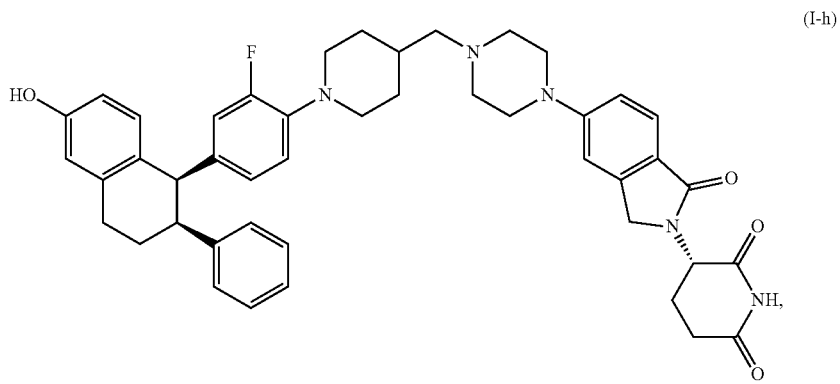

(I-h)

or a pharmaceutically acceptable salt, enantiomer, stereoisomer, solvate, polymorph, isotopic derivative, or prodrug thereof.

In one embodiment, the compound of Formula (I) is the compound of Formula (I-i):

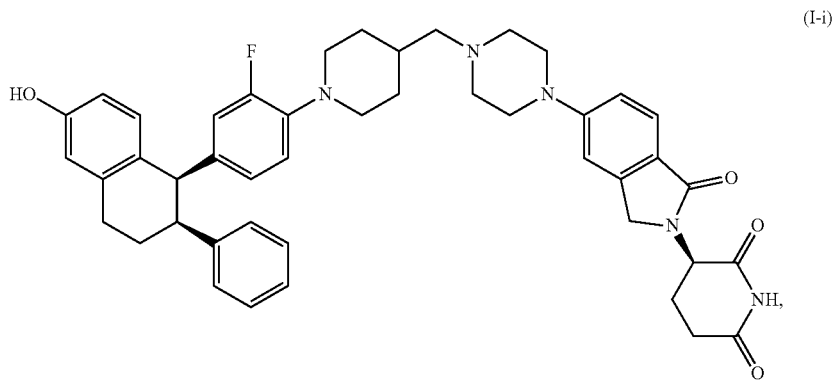 [SMILES: O=C1CC[C@@H](N2Cc3cc(N4CCN(CC5CCN(c6ccc([C@@H]7c8ccc(O)cc8CC[C@@H]7c7ccccc7)cc6F)CC5)CC4)ccc3C2=O)C(=O)N1]

(I-i)

or a pharmaceutically acceptable salt, enantiomer, stereoisomer, solvate, polymorph, isotopic derivative, or prodrug thereof.

A compound of Formula (I), may be synthesized using standard synthetic methods and procedures for the preparation of organic molecules and functional group transformations and manipulations, including the use of protective groups, as can be obtained from the relevant scientific literature or from standard reference textbooks in the field in view of this disclosure. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999. A method for preparing a compound of Formula (I) is described in U.S. Patent Application Publication No. 2018/0155322, which issued as U.S. Pat. No. 10,647,698 the contents of which are incorporated herein in their entirety.

For example, Compounds (I-b) and (I-c) may be prepared according to the procedures described below:

Synthesis of 3-[5-[4-[[1-[4-[(1R, 2S)-6-hydroxy-2-phenyl-tetralin-1-yl]phenyl]-4-piperidyl]methyl]piperazin-1-yl]-1-oxo-isoindolin-2-yl]piperidine-2,6-dione (Compound (I-b)

Step 1: Preparation 6-tert-butoxytetralin-1-one

To a stirred solution of 6-hydroxytetralin-1-one (50 g, 308.29 mmol, 1 eq) in anhydrous dichloromethane (2000 mL) at 0° C. was added tert-butyl 2,2,2-trichloroethanimidate (67.36 g, 308.29 mmol, 55 mL, 1 eq) and pyridinium para-toluenesulfonate (7.75 g, 30.83 mmol, 0.1 eq). The reaction mixture was stirred at 10° C. for 3 hours. Additional portion of tert-butyl 2,2,2-trichloroethanimidate (67.36 g, 308.29 mmol, 55 mL, 1 eq) and pyridinium para-toluenesulfonate (7.75 g, 30.83 mmol, 0.1 eq) was added and the reaction mixture was stirred at 10° C. for 15 hours. This process was repeated three times. Thin layer chromatography (petroleum ether:ethyl acetate=3:1, Rf=0.8) showed that most of reactant still remained, the reaction mixture was stirred at 10° C. for 72 hours. The reaction mixture was quenched by addition of a solution of sodium hydrogen carbonate (1500 mL) at 15° C., and then extracted with dichloromethane (300 mL×3). The combined organic layers were washed with brine (300 mL×2), dried over anhydrous sodium sulfate, filtered and concentrated under reduced pressure. The residue was purified by silica gel chromatography (petroleum ether:ethyl acetate=100:1 to 50:1) to get 6-tert-butoxytetralin-1-one (21 g, 96.20 mmol, 31% yield) as a yellow oil. $^1$H NMR (400 Mhz, CDCl$_3$) δ 7.97 (d, J=8.8 Hz, 1H), 6.91 (dd, J=2.4, 8.8 Hz, 1H), 6.82 (d, J=2.0 Hz, 1H), 2.93-3.90 (t, J=6.0 Hz, 2H), 2.63-2.60 (m, t, J=6.0 Hz, 2H), 2.13 (m, 2H), 1.43 (s, 9H).

Step 2: Preparation of (6-tert-butoxy-3,4-dihydronaphthalen-1-yl) trifluoromethanesulfonate

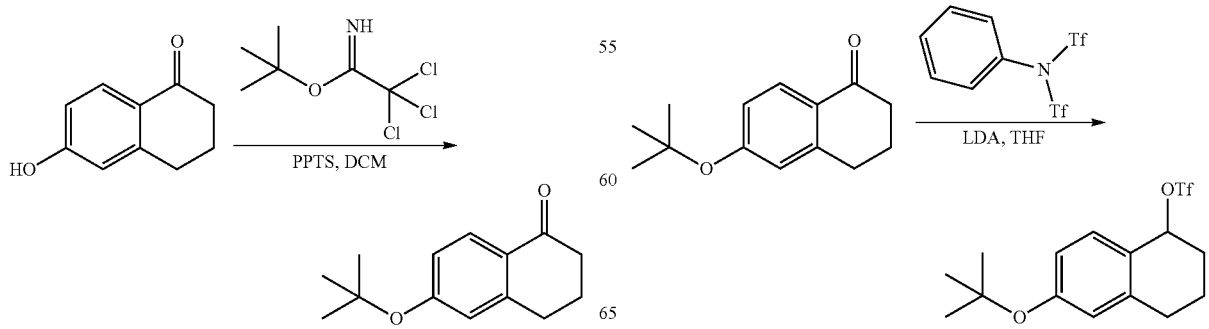

To a solution of 6-tert-butoxytetralin-1-one (40 g, 183.24 mmol, 1 eq) in tetrahydrofuran (500 mL) was added lithium diiso-propylamide (2 M, 137 mL, 1.5 eq) at −70° C. The mixture was stirred at −70° C. for 1 hour, then 1,1,1-trifluoro-N-phenyl-N-(trifluoromethylsulfonyl) methanesulfonamide (72.01 g, 201.56 mmol, 1.1 eq) in tetrahydrofuran (200 mL) was added dropwise to the mixture. The reaction mixture was stirred at 20° C. for 2 hours. Thin layer chromatography (petroleum ether:ethyl acetate=5:1) showed the reaction was completed. Saturated ammonium chloride (300 mL) was added to the mixture, the organic phase was separated. Ethyl acetate (500 mL×3) was added to the mixture, the resulting mixture was washed with brine (1000 mL×2). The combined organic phase was dried over sodium sulfate, filtered and concentrated in vacuum. The residue was purified by silica gel chromatography (petroleum ether:ethyl acetate=1:0 to 50:1) to give (6-tert-butoxy-3,4-dihydronaphthalen-1-yl) trifluoromethanesulfonate (52 g, 144.64 mmol, 78% yield, 97% purity) as a yellow oil. LC-MS (ESI) m/z: 294.9 [M+1-56]$^+$. $^1$H-NMR (400 MHz, CDCl$_3$) δ: 7.30 (d, J=6.4 Hz, 1H), 6.91 (d, J=8.4 Hz, 1H), 6.84 (s, 1H), 5.95 (s, 1H), 2.93-2.78 (m, 2H), 2.59-2.46 (m, 2H), 1.42 (s, 9H).

Step 3: Preparation of 4-(6-tert-butoxy-3,4-dihydronaphthalen-1-yl)phenol

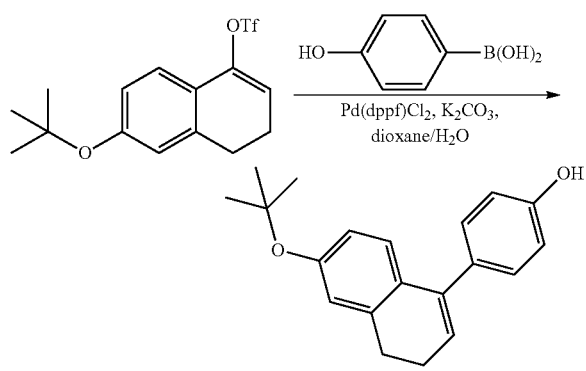

To a solution of (6-tert-butoxy-3,4-dihydronaphthalen-1-yl) trifluoromethanesulfonate (52 g, 148.42 mmol, 1 eq), (4-hydroxyphenyl)boronic acid (24.57 g, 178.11 mmol, 1.2 eq) in dioxane (800 mL) and water (150 mL) was added potassium carbonate (41.03 g, 296.84 mmol, 2 eq) and (1,1'-bis(diphenylphosphino)ferrocene)palladium(II) dichloride (10.86 g, 14.84 mmol, 0.1 eq) under nitrogen. The reaction mixture was stirred at 100° C. for 10 hours. Thin layer chromatography (petroleum ether:ethyl acetate=5:1) showed the reaction was complete. The residue was diluted with water (500 mL) and extracted with ethyl acetate (500 mL×2). The combined organic layers were washed with brine (1000 mL×2), dried with anhydrous sodium sulfate, filtered and concentrated in vacuum. The residue was purified by silica gel chromatography (petroleum ether:tetrahydrofuran=50:1 to 20:1) to give 4-(6-tert-butoxy-3,4-dihydronaphthalen-1-yl)phenol (43 g, 131.46 mmol, 88% yield, 90% purity) as a yellow oil. LCMS (ESI) m/z: 239.1 [M+1-56]$^+$; $^1$H-NMR (400 MHz, CDCl$_3$) δ 7.23 (d, J=7.6 Hz, 2H), 6.91 (d, J=8.0 Hz, 1H), 6.87-6.79 (m, 3H), 6.73 (d, J=8.4 Hz, 1H), 5.95 (s, 1H), 4.83-4.75 (m, 1H), 2.87-2.73 (m, 2H), 2.44-2.31 (m, 2H), 1.37 (s, 9H).

Step 4: Preparation of 4-(2-bromo-6-tert-butoxy-3,4-dihydronaphthalen-1-yl)phenol

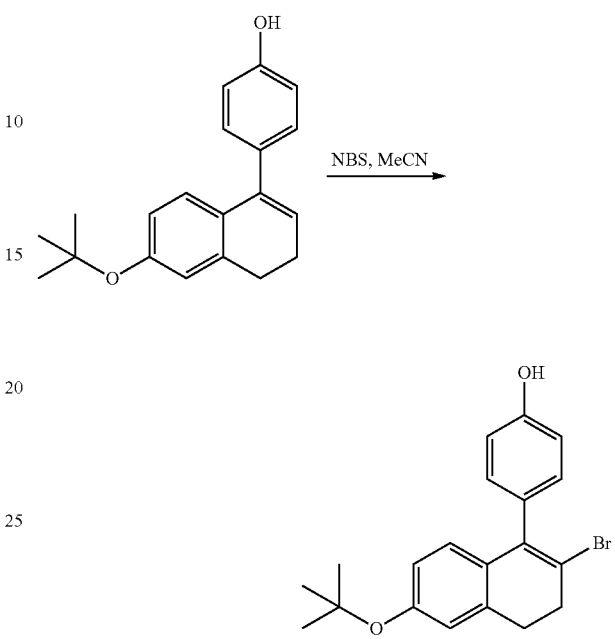

To a solution of 4-(6-tert-butoxy-3,4-dihydronaphthalen-1-yl)phenol (1 g, 3.06 mmol, 1 eq) in acetonitrile (20 mL) was added N-bromosuccinimide (489 mg, 2.75 mmol, 0.9 eq) in three portions. The reaction mixture was stirred at 20° C. for 1.5 hours. LC-MS showed the reaction was completed. The residue was diluted with water (20 mL) and extracted with ethyl acetate (20 mL×2). The combined organic layers were washed with brine (20 mL×2), dried with anhydrous sodium sulfate, filtered and concentrated in vacuum. The residue was purified by silica gel chromatography (petroleum ether:ethyl acetate=1:0 to 20:1) to give 4-(2-bromo-6-tert-butoxy-3,4-dihydronaphthalen-1-yl)phenol (1 g, 2.46 mmol, 80% yield, 91% purity) as a yellow oil. LC-MS (ESI) m/z: 316.9 [M+1-56]$^+$; $^1$H-NMR (400 MHz, CDCl$_3$) δ 7.12 (d, J=8.4 Hz, 2H), 6.90 (d, J=8.0 Hz, 2H), 6.77 (s, 1H), 6.69-6.62 (m, 1H), 6.60-6.53 (m, 1H), 4.86 (s, 1H), 2.96 (s, 4H), 1.35 (s, 9H).

Step 5: Preparation of 4-(6-tert-butoxy-2-phenyl-3,4-dihydronaphthalen-1-yl)phenol

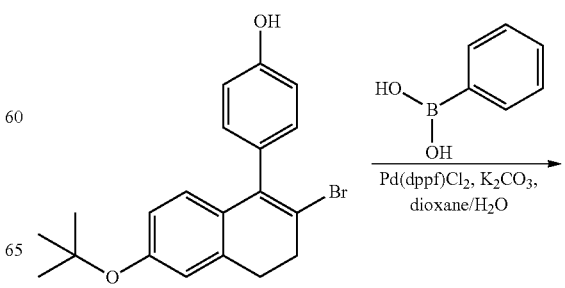

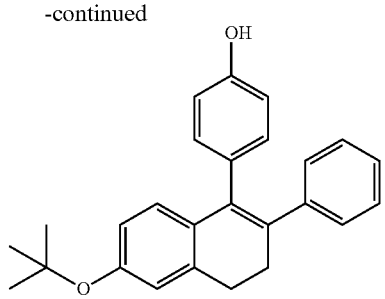

To a solution of 4-(2-bromo-6-tert-butoxy-3,4-dihydronaphthalen-1-yl)phenol (1 g, 2.46 mmol, 1 eq), phenylboronic acid (314 mg, 2.58 mmol, 1.05 eq) in dioxane (10 mL) and water (2 mL) was added potassium carbonate (678 mg, 4.91 mmol, 2 eq) and (1,1'-bis(diphenylphosphino)ferrocene)palladium(II) dichloride (179 mg, 0.24 mmol, 0.1 eq) under nitrogen. The reaction mixture was stirred at 100° C. for 12 hours. LC-MS showed the reaction was completed. The residue was diluted with water (20 mL) and extracted with ethyl acetate (20 mL×2). The combined organic layers were washed with brine (20 mL×3), dried with anhydrous sodium sulfate, filtered and concentrated in vacuum. The residue was purified by silica gel chromatography (petroleum ether:ethyl acetate=1:0 to 10:1) to get 4-(6-tert-butoxy-2-phenyl-3,4-dihydronaphthalen-1-yl)phenol (930 mg, 2.35 mmol, 95% yield, 93% purity) as an orange oil. LCMS (ESI) m/z: 314.1 [M+1-56]$^+$; $^1$H-NMR (400 MHz, CDCl$_3$) δ 7.16-7.09 (m, 2H), 7.08-6.99 (m, 3H), 6.97-6.89 (m, 2H), 6.86-6.82 (m, 1H), 6.74-6.66 (m, 4H), 4.70 (s, 1H), 2.99-2.89 (m, 2H), 2.84-2.75 (m, 2H), 1.37 (s, 9H).

Step 6: Preparation of
4-(6-tert-butoxy-2-phenyl-tetralin-1-yl)phenol

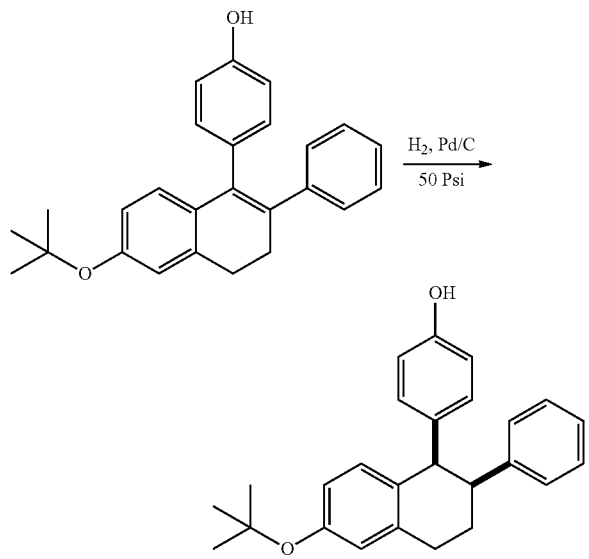

To a solution of 4-(6-tert-butoxy-2-phenyl-3,4-dihydronaphthalen-1-yl)phenol (930 mg, 2.35 mmol, 1 eq) in tetrahydrofuran (20 mL) and methanol (4 mL) was added palladium on activated carbon catalyst (100 mg, 10% purity) under nitrogen. The suspension was degassed under vacuum and purged with hydrogen three times. The mixture was stirred under hydrogen (50 psi) at 30° C. for 36 hours. LC-MS showed the reaction was completed. The reaction mixture was filtered and the solution was concentrated. The resulting material was directly used into the next step without further purification to afford cis-4-(6-tert-butoxy-2-phenyl-tetralin-1-yl)phenol (870 mg, 2.14 mmol, 91% yield, 91% purity) as a white solid. LC-MS (ESI) m/z: 317.0 [M+1-56]$^+$; $^1$H-NMR (400 MHz, CDCl$_3$) δ 7.22-7.12 (m, 3H), 6.89-6.78 (m, 4H), 6.74 (dd, J=2.0, 8.4 Hz, 1H), 6.45 (d, J=8.4 Hz, 2H), 6.27 (d, J=8.4 Hz, 2H), 4.51 (s, 1H), 4.25 (d, J=4.8 Hz, 1H), 3.38 (dd, J=3.2, 12.8 Hz, 1H), 3.08-2.99 (m, 2H), 2.27-2.08 (m, 1H), 1.87-1.76 (m, 1H), 1.37 (s, 9H).

Step 7: Preparation of 4-[(1S,2R)-6-tert-butoxy-2-phenyl-tetralin-1-yl]phenol

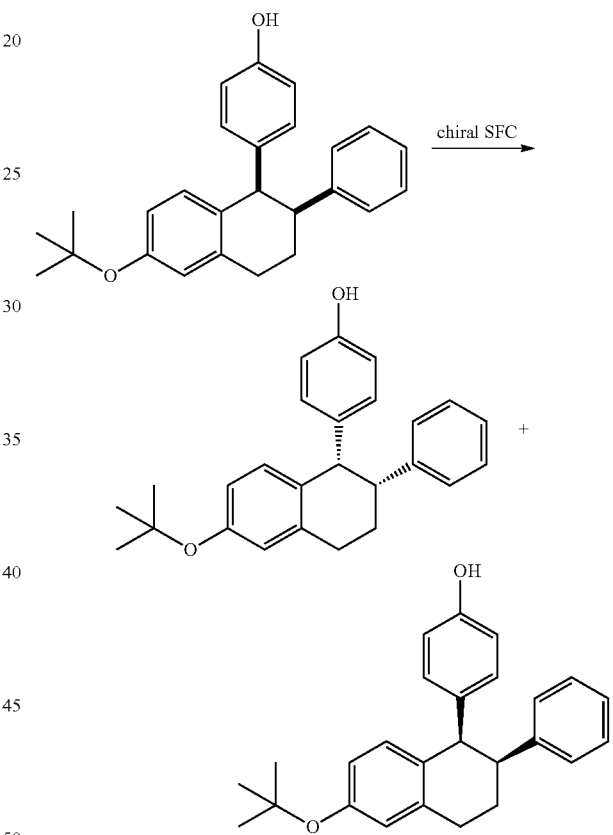

4-(6-tert-butoxy-2-phenyl-tetralin-1-yl)phenol (870 mg, 2.13 mmol, 1 eq) was subjected to supercritical fluid chromatography for chiral separation (column: AD, 250 mm×30 mm, 5 um; mobile phase: 0.1% ammonium hydroxide in methanol, 20%-20%, 4.2 min for each run) to get 4-[(1S,2R)-6-tert-butoxy-2-phenyl-tetralin-1-yl]phenol (420 mg, 1.04 mmol, 97% yield, 92% purity) as the first fraction and 4-[(JR, 2S)-6-tert-butoxy-2-phenyl-tetralin-1-yl]phenol (420 mg, 1.04 mmol, 97% yield, 92% purity) as a second fraction. Fraction 1: [α]$_D$=+336.9 (C=0.50 g/100 mL in ethyl acetate, 25° C.), LC-MS (ESI) m/z: 395.1 [M+23]$^+$; $^1$H NMR (400 MHz, DMSO-d$_6$) δ 9.02 (s, 1H), 7.20-7.07 (m, 3H), 6.87-6.79 (m, 3H), 6.79-6.72 (m, 1H), 6.71-6.64 (m, 1H), 6.36 (d, J=8.4 Hz, 2H), 6.15 (d, J=8.4 Hz, 2H), 4.19 (d, J=4.8 Hz, 1H), 3.31-3.26 (m, 1H), 3.09-2.89 (m, 2H), 2.17-2.04 (m, 1H), 1.79-1.65 (m, 1H), 1.29 (s, 9H). Fraction 2: [α]D=−334.1 (C=0.50 g/100 mL in ethyl acetate, 25° C.), LC-MS (ESI) m/z: 395.2 [M+23]⁺; ¹H-NMR (400 MHz, DMSO-d₆) δ: 9.02 (s, 1H), 7.21-7.06 (m, 3H), 6.88-6.78 (m, 3H), 6.78-6.72 (m, 1H), 6.71-6.64 (m, 1H), 6.36 (d, J=8.4 Hz, 2H), 6.15 (d, J=8.4 Hz, 2H), 4.19 (d, J=4.8 Hz, 1H), 3.30-3.27 (m, 1H), 3.08-2.90 (m, 2H), 2.16-2.04 (m, 1H), 1.79-1.65 (m, 1H), 1.29 (s, 9H).

Step 8: Preparation of 4-(6-benzyloxy-2-phenyl-3,4-dihydronaphthalen-1-yl)phenyl] 1,1,2,2,3,3,4,4,4-nonafluorobutane-1-sulfonate

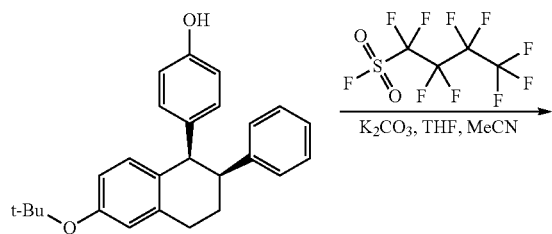

To a solution of 4-[(1R,2S)-6-tert-butoxy-2-phenyl-tetralin-1-yl]phenol (1 g, 2.68 mmol, 1 eq) and 1,1,2,2,3,3,4,4,4-nonafluorobutane-1-sulfonyl fluoride (811 mg, 2.68 mmol, 1 eq) in tetrahydrofuran (5 mL) and acetonitrile (5 mL) was added potassium carbonate (557 mg, 4.03 mmol, 1.5 eq). The reaction mixture was stirred at 25° C. for 16 hours. TLC (petroleum ether:ethyl acetate=10:1) indicated the starting material was consumed completely and one new spot formed. The reaction mixture was concentrated under reduced pressure. The residue was purified by silica gel chromatography (petroleum ether:ethyl acetate=1:0 to 50:1). The desired compound [4-[(1R,2S)-6-tert-butoxy-2-phenyl-tetralin-1-yl]phenyl] 1,1,2,2,3,3,4,4,4-nonafluorobutane-1-sulfonate (1.6 g, 2.44 mmol, 91% yield) was obtained as a colorless oil. ¹H NMR (400 MHz, CDCl₃) δ 7.21-7.11 (m, 3H), 6.94-6.86 (m, 3H), 6.84-6.73 (m, 4H), 6.46 (d, J=8.8 Hz, 2H), 4.33 (d, J=5.2 Hz, 1H), 3.50-3.40 (m, 1H), 3.16-2.95 (m, 2H), 2.20-2.02 (m, 1H), 1.91-1.79 (m, 1H), 1.38 (s, 9H).

Step 9: Preparation of 1-[4-(6-benzyloxy-2-phenyl-3,4-dihydronaphthalen-1-yl) phenyl]-4-(dimethoxymethyl)piperidine

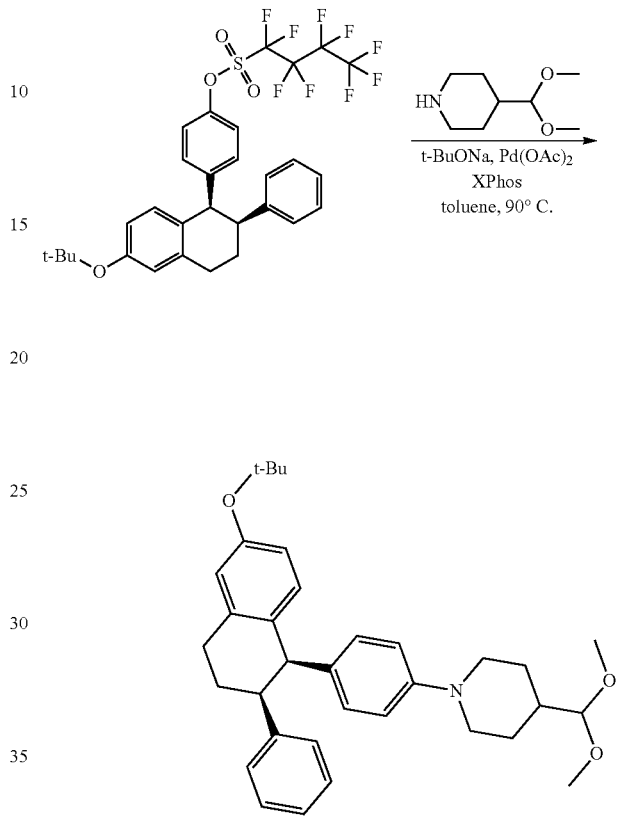

A mixture of [4-[(1R,2S)-6-tert-butoxy-2-phenyl-tetralin-1-yl]phenyl] 1,1,2,2,3,3,4,4,4-nonafluorobutane-1-sulfonate (1.6 g, 2.44 mmol, 1 eq), 4-(dimethoxymethyl)piperidine (584 mg, 3.67 mmol, 1.5 eq), sodium tert-butoxide (705 mg, 7.33 mmol, 3 eq), palladium acetate (82 mg, 0.37 mmol, 0.15 eq) and dicyclohexylphosphino-2',4',6'-triisopropylbiphenyl (233 mg, 0.49 mmol, 0.2 eq) in toluene (30 mL) was degassed and purged with nitrogen three times, and then the mixture was stirred at 90° C. for 16 hours under nitrogen atmosphere. LC-MS showed one main peak with desired MS was detected. TLC (petroleum ether:ethyl acetate=10:1) indicated the starting material was consumed completely and one new spot formed. The mixture was cooled, diluted with ethyl acetate (50 mL), filtered on a plug of diatomaceous earth, the filter cake was washed with ethyl acetate (30 mL). The filtrate was concentrated. The residue was purified by silica gel chromatography (petroleum ether:ethyl acetate=100:1 to 10:1). The desired compound 1-[4-[(1R,2S)-6-tert-butoxy-2-phenyl-tetralin-1-yl]phenyl]-4-(dimethoxymethyl)piperidine (1.1 g, 2.14 mmol, 87% yield) was obtained as a white solid. LC-MS (ESI) m/z: 514.3 [M+1]⁺; ¹H NMR (400 MHz, CDCl₃) δ 7.21-7.11 (m, 3H), 6.88-6.78 (m, 4H), 6.73 (dd, J=2.4, 8.0 Hz, 1H), 6.57 (d, J=8.4 Hz, 2H), 6.27 (d, J=8.8 Hz, 2H), 4.23 (d, J=4.8 Hz, 1H), 4.06 (d, J=7.2 Hz, 1H), 3.63-3.52 (m, 2H), 3.41-3.30 (m, 7H), 3.13-2.96 (m, 2H), 2.54 (d, J=2.0, 12.0 Hz, 2H), 2.28-2.10 (m, 1H), 1.85-1.63 (m, 4H), 1.49-1.31 (m, 11H).

Step 10: Preparation of 1-[4-[(1R,2S)-6-hydroxy-2-phenyl-tetralin-1-yl]phenyl]piperidine-4-carbaldehyde

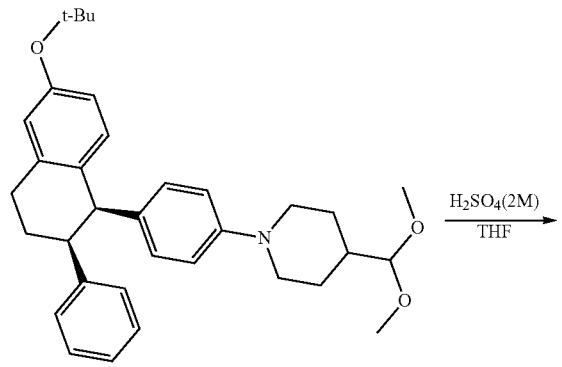

To a solution of 1-[4-[(1R,2S)-6-tert-butoxy-2-phenyl-tetralin-1-yl]phenyl]-4-(dimethoxymethyl)piperidine (1.1 g, 2.14 mmol, 1 eq) in tetrahydrofuran (45 mL) was added sulfuric acid (2 M, 43 mL, 40 eq). The reaction mixture was stirred at 70° C. for 1 hour. LC (petroleum ether:ethyl acetate=3:1) indicated the starting material was consumed completely and one new spot formed. The reaction mixture was quenched by addition of saturated sodium bicarbonate solution to pH=7-8, and extracted with ethyl acetate (20 mL×2). The combined organic layers were washed with brine (20 mL), dried over sodium sulfate, filtered and concentrated under reduced pressure. The residue was used into next step without further purification. The desired compound 1-[4-[(1R,2S)-6-hydroxy-2-phenyl-tetralin-1-yl]phenyl]piperidine-4-carbaldehyde (900 mg, 2.14 mmol, 99% yield, 97% purity) was obtained as light yellow solid. LCMS MS (ESI) m/z: 412.1 [M+1]$^+$

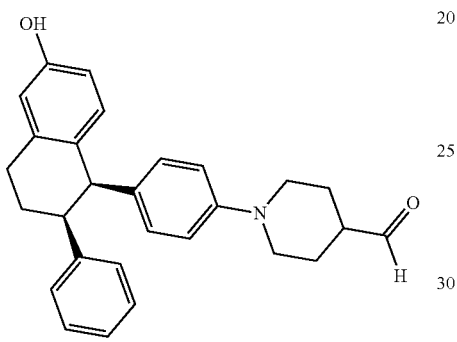

Step 11: Preparation of 3-[5-[4-[[1-[4-[(1R, 2S)-6-hydroxy-2-phenyl-tetralin-1-yl]phenyl]-4-piperidyl]methyl]piperazin-1-yl]-1-oxo-isoindolin-2-yl]piperidine-2,6-dione (Compound (I-b))

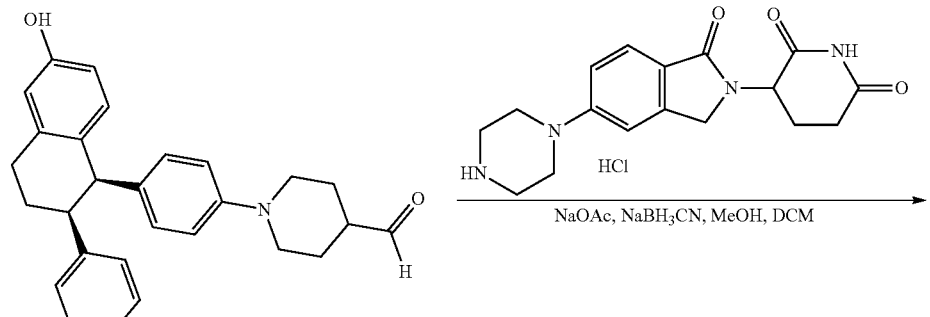

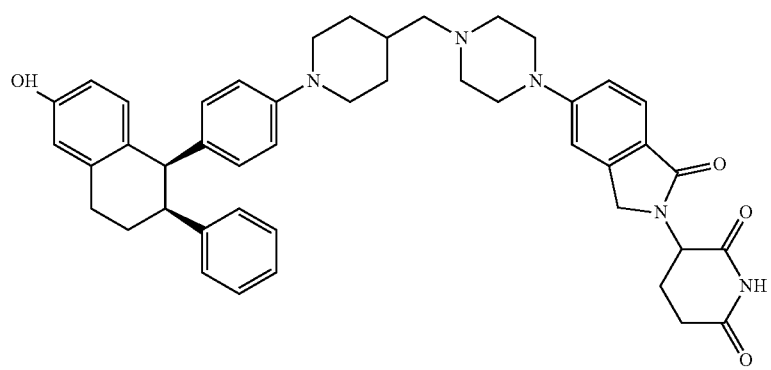

To a solution of 3-(1-oxo-5-piperazin-1-yl-isoindolin-2-yl)piperidine-2,6-dione hydrochloride (319 mg, 0.87 mmol, prepared in Step 17 described for Exemplary Compound 62) in methanol (4 mL) and dichloromethane (4 mL) was added sodium acetate (120 mg, 1.46 mmol, 2 eq). The mixture was stirred at 20° C. for 0.5 h, then to the mixture was added 1-[4-[(1R,2S)-6-hydroxy-2-phenyl-tetralin-1-yl]phenyl]piperidine-4-carbaldehyde (300 mg, 0.73 mmol, 1 eq) and sodium cyanoborohydride (137 mg, 2.19 mmol, 3 eq). The mixture was stirred at 20° C. for 12 h. LC-MS showed the starting material was consumed completely and one main peak with desired MW was detected. The reaction mixture was concentrated under reduced pressure. The residue was purified by prep-HPLC (Phenomenex luna $C_{18}$ column, 250×50 mm, 10 um; mobile phase: [water (0.05% HCl)-acetonitrile]; B %: acetonitrile 10%-40% in 30 min). The desired compound 3-[5-[4-[[1-[4-[(1R, 2S)-6-hydroxy-2-phenyl-tetralin-1-yl]phenyl]-4-piperidyl]methyl]piperazin-1-yl]-1-oxo-isoindolin-2-yl]piperidine-2,6-dione (288.4 mg, 0.37 mmol, 51% yield) was obtained as a white solid of hydrochloride salt. LC-MS (ESI) m/z: 724.4 [M+1]$^+$; $^1$H NMR (400 MHz, DMSO-$d_6$) δ 10.97 (s, 1H), 10.83 (s, 0.9H, HCl), 7.60 (d, J=8.5 Hz, 1H), 7.40 (br s, 2H), 7.22-7.11 (m, 5H), 6.83 (d, J=6.0 Hz, 2H), 6.69-6.63 (m, 2H), 6.58-6.47 (m, 3H), 5.07 (dd, J=5.2, 13.2 Hz, 1H), 4.41-4.30 (m, 2H), 4.28-4.21 (m, 1H), 4.00 (d, J=12.7 Hz, 2H), 3.61 (d, J=11.0 Hz, 2H), 3.54-3.36 (m, 6H), 3.16 (br s, 4H), 3.06-2.84 (m, 3H), 2.76-2.53 (m, 1H), 2.43-2.33 (m, 1H), 2.27 (br s, 1H), 2.16-2.04 (m, 3H), 2.02-1.69 (m, 5H).

Synthesis of (3S)-3-[5-[4-[[1-[4-[(1R, 2S)-6-hydroxy-2-phenyl-tetralin-1-yl]phenyl]-4-piperidyl]methyl]piperazin-1-yl]-1-oxo-isoindolin-2-yl]piperidine-2,6-dione (Compound (I-c))

Step 1: Preparation of tert-butyl (4S)-5-amino-4-(benzyloxycarbonyl amino)-5-oxo-pentanoate

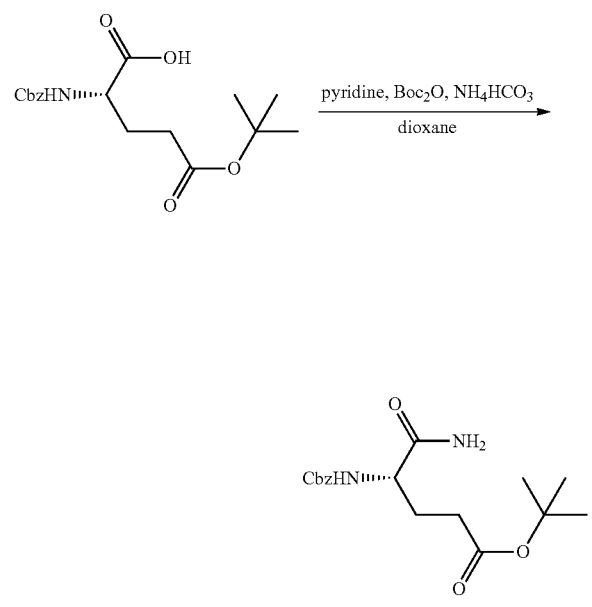

A mixture of (2S)-2-(benzyloxycarbonylamino)-5-tert-butoxy-5-oxo-pentanoic acid (20 g, 59.28 mmol, 1.00 eq), di-tert-butyl dicarbonate (94.85 mmol, 21.79 mL, 1.60 eq) and pyridine (9.38 g, 118.57 mmol, 9.57 mL, 2.00 eq) in 1,4-dioxane (200 mL) was degassed at 0° C. and purged with nitrogen for 3 times, and then the mixture was stirred at 0° C. for 0.5 hour under nitrogen atmosphere. Ammonium bicarbonate (14.06 g, 177.85 mmol, 14.65 mL, 3.00 eq) was added at 0° C. The mixture was stirred at 25° C. for 16 hours. LC-MS showed the desired mass. The volatiles were removed under reduced pressure. The residue was diluted with water (300 mL) and extracted with ethyl acetate (300 mL×1). The combined organic phase was washed with aq. hydrochloric acid (0.5 M, 200 mL×2), saturated sodium bicarbonate (300 mL×3) and brine (500 mL×3), dried with anhydrous sodium sulfate, filtered and concentrated in vacuum to give the crude product. The crude product was triturated (petroleum ether:ethyl acetate=10:1, 300 mL) to provide tert-butyl (4S)-5-amino-4-(benzyloxycarbonylamino)-5-oxo-pentanoate (19 g, 56.08 mmol, 94% yield, 99% purity) as a white solid. LC-MS (ESI) m/z: 359.0 [M+23]$^+$. $^1$H-NMR (400 MHz, CDCl$_3$) δ 7.39-7.29 (m, 5H), 6.38 (s, 1H), 5.74 (d, J=7.2 Hz, 1H), 5.58 (s, 1H), 5.11 (s, 2H), 4.25 (d, J=5.6 Hz, 1H), 2.55-2.41 (m, 1H), 2.39-2.27 (m, 1H), 2.18-2.04 (m, 1H), 2.02-1.85 (m, 1H), 1.45 (s, 9H).

Step 2: Preparation of Tert-Butyl (4S)-4,5-diamino-5-oxo-pentanoate

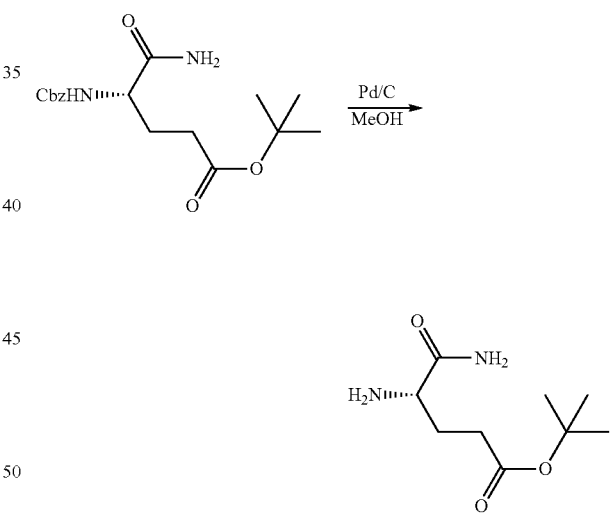

To a solution of tert-butyl (4S)-5-amino-4-(benzyloxycarbonylamino)-5-oxo-pentanoate (19 g, 56.48 mmol, 1.00 eq) in methanol (200 mL) was added palladium on carbon (2 g, 10%) under nitrogen atmosphere. The suspension was degassed and purged with hydrogen 3 times. The mixture was stirred under H$_2$ (50 psi) at 25° C. for 16 hours. Thin layer chromatography (petroleum ether:ethyl acetate=1:2) showed the reaction was completed. The reaction mixture was filtered and the filtrate was concentrated. Compound tert-butyl (4S)-4,5-diamino-5-oxo-pentanoate (11 g, 54.39 mmol, 96% yield) was obtained as a light green oil. $^1$H NMR (400 MHz, CDCl$_3$) δ 7.03 (br s, 1H), 5.55 (br s, 1H), 3.44 (br s, 1H), 2.49-2.31 (m, 2H), 2.11 (dd, J=6.0, 12.8 Hz, 1H), 1.92-1.76 (m, 1H), 1.66 (s, 2H), 1.45 (s, 9H).

Step 3: Preparation of Tert-Butyl 4-[2-[(1S)-4-tert-butoxy-1-carbamoyl-4-oxo-butyl]-1-oxo-isoindolin-5-yl]piperazine-1-carboxylate

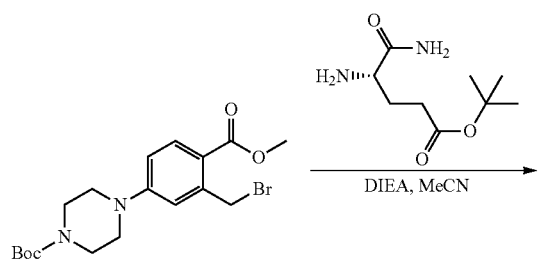

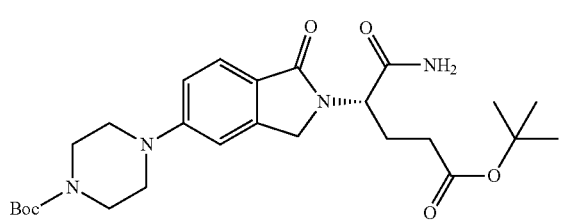

To a solution of tert-butyl 4-[3-(bromomethyl)-4-methoxycarbonyl-phenyl]piperazine-1-carboxylate (1.5 g, 3.63 mmol, 1 eq, prepared in step 15, Exemplary Compound 62 in U.S. Patent Application Publication No. 2018/0155322) in acetonitrile (30 mL) was added tert-butyl (4S)-4,5-diamino-5-oxo-pentanoate (1.10 g, 5.44 mmol, 1.5 eq) and diisopropylethylamine (1.41 g, 10.89 mmol, 1.90 mL, 3 eq). The mixture was stirred at 80° C. for 12 hours. LC-MS showed the reaction was completed. The mixture was diluted with water (30 mL) and extracted with ethyl acetate (20 mL×3). The combined organic layers was washed with brine (30 mL×2), dried with anhydrous sodium sulfate, filtered and the filtrate was concentrated in vacuum. The residue was purified by preparative reverse phase HPLC (column: Phenomenex Synergi Max-RP 250×50 mm, 10 micron; mobile phase: [water (0.225% formic acid)-acetonitrile]; B %: 40 acetonitrile %-70 acetonitrile % in 30 min) to provide tert-butyl 4-[2-[(1S)-4-tert-butoxy-1-carbamoyl-4-oxo-butyl]-1-oxo-isoindolin-5-yl]piperazine-1-carboxylate (1.6 g, 2.94 mmol, 81.05% yield, 92% purity) as an off-white solid. LC-MS (ESI) m/z: 503.2 [M+1]

Step 4: Preparation of (3 S)-3-(1-oxo-5-piperazin-1-yl-isoindolin-2-yl) piperidine-2,6-dione

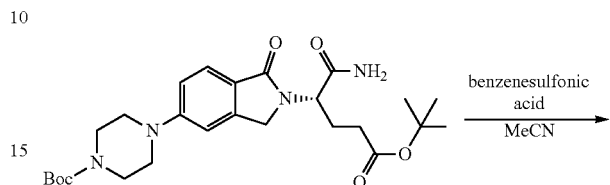

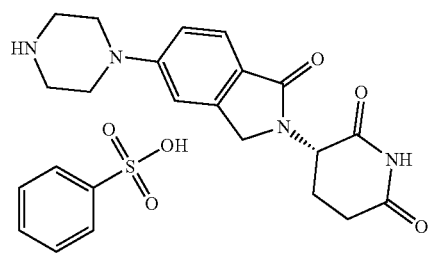

To a solution of tert-butyl 4-[2-[(1S)-4-tert-butoxy-1-carbamoyl-4-oxo-butyl]-1-oxo-isoindolin-5-yl]piperazine-1-carboxylate (700 mg, 1.39 mmol, 1 eq) in acetonitrile (15 mL) was added benzenesulfonic acid (440 mg, 2.79 mmol, 2 eq). The mixture was stirred at 85° C. for 12 hours. LC-MS showed the reaction was completed. The mixture was concentrated in vacuum. The residue was triturated with ethyl acetate (30 mL×3) to get (3S)-3-(1-oxo-5-piperazin-1-yl-isoindolin-2-yl)piperidine-2,6-dione (630 mg, crude) as a gray solid. LC-MS (ESI) m/z: 329.1 [M+1]⁺; 100% ee from chiral SFC analysis.

Step 5: Preparation of (3 S)-3-[5-[4-[[1-[4-[(1R, 2S)-6-hydroxy-2-phenyl-tetralin-1-yl]phenyl]-4-piperidyl]methyl]piperazin-1-yl]-1-oxo-isoindolin-2-yl]piperidine-2,6-dione (Compound (I-c))

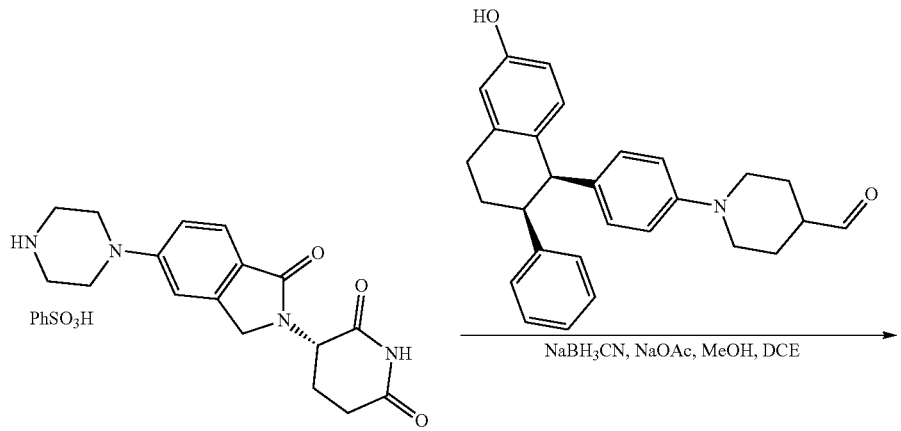

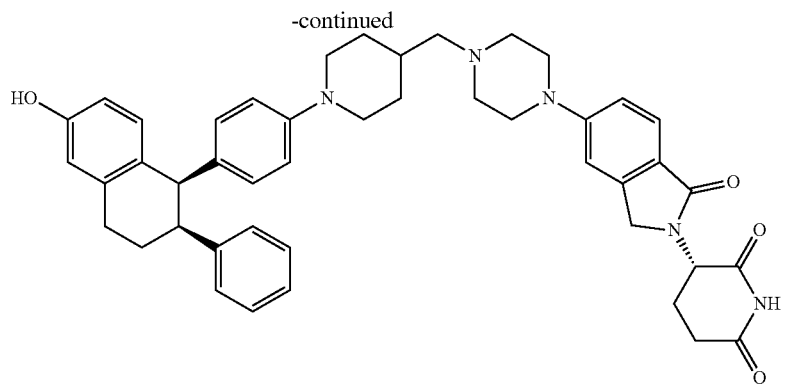

To a mixture of (3 S)-3-(1-oxo-5-piperazin-1-yl-isoindolin-2-yl)piperidine-2,6-dione (1.30 g, 3.47 mmol, 1 eq, benzene sulfonate) in dichloromethane (8 mL) and methanol (32 mL) was added sodium acetate (854 mg, 10.41 mmol, 3 eq) in one portion at 20° C. The mixture was stirred at 20° C. for 10 minutes. Then 1-[4-[(1R, 2S)-6-hydroxy-2-phenyl-tetralin-1-yl]phenyl] piperidine-4-carbaldehyde (1 g, 2.43 mmol, 0.7 eq, prepared as described above in the synthesis of Compound (I-b)) was added. The mixture was stirred at 20° C. for 10 minutes. After that, acetic acid (0.2 mL) and sodium cyanoborohydride (436 mg, 6.94 mmol, 2 eq) was added in one portion. The mixture was stirred at 20° C. for 40 minutes. The mixture was concentrated in vacuum, and 50 mL of tetrahydrofuran and 20 mL of water were added. The mixture was stirred for 20 minutes. Saturated aqueous sodium bicarbonate solution was added to adjust the pH to 8-9. The aqueous phase was extracted with ethyl acetate and tetrahydrofuran (v:v=2:1, 60 mL×3). The combined organic phase was washed with brine (60 mL×1), dried with anhydrous sodium sulfate, filtered and concentrated in vacuum. The residue was purified by preparative reverse phase HPLC (column: Phenomenex luna C18 250×50 mm, 10 micron; mobile phase: [water (0.225% formic acid)-acetonitrile]; B %: 20%-50% in 30 min). The product (3S)-3-[5-[4-[[1-[4-[(1R,2S)-6-hydroxy-2-phenyl-tetralin-1-yl]phenyl]-4-piperidyl]methyl] piperazin-1-yl]-1-oxo-isoindolin-2-yl]piperidine-2,6-dione (964 mg, 1.23 mmol, 35% yield, 98% purity, formate) was obtained as a white solid of formic acid salt after lyophilization. Chiral purity was analyzed by chiral SFC (Chiralcel OJ-3 50×4.6 mm, 3 micron; mobile phase: 50% ethanol (0.05% DEA) in $CO_2$; flow rate: 3 mL/min, wavelength: 220 nm) and observed $t_p$=2.89 min with de over 95%. $[\alpha_D]$=−267.5 (c=0.2 in DMF, 25° C.). LC-MS (ESI) m/z: 724.2 [M+1]$^+$. $^1$H NMR (400 MHz, DMSO-$d_6$) δ 10.94 (s, 1H), 8.16 (s, 1H, formate), 7.51 (d, J=8.8 Hz, 1H), 7.21-6.98 (m, 5H), 6.83 (d, J=6.4 Hz, 2H), 6.68-6.57 (m, 2H), 6.56-6.44 (m, 3H), 6.20 (d, J=8.8 Hz, 2H), 5.04 (dd, J=5.2, 13.2 Hz, 1H), 4.32 (d, J=16.8 Hz, 1H), 4.19 (d, J=17.2 Hz, 1H), 4.12 (d, J=4.8 Hz, 1H), 3.51 (br d, J=10.0 Hz, 4H), 3.27 (br s, 8H), 3.03-2.82 (m, 3H), 2.63-2.54 (m, 1H), 2.43-2.28 (m, 2H), 2.19 (d, J=6.8 Hz, 2H), 2.15-2.02 (m, 1H), 2.01-1.89 (m, 1H), 1.83-1.51 (m, 4H), 1.28-1.04 (m, 2H).

$^1$H-NMR of the free non-salt form: (400 MHz, DMSO-$d_6$) δ 10.93 (s, 1H), 9.09 (s, 1H), 7.51 (d, J=8.8 Hz, 1H), 7.18-7.09 (m, 3H), 7.08-7.02 (m, 2H), 6.83 (d, J=6.4 Hz, 2H), 6.64 (d, J=8.4 Hz, 1H), 6.60 (d, J=2.0 Hz, 1H), 6.53 (d, J=8.8 Hz, 2H), 6.48 (dd, J=2.4, 8.4 Hz, 1H), 6.20 (d, J=8.8 Hz, 2H), 5.04 (dd, J=5.2, 13.2 Hz, 1H), 4.39-4.27 (m, 1H), 4.24-4.15 (m, 1H), 4.12 (d, J=4.8 Hz, 1H), 3.51 (d, J=9.6 Hz, 2H), 3.29-3.24 (m, 5H), 3.03-2.83 (m, 3H), 2.62-2.54 (m, 4H), 2.52 (s, 3H), 2.41-2.36 (m, 1H), 2.19 (d, J=7.2 Hz, 2H), 2.15-2.08 (m, 1H), 2.00-1.89 (m, 1H), 1.81-1.58 (m, 4H), 1.22-1.06 (m, 2H).

Palbocicilb

Palbociclib, also referred to as 6-acetyl-8-cyclopentyl-5-methyl-2-{[5-(piperazin-1-yl)pyridin-2-yl]amino}pyrido[2,3-d]pyrimidin-7(8H)-one, has the following structural formula:

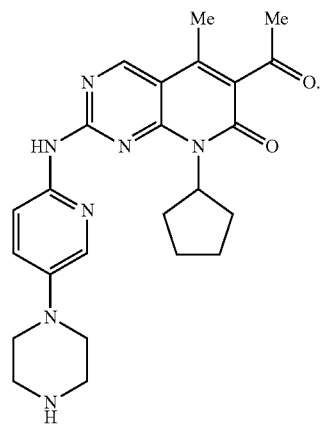

Palbociclib is an inhibitor of cyclin-dependent kinases (CDK) 4 and 6. Cyclin D1 and CDK4/6 are downstream of signaling pathways which lead to cellular proliferation. In vitro palbociclib reduced cellular proliferation of estrogen receptor (ER)-positive breast cancer cell lines by blocking progression of the cells from G1 into S phase of the cell cycle. Treatment of breast cancer cell lines with the combination of palbociclib and anti-estrogens leads to decreased retinoblastoma (Rb) protein phosphorylation resulting in reduced E2F expression and signaling, and increased growth arrest compared to treatment with each drug alone. In vitro treatment of ER-positive breast cancer cell lines with the combination of palbociclib and anti-estrogens led to increased cell senescence compared to each drug alone, which was sustained for up to 6 days following palbociclib removal and was greater if anti-estrogen treatment was continued. In vivo studies using a patient-derived ER-positive breast cancer xenograft model demonstrated that the combination of palbociclib and letrozole increased the inhibition of Rb phosphorylation, downstream signaling, and tumor growth compared to each drug alone.

Human bone marrow mononuclear cells treated with palbociclib in the presence or absence of an anti-estrogen in vitro did not become senescent and resumed proliferation following palbociclib withdrawal.

In one embodiment, this application pertains to any of the methods for treating and/or preventing breast cancer disclosed herein, wherein the method comprises co-administering to a subject in need thereof a therapeutically effective amount of a compound of Formula (I) or pharmaceutically acceptable salt thereof and a therapeutically effective amount of a CDK4/6 inhibitor or pharmaceutically acceptable salt thereof, or co-administering to a subject in need thereof a therapeutically effective amount of a combination of a compound of Formula (I-c) or pharmaceutically acceptable salt thereof and a CDK4/6 inhibitor or pharmaceutically acceptable salt thereof. In one embodiment, the compound of Formula (I-c) is a free base or pharmaceutically acceptable salt thereof. In one embodiment, the CDK4/6 inhibitor is a free base or pharmaceutically acceptable salt thereof. In one embodiment, the CDK4/6 inhibitor is palbociclib or a pharmaceutically acceptable salt thereof. In one embodiment, the CDK4/6 inhibitor is palbociclib dihydrochloride salt. The dihydrochloride salt of palbociclib can be prepared, for example, by reaction of the palbociclib free base in an ethereal solution of hydrogen chloride. Palbociclib is a commercially available drug for the treatment of breast cancer developed by Pfizer and sold under the brand name Ibrance®.

Methods of Ubiquitinating/Degrading a Target Protein in a Cell

The present invention provides a method of ubiquitinating/degrading a target protein (e.g. an intracellular target protein) in a cell. The method comprises administering a bifunctional compound comprising an E3 ubiquitin ligase binding moiety and a protein targeting moiety, preferably linked through a linker moiety, wherein the E3 ubiquitin ligase binding moiety recognizes a ubiquitin pathway protein (e.g., a ubiquitin ligase, preferably an E3 ubiquitin ligase) and the protein targeting moiety recognizes the target protein (e.g. the intracellular target protein) such that ubiquitination of the target protein occurs when the target protein is placed in proximity to the E3 ubiquitin ligase, resulting in degradation of the target protein via the proteasomal pathway and effecting the control (e.g. reduction) of the target protein level. In an embodiment the protein targeting moiety binds to a nuclear hormone receptor. In certain embodiments the protein targeting moiety binds to an estrogen receptor or an estrogen-related receptor. In an embodiment the intracellular target protein is an estrogen receptor or an estrogen-related receptor. In an embodiment, the linker moiety is a bond or a chemical group covalently coupling the protein targeting moiety to the E3 ubiquitin ligase binding moiety. In a certain embodiment, the linker may contain one or more alkanes, and one or more heterocyclic moieties. In a certain embodiment, the alkane is a $C_1$-$C_6$ alkyl group, and the heterocyclic moiety is pyrrolidine, imidazolidine, piperidine, or piperazine. In an embodiment, the E3 ubiquitin ligase is cereblon. In a certain embodiment, the cereblon binding moiety is thalidomide, lenalidomide, pomalidomide, an analog thereof, an isostere thereof, or a derivative thereof. The control (e.g., reduction) of protein levels afforded by the present invention provides treatment of a disease state or condition, which is modulated through the target protein by lowering the level of that protein in cells of a patient.

In one embodiment, the present invention is directed to a method of treating a patient in need thereof for a disease state or condition causally related to a protein where the degradation of that protein will produce a therapeutic effect in that patient, the method comprising administering to a patient in need an effective amount of a compound according to the present invention, optionally in combination with another bioactive agent. The disease state or condition may be a disease state or condition causally related to expression or overexpression of a protein.

Methods of Treatment

In one aspect, the present application pertains to a method of treating and/or preventing cancer comprising administering to a subject in need thereof a therapeutically effective amount of a compound of Formula (I), or a pharmaceutically acceptable salt, enantiomer, stereoisomer, solvate, polymorph, isotopic derivative, or prodrug thereof.

The methods of treating cancer described herein include a reduction in tumor size. Alternatively, or in addition, the cancer is metastatic cancer and this method of treatment includes inhibition of metastatic cancer cell invasion.

In one embodiment, the cancer is breast cancer.

In one embodiment, the breast cancer is metastatic breast cancer.

In one embodiment, the breast cancer is locally advanced breast cancer.

In one embodiment, the breast cancer is ER+, HER2− breast cancer.

In one embodiment, the breast cancer is metastatic, ER+, HER2− breast cancer.

In one embodiment, the breast cancer is metastatic, ER+, HER2− breast cancer that is also locally advanced.

In one aspect, the application pertains to treating breast cancer with a compound of Formula (I), wherein the compound of Formula (I) refers to a compound with the following structure:

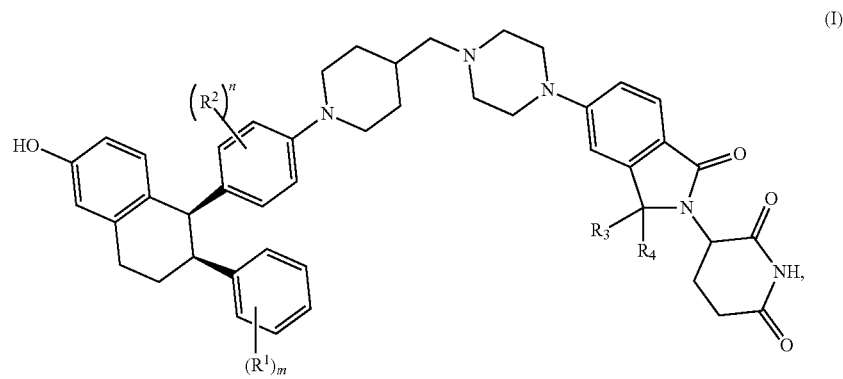

or a pharmaceutically acceptable salt, enantiomer, stereoisomer, solvate, polymorph, isotopic derivative, or prodrug thereof, wherein $R^1$, $R^2$, $R_3$, $R_4$, m, and n are defined herein.

In one embodiment, the breast cancer is metastatic breast cancer. In one embodiment, the breast cancer is locally advanced breast cancer. In one embodiment, the breast cancer is ER+, HER2-. In one embodiment, the breast cancer is metastatic, ER+, HER2- breast cancer. In one embodiment, the breast cancer is metastatic, ER+, HER2- breast cancer that is locally advanced.

In one aspect, the application pertains to treating breast cancer with a compound of Formula (I), wherein the compound of Formula (I) is selected from the group consisting of:

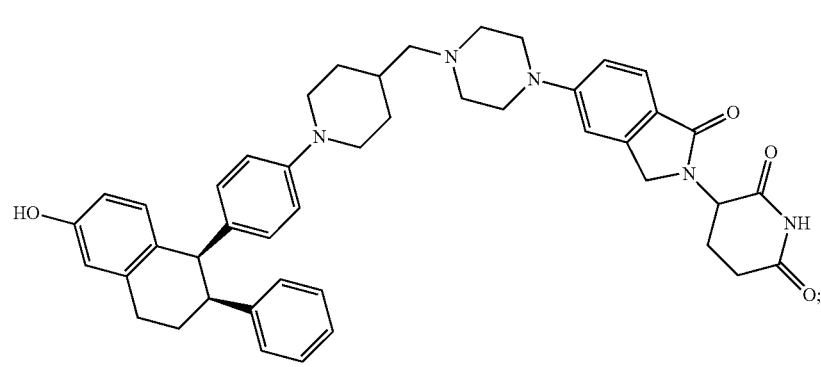
(I-a)

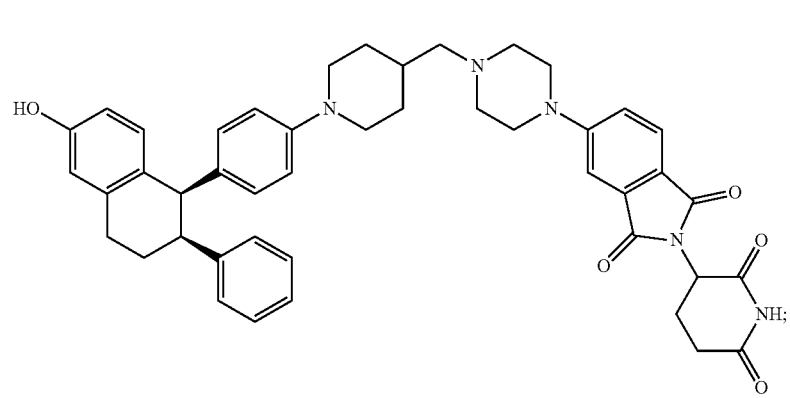
(I-b)

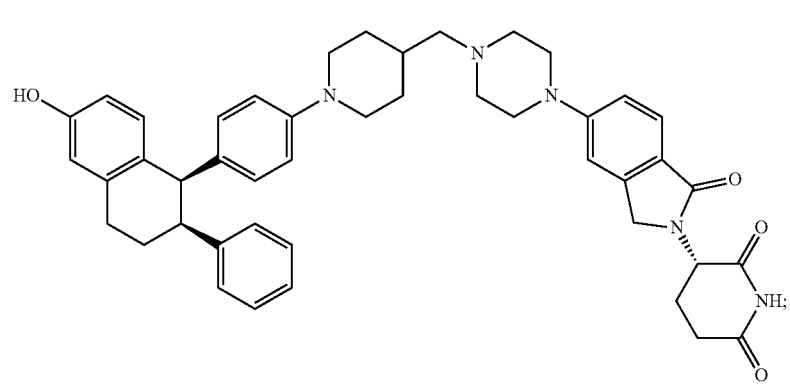
(I-c)

(I-d)
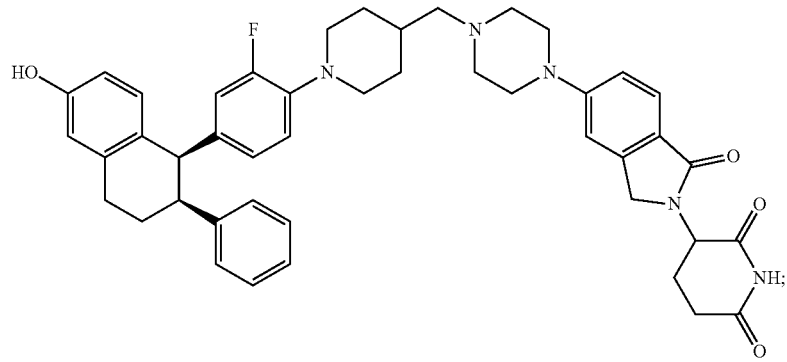
(I-e)
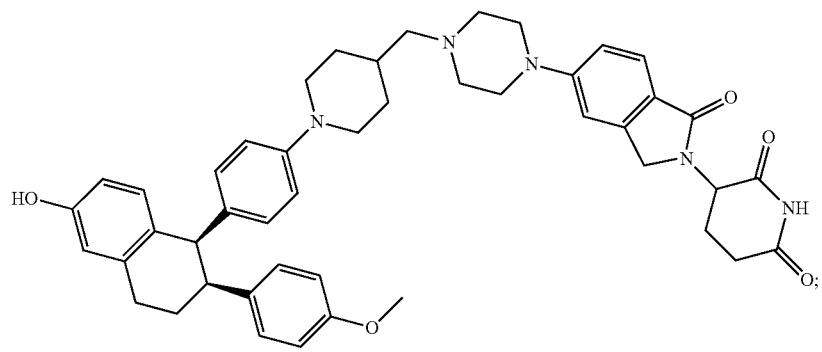
(I-f)
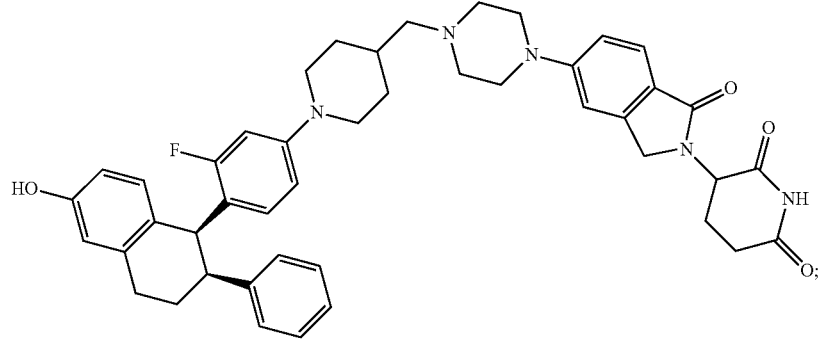
(I-g)
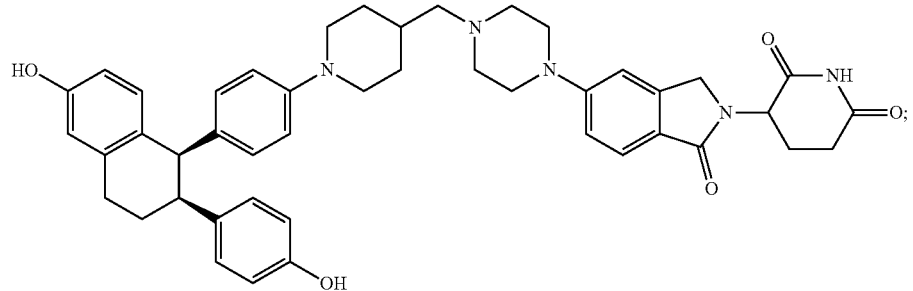

-continued

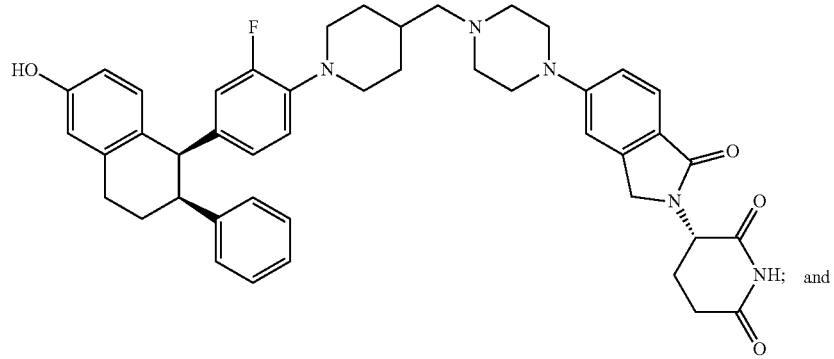
(I-h)

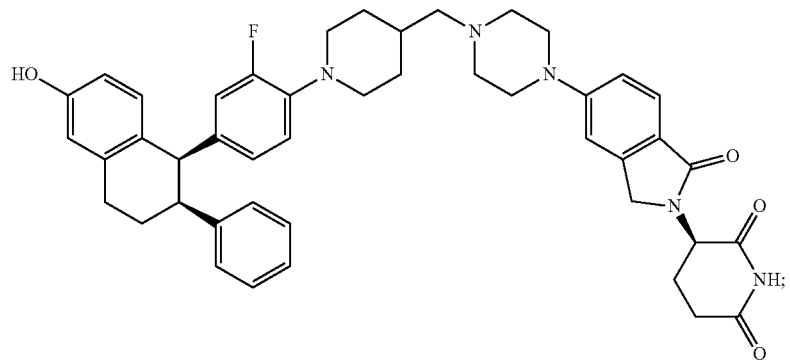
(I-i)

or a pharmaceutically acceptable salt, enantiomer, stereoisomer, solvate, polymorph, isotopic derivative, or prodrug thereof. In one embodiment, the compound of Formula (I) is a compound of Formula (I-c). In one embodiment, the breast cancer is metastatic breast cancer. In one embodiment, the breast cancer is locally advanced breast cancer. In one embodiment, the breast cancer is ER+, HER2−. In one embodiment, the breast cancer is metastatic, ER+, HER2− breast cancer. In one embodiment, the breast cancer is metastatic, ER+, HER2− breast cancer that is locally advanced.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active agent or compound. In another preferred aspect, an increase in average survival time of a population may also be measured, for example, by calculating for a population the average length of survival following completion of a first round of treatment with an active agent or compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active agent or compound. In another preferred aspect, an increase in average survival time of a population may also be measured, for example, by calculating for a population the average length of survival following completion of a first round of treatment with a compound of Formula (I).

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

The dosages of a compound of Formula (I) for any of the methods and uses described herein vary depending on the agent, the age, weight, and clinical condition of the recipient subject, and the experience and judgment of the clinician or practitioner administering the therapy, among other factors affecting the selected dosage.

The therapeutically effective amount of a compound of Formula (I) may be administered one, two, three, four, five, or more times over a day for 5, 10, 15, 30, 60, 90, 120, 150, 180 or more days, followed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more days of non-administration of a compound of Formula (I). This type of treatment schedule, i.e., administration of a compound of Formula (I) on consecutive days followed by non-administration of a compound of Formula (I) on consecutive days may be referred to as a treatment cycle.

In one embodiment, the therapeutically effective amount of a compound of Formula (I) may be administered one or two times over a day for up to 5, 10, 15, 20, 25, or 30 days, followed by 1, 2, 3, 4, 5, 6, 7, 8, 9, or 10 days of non-administration of a compound of Formula (I).

In one embodiment, the therapeutically effective amount of a compound of Formula (I) may be administered once day for up to 5, 10, 15, 20, 25, or 30 days followed by 1, 2, 3, 4, 5, 6, 7, 8, 9, or 10 days of non-administration of a compound of Formula (I).

In one embodiment, a treatment cycle involving the compound of Formula (I) may be repeated as many times as necessary to achieve the intended affect.

In one embodiment, the therapeutically effective amount of a compound of Formula (I) is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, thirty consecutive days, or for 2 months, 3 months, 4 months, 5 months, 6 months, or longer, in single or divided doses.

In one embodiment, the therapeutically effective amount of a compound of Formula (I) is about 30 mg, about 60 mg, about 90 mg, about 120 mg, about 150 mg, about 180 mg, about 210 mg, about 240 mg, about 270 mg, about 300 mg, about 330 mg, about 360 mg, about 390 mg, about 420 mg, about 450 mg, about 480 mg, about 510 mg, about 540 mg, about 570 mg, about 600 mg, about 630 mg, about 660 mg, about 690 mg, about 720 mg, about 750 mg, about 780 mg, about 810 mg, about 840 mg, about 870 mg, about 900 mg, about 930 mg, about 960 mg, or about 990 mg administered once, twice, three times, four times, or more daily in single or divided doses (which dose may be adjusted for the patient's weight in kg, body surface area in $m^2$, and age in years).

In one embodiment, the therapeutically effective amount of a compound of Formula (I) is about 30 mg to about 1000 mg administered once, twice, three times, four times, or more daily in single or divided doses (which dose may be adjusted for the patient's weight in kg, body surface area in $m^2$, and age in years).

In one embodiment, the therapeutically effective amount of a compound of Formula (I) is about 10 to about 40 mg, about 20 to about 50 mg, about 30 to about 60 mg, about 40 to about 70 mg, about 50 to about 80 mg, about 60 to about 90 mg, about 70 to about 100 mg, about 80 to about 110 mg, about 90 to about 120 mg, about 100 to about 130 mg, about 110 to about 140 mg, about 120 to about 150 mg, about 130 to about 160 mg, about 140 to about 170 mg, about 150 to about 180 mg, about 160 to about 190 mg, about 170 to about 200 mg, about 180 to about 210 mg, about 190 to about 220 mg, about 200 to about 230 mg, about 210 to about 240 mg, about 220 to about 250 mg, about 230 to about 260 mg, about 240 to about 270 mg, about 250 to about 280 mg, about 260 to about 290 mg, about 270 to about 300 mg, about 280 to about 310 mg, about 290 to about 320 mg, about 300 to about 330 mg, about 310 to about 340 mg, about 320 to about 350 mg, about 330 to about 360 mg, about 340 to about 370 mg, about 350 to about 380 mg, about 360 to about 390 mg, about 370 to about 400 mg, about 380 to about 410 mg, about 390 to about 420 mg, about 400 to about 430 mg, about 410 to about 440 mg, about 420 to about 450 mg, about 430 to about 460 mg, about 440 to about 470 mg, about 450 to about 480 mg, about 460 to about 490 mg, about 470 to about 500 mg, about 480 to about 510 mg, about 490 to about 520 mg, about 500 to about 530 mg, about 510 to about 540 mg, about 520 to about 550 mg, about 530 to about 560 mg, about 540 to about 570 mg, about 550 to about 580 mg, about 560 to about 590 mg, about 570 to about 600 mg, about 580 to about 610 mg, about 590 to about 620 mg, about 600 to about 630 mg, about 610 to about 640 mg, about 620 to about 650 mg, about 630 to about 660 mg, about 640 to about 670 mg, about 650 to about 680 mg, about 660 to about 690 mg, about 670 to about 700 mg, about 680 to about 710 mg, about 690 to about 720 mg, about 700 to about 730 mg, about 710 to about 740 mg, about 720 to about 750 mg, about 730 to about 760 mg, about 740 to about 770 mg, about 750 to about 780 mg, about 760 to about 790 mg, about 770 to about 800 mg, about 780 to about 810 mg, about 790 to about 820 mg, about 800 to about 830 mg, about 810 to about 840 mg, about 820 to about 850 mg, about 830 to about 860 mg, about 840 to about 870 mg, about 850 to about 880 mg, about 860 to about 890 mg, about 870 to about 900 mg, about 880 to about 910 mg, about 890 to about 920 mg, about 900 to about 930 mg, about 910 to about 940 mg, about 920 to about 950 mg, about 930 to about 960 mg, about 940 to about 970 mg, about 950 to about 980 mg, about 960 to about 990 mg, or about 970 to about 1,000 mg administered once, twice, three times, four times, or more daily in single or divided doses (which dose may be adjusted for the patient's weight in kg, body surface area in m², and age in years).

The therapeutically effective amount of a compound of Formula (I) can also range from about 0.01 mg/kg per day to about 100 mg/kg per day. In an aspect, therapeutically effective amount of a compound of Formula (I) can range from about 0.05 mg/kg per day to about 10 mg/kg per day. In an aspect, therapeutically effective amount of a compound of Formula (I) can range from about 0.075 mg/kg per day to about 5 mg/kg per day. In an aspect, therapeutically effective amount of a compound of Formula (I) can range from about 0.10 mg/kg per day to about 1 mg/kg per day. In an aspect, therapeutically effective amount of a compound of Formula (I) can range from about 0.20 mg/kg per day to about 0.70 mg/kg per day.

In one embodiment, the therapeutically effective amount of a compound of Formula (I) is about 0.10 mg/kg per day, about 0.15 mg/kg per day, about 0.20 mg/kg per day, about 0.25 mg/kg per day, about 0.30 mg/kg per day, about 0.35 mg/kg per day, about 0.40 mg/kg per day, about 0.45 mg/kg per day, about 0.50 mg/kg per day, about 0.55 mg/kg per day, about 0.60 mg/kg per day, about 0.65 mg/kg per day, about 0.70 mg/kg per day, about 0.75 mg/kg per day, about 0.80 mg/kg per day, about 0.85 mg/kg per day, about 0.90 mg/kg per day, about 0.95 mg/kg per day, or about 1.00 mg/kg per day.

In one embodiment, the therapeutically effective amount of a compound of Formula (I) is about 1.05 mg/kg per day, about 1.10 mg/kg per day, about 1.15 mg/kg per day, about 1.20 mg/kg per day, about 1.25 mg/kg per day, about 1.30 mg/kg per day, about 1.35 mg/kg per day, about 1.40 mg/kg per day, about 1.45 mg/kg per day, about 1.50 mg/kg per day, about 1.55 mg/kg per day, about 1.60 mg/kg per day, about 1.65 mg/kg per day, about 1.70 mg/kg per day, about 1.75 mg/kg per day, about 1.80 mg/kg per day, about 1.85 mg/kg per day, about 1.90 mg/kg per day, about 1.95 mg/kg per day, or about 2.00 mg/kg per day.

In one embodiment, the therapeutically effective amount of a compound of Formula (I) is about 2 mg/kg per day, about 2.5 mg/kg per day, about 3 mg/kg per day, about 3.5 mg/kg per day, about 4 mg/kg per day, about 4.5 mg/kg per day, about 5 mg/kg per day, about 5.5 mg/kg per day, about 6 mg/kg per day, about 6.5 mg/kg per day, about 7 mg/kg per day, about 7.5 mg/kg per day, about 8.0 mg/kg per day, about 8.5 mg/kg per day, about 9.0 mg/kg per day, about 9.5 mg/kg per day, or about 10 mg/kg per day.

In one embodiment, the therapeutically effective amount of a compound of Formula (I) is administered to the subject once daily. In one embodiment, this daily dose of a compound of Formula (I) is administered to the subject all at once. In one embodiment, this daily dose of a compound of Formula (I) is administered to the subject in two portions (a divided dose). In one embodiment, this daily dose of a compound of Formula (I) is administered to the subject in three portions. In one embodiment, this daily dose of a compound of Formula (I) is administered to the subject in four portions. In one embodiment, this daily dose of a compound of Formula (I) is administered to the subject in five or more portions. In one embodiment, these portions are administered to the subject at regular intervals throughout the day, for example, every 12 hours, every 8 hours, every 6 hours, every 5 hours, every 4 hours, etc.

In one embodiment, the therapeutically effective amount of the compound of Formula (I) results in a mean day 15 $AUC_{TAU}$ of greater than about 3,500 ng*hr/mL, about 3,550 ng*hr/mL, about 3,600 ng*hr/mL, about 3,650 ng*hr/mL, about 3,700 ng*hr/mL, about 3,750 ng*hr/mL, about 3,800 ng*hr/mL, about 3,850 ng*hr/mL, about 3,900 ng*hr/mL, about 3,950 ng*hr/mL, about 4,000 ng*hr/mL, about 4,050 ng*hr/mL, about 4,100 ng*hr/mL, about 4,150 ng*hr/mL, about 4,200 ng*hr/mL, about 4,250 ng*hr/mL, about 4,300 ng*hr/mL, about 4,350 ng*hr/mL, 4,400 ng*hr/mL, about 4,450 ng*hr/mL, about 4,500 ng*hr/mL, about 4,550 ng*hr/mL, about 4,600 ng*hr/mL, about 4,650 ng*hr/mL, about 4,700 ng*hr/mL, about 4,750 ng*hr/mL, about 4,800 ng*hr/mL, about 4,850 ng*hr/mL, about 4,900 ng*hr/mL, about 4,950 ng*hr/mL, or about 5,000 ng*hr/mL.

In one embodiment, the therapeutically effective amount of the compound of Formula (I) results in a mean day 15 $C_{max}$ of greater than about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, about 200 ng/mL, about 205 ng/mL, about 210 ng/mL, about 215 ng/mL, about 220 ng/mL, about 225 ng/mL, about 230 ng/mL, about 235 ng/mL, about 240 ng/mL, about 245 ng/mL, about 250 ng/mL, about 255 ng/mL, about 260 ng/mL, about 265 ng/mL, about 270 ng/mL, about 275 ng/mL, about 280 ng/mL, about 285 ng/mL, about 290 ng/mL, about 295 ng/mL, about 300 ng/mL, about 305 ng/mL, about 310 ng/mL, about 315 ng/mL, about 320 ng/mL, about 325 ng/mL, about 330 ng/mL, about 335 ng/mL, about 340 ng/mL, about 345 ng/mL, or about 350 ng/mL.

The therapeutically effective amount of a compound of Formula (I) can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of a compound of Formula (I) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Methods of Treatment Comprising Administering Compounds of Formula (I) and CDK4/6 Inhibitors In one aspect, the present application pertains to a method of treating and/or preventing breast cancer in a subject in need thereof comprising co-administering to the subject a therapeutically effective amount of a compound of Formula (I) and a therapeutically effective amount of a CDK4/6 inhibitor. These methods include a reduction in tumor size. Alternatively, or in addition, the breast cancer is metastatic breast cancer and this method of treatment includes inhibition of metastatic cancer cell invasion. In one embodiment, the breast cancer is metastatic breast cancer. In one embodiment, the breast cancer is locally advanced breast cancer. In one embodiment, the breast cancer is ER+, HER2−. In one embodiment, the breast cancer is metastatic, ER+, HER2− breast cancer. In one embodiment, the breast cancer is metastatic, ER+, HER2− breast cancer that is locally advanced.

In one embodiment, the therapeutically effective amount of a compound of Formula (I) and the therapeutically effective amount of a CDK4/6 inhibitor are administered simultaneously (either in the same formulation or in separate formulations).

In one embodiment, the therapeutically effective amount of a compound of Formula (I) and the therapeutically effective amount of a CDK4/6 inhibitor are administered sequentially, i.e., the compound of Formula (I) first, followed by the CDK4/6 inhibitor; or the CDK4/6 inhibitor first, followed by the compound of Formula (I). In one embodiment, the CDK4/6 inhibitor is administered first, followed by the compound of Formula (I) one hour later.

In one embodiment, the therapeutically effective amount of a compound of Formula (I) and the therapeutically effective amount of a CDK4/6 inhibitor are administered in temporal proximity.

In some embodiments, "temporal proximity" means that administration of compound of Formula (I) occurs within a time period before or after the administration of the CDK inhibitor (e.g., palbociclib), such that the therapeutic effect of the compound of Formula (I) overlaps with the therapeutic effect of the CDK inhibitor (e.g., palbociclib). In some embodiments, the therapeutic effect of the compound of Formula (I) completely overlaps with the therapeutic effect of the CDK inhibitor (e.g., palbociclib). In some embodiments, "temporal proximity" means that administration of the compound of Formula (I) occurs within a time period before or after the administration of the CDK inhibitor (e.g., palbociclib), such that there is a synergistic effect between the compound of Formula (I) and the CDK inhibitor.

"Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

In one aspect, the application pertains to a method of treating and/or preventing breast cancer in a subject in need thereof, comprising administering to the subject a compound of Formula (I) and a CDK4/6 inhibitor, wherein the compound of Formula (I) refers to a compound with the following structure:

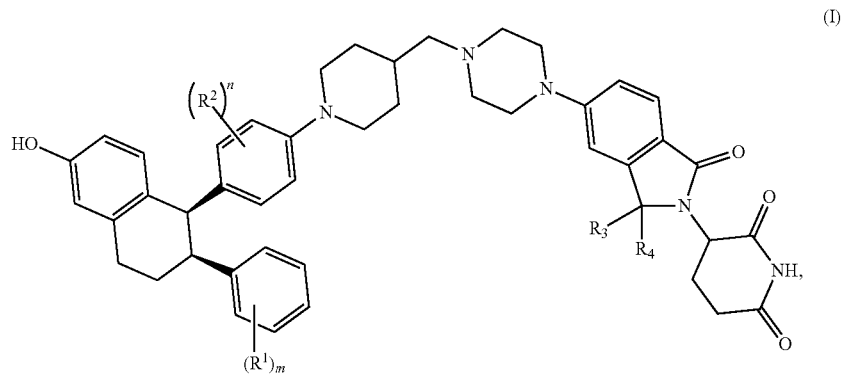

(I)

or a pharmaceutically acceptable salt, enantiomer, stereoisomer, solvate, polymorph, isotopic derivative, or prodrug thereof, wherein $R^1$, $R^2$, $R_3$, $R_4$, m, and n are defined herein, and the CDK4/6 inhibitor, or pharmaceutically acceptable salt thereof, is a compound that inhibits the enzyme in humans referred to as cyclin-dependent kinases (CDK) 4 and 6. In one embodiment, the CDK4/6 inhibitor is palbociclib, palbociclib dihydrochloride, or any other pharmaceutically acceptable salt thereof. In one embodiment, the breast cancer is metastatic breast cancer. In one embodiment, the breast cancer is locally advanced breast cancer. In one embodiment, the breast cancer is ER+, HER2−. In one embodiment, the breast cancer is metastatic, ER+, HER2− breast cancer. In one embodiment, the breast cancer is metastatic, ER+, HER2− breast cancer that is locally advanced.

In one aspect, the application pertains to a method of treating and/or preventing breast cancer in a subject in need thereof, comprising administering to the subject a therapeutically effective amount of a compound of Formula (I) and a CDK4/6 inhibitor, wherein the compound of Formula (I) is selected from the group consisting of:

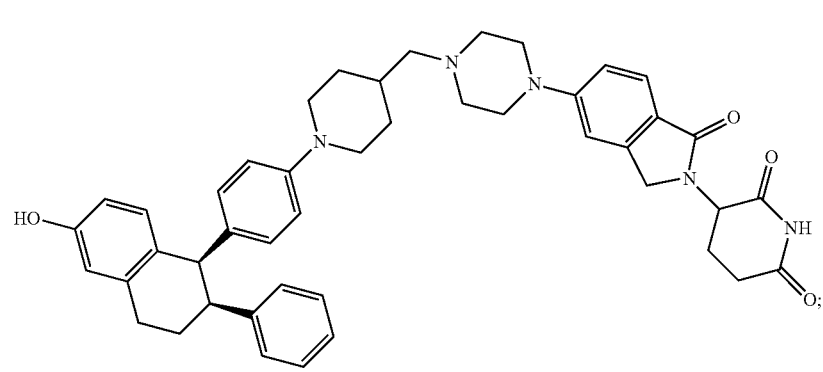

(I-a)

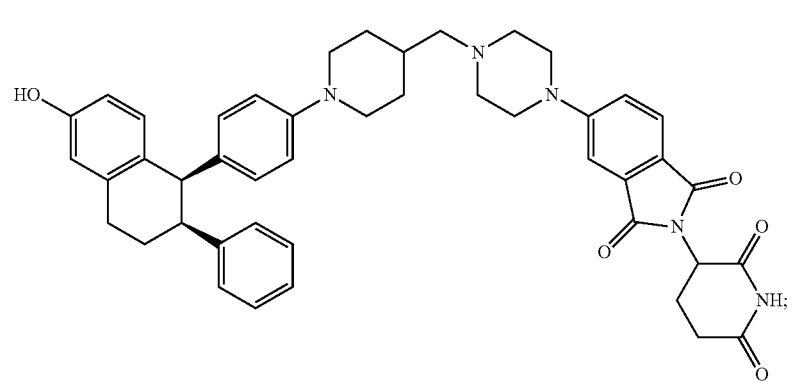

(I-b)

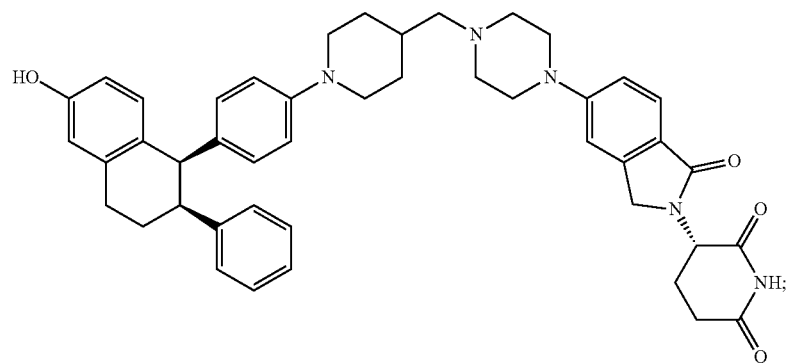
(I-c)
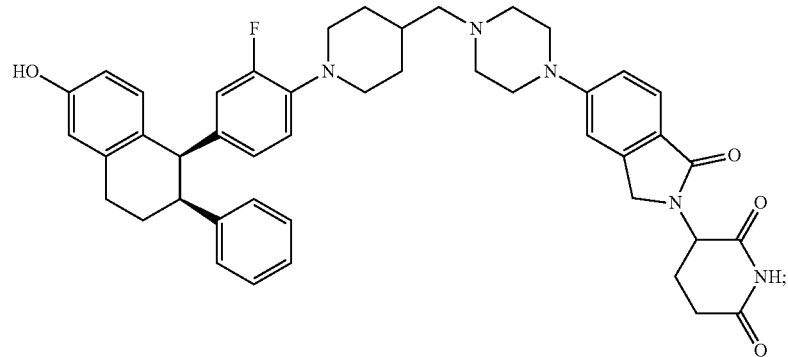
(I-d)
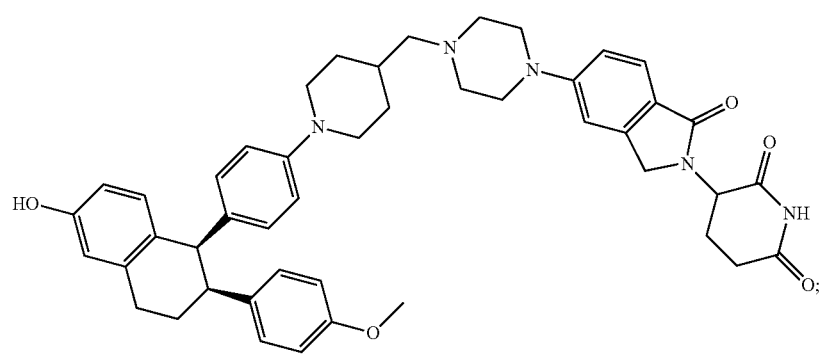
(I-e)
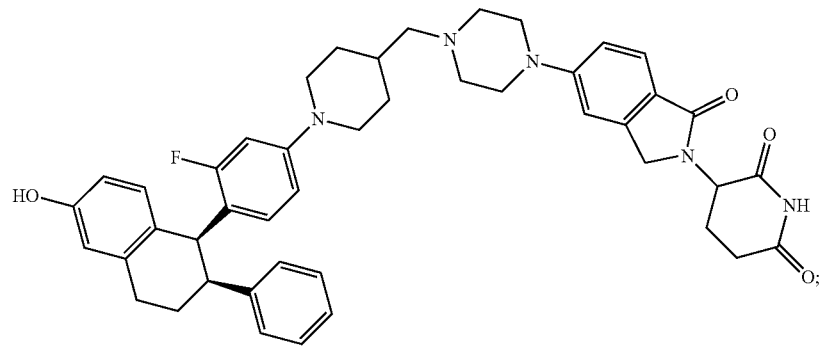
(I-f)

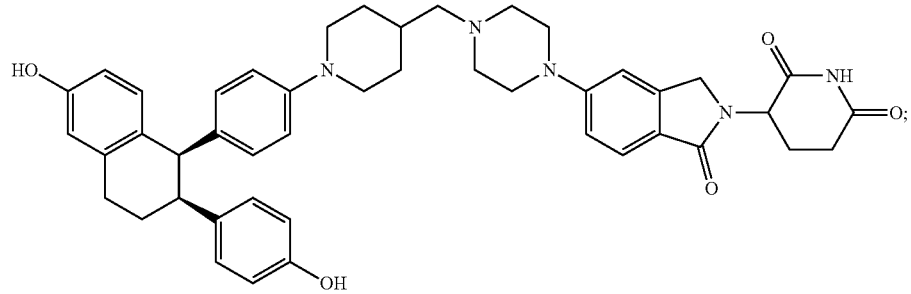

(I-g)

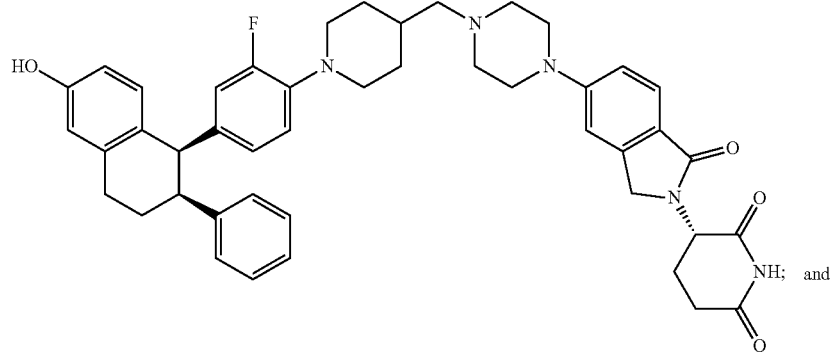

(I-h)

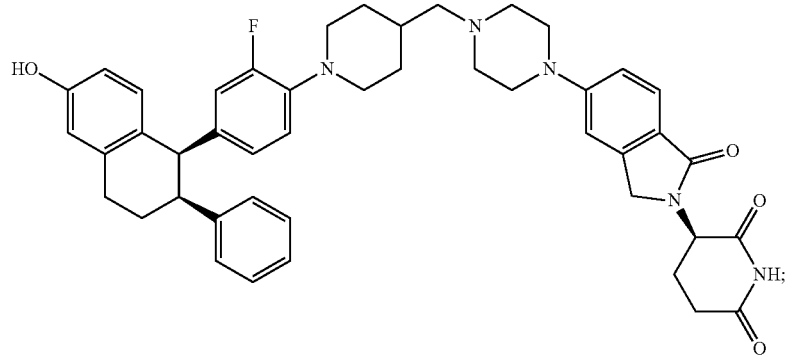

(I-i)

or a pharmaceutically acceptable salt, enantiomer, stereoisomer, solvate, polymorph, isotopic derivative, or prodrug thereof, and the CDK4/6 inhibitor is SHR6390, trilaciclib, lerociclib, AT7519M, dinaciclib, ribociclib, abemaciclib, or palbociclib, or any pharmaceutically acceptable salt thereof. In one embodiment, the compound of Formula (I) is a compound of Formula (I-c). In one embodiment, the breast cancer is metastatic breast cancer. In one embodiment, the breast cancer is locally advanced breast cancer. In one embodiment, the breast cancer is ER+, HER2−. In one embodiment, the breast cancer is metastatic, ER+, HER2− breast cancer. In one embodiment, the breast cancer is metastatic, ER+, HER2− breast cancer that is locally advanced.

In one aspect, the application pertains to a combined preparation of a compound of Formula (I) as defined herein and a CDK4/6 inhibitor as defined herein, for simultaneous, separate or sequential use in the treatment and/or prevention of breast cancer. In one embodiment, the breast cancer is metastatic breast cancer. In one embodiment, the breast cancer is locally advanced breast cancer. In one embodiment, the breast cancer is ER+, HER2−. In one embodiment, the breast cancer is metastatic, ER+, HER2− breast cancer.

In one embodiment, the breast cancer is metastatic, ER+, HER2− breast cancer that is locally advanced.

In one aspect, the application pertains to a combined preparation of a compound of Formula (I-c) as defined herein and a CDK4/6 inhibitor as defined herein, for simultaneous, separate or sequential use in the treatment and/or prevention of breast cancer. In one embodiment, the breast cancer is metastatic breast cancer. In one embodiment, the breast cancer is locally advanced breast cancer. In one embodiment, the breast cancer is ER+, HER2−. In one embodiment, the breast cancer is metastatic, ER+, HER2− breast cancer. In one embodiment, the breast cancer is metastatic, ER+, HER2− breast cancer that is locally advanced.

In one aspect, the application pertains to a combined preparation of a compound of Formula (I) as defined herein and palbocicilb inhibitor as defined herein, for simultaneous, separate or sequential use in the treatment and/or prevention of breast cancer. In one embodiment, the breast cancer is metastatic breast cancer. In one embodiment, the breast cancer is locally advanced breast cancer. In one embodiment, the breast cancer is ER+, HER2−. In one embodiment, the breast cancer is metastatic, ER+, HER2− breast cancer.

In one embodiment, the breast cancer is metastatic, ER+, HER2– breast cancer that is locally advanced.

In one aspect, the application pertains to a combined preparation of a compound of Formula (I-c) as defined herein and palbocicilb inhibitor as defined herein, for simultaneous, separate or sequential use in the treatment and/or prevention of breast cancer. In one embodiment, the breast cancer is metastatic breast cancer. In one embodiment, the breast cancer is locally advanced breast cancer. In one embodiment, the breast cancer is ER+, HER2–. In one embodiment, the breast cancer is metastatic, ER+, HER2– breast cancer. In one embodiment, the breast cancer is metastatic, ER+, HER2– breast cancer that is locally advanced.

In one aspect, treating cancer with a compound of Formula (I) and a CDK4/6 inhibitor results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer with a compound of Formula (I) and a CDK4/6 inhibitor results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer with a compound of Formula (I) and a CDK4/6 inhibitor results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer with a compound of Formula (I) and a CDK4/6 inhibitor results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer with a compound of Formula (I) and a CDK4/6 inhibitor results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active agent or compound. In another preferred aspect, an increase in average survival time of a population may also be measured, for example, by calculating for a population the average length of survival following completion of a first round of treatment with an active agent or compound.

In another aspect, treating cancer with a compound of Formula (I) and a CDK4/6 inhibitor results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active agent or compound. In another preferred aspect, an increase in average survival time of a population may also be measured, for example, by calculating for a population the average length of survival following completion of a first round of treatment with a compound of Formula (I) and a CDK4/6 inhibitor.

In another aspect, treating cancer with a compound of Formula (I) and a CDK4/6 inhibitor results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer with a compound of Formula (I) and a CDK4/6 inhibitor results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter or volume of a tumor after a prior tumor shrinkage that followed treatment.

In another preferred aspect, a decrease in tumor regrowth is indicated by failure of tumors to reoccur after treatment has stopped.

The dosages of a compound of Formula (I) and the CDK4/6 inhibitor for any of the methods and uses described herein vary depending on the agent, the age, weight, and clinical condition of the recipient subject, and the experience and judgment of the clinician or practitioner administering the therapy, among other factors affecting the selected dosage.

The therapeutically effective amount of the CDK4/6 inhibitor may be administered one, two, three, four, five, or more times over a day for 5, 10, 15, 30, 60, 90, 120, 150, 180 or more days, followed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more days of non-administration of the CDK4/6 inhibitor. This type of treatment schedule, i.e., administration of the CDK4/6 inhibitor on consecutive days followed by non-administration of the CDK4/6 inhibitor on consecutive days may be referred to as a treatment cycle.

In one embodiment, the therapeutically effective amount of the CDK4/6 inhibitor may be administered one or two times over a day for up to 5, 10, 15, 20, 25, or 30 days, followed by 1, 2, 3, 4, 5, 6, 7, 8, 9, or 10 days of non-administration of the CDK4/6 inhibitor.

In one embodiment, the therapeutically effective amount of the CDK4/6 inhibitor may be administered once day for up to 5, 10, 15, 20, 25, or 30 days followed by 1, 2, 3, 4, 5, 6, 7, 8, 9, or 10 days of non-administration of the CDK4/6 inhibitor.

In one embodiment, a treatment cycle involving the CDK4/6 inhibitor may be repeated as many times as necessary to achieve the intended affect.

In one embodiment, the treatment cycle with the CDK4/6 inhibitor is the same as the treatment cycle with the compound of formula (I).

In one embodiment, the treatment cycle with the CDK4/6 inhibitor is different than the treatment cycle with the compound of formula (I).

The therapeutically effective amount of a compound of Formula (I) and the CDK4/6 inhibitor may be administered one or more times over a day for up to 30 or more days, followed by 1 or more days of non-administration of a compound of Formula (I) and/or the CDK4/6 inhibitor. This type of treatment schedule, i.e., administration of a compound of Formula (I) and/or the CDK4/6 inhibitor on consecutive days followed by non-administration of a compound of Formula (I) and/or the CDK4/6 inhibitor on consecutive days, may be referred to as a treatment cycle or a cycle. In one embodiment, a treatment cycle may be repeated one, two, three, four, five, six, seven, eight, nine, ten, or more times. In one embodiment, a treatment cycle of a CDK4/6 inhibitor may be repeated as many times as necessary to achieve the intended affect.

In one embodiment, for the methods disclosed herein comprising administering a compound of Formula (I) and a CDK4/6 inhibitor, the therapeutically effective amount of a compound of Formula (I) is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, thirty consecutive days, or for 2 months, 3 months, 4 months, 5 months, 6 months, or longer, in single or divided doses.

In one embodiment, for the methods disclosed herein comprising administering a compound of Formula (I) and a CDK4/6 inhibitor, the therapeutically effective amount of a compound of Formula (I) is about 30 mg, about 60 mg, about 90 mg, about 120 mg, about 150 mg, about 180 mg, about 210 mg, about 240 mg, about 270 mg, about 300 mg, about 330 mg, about 360 mg, about 390 mg, about 420 mg, about 450 mg, about 480 mg, about 510 mg, about 540 mg, about 570 mg, about 600 mg, about 630 mg, about 660 mg, about 690 mg, about 720 mg, about 750 mg, about 780 mg, about 810 mg, about 840 mg, about 870 mg, about 900 mg, about 930 mg, about 960 mg, or about 990 mg administered once, twice, three times, four times, or more daily in single or divided doses (which dose may be adjusted for the patient's weight in kg, body surface area in $m^2$, and age in years).

In one embodiment, for the methods disclosed herein comprising administering a compound of Formula (I) and a CDK4/6 inhibitor, the therapeutically effective amount of a compound of Formula (I) is about 30 mg to about 1000 mg administered once, twice, three times, four times, or more daily in single or divided doses (which dose may be adjusted for the patient's weight in kg, body surface area in $m^2$, and age in years).

In one embodiment, for the methods disclosed herein comprising administering a compound of Formula (I) and a CDK4/6 inhibitor, the therapeutically effective amount of a compound of Formula (I) is about 10 to about 40 mg, about 20 to about 50 mg, about 30 to about 60 mg, about 40 to about 70 mg, about 50 to about 80 mg, about 60 to about 90 mg, about 70 to about 100 mg, about 80 to about 110 mg, about 90 to about 120 mg, about 100 to about 130 mg, about 110 to about 140 mg, about 120 to about 150 mg, about 130 to about 160 mg, about 140 to about 170 mg, about 150 to about 180 mg, about 160 to about 190 mg, about 170 to about 200 mg, about 180 to about 210 mg, about 190 to about 220 mg, about 200 to about 230 mg, about 210 to about 240 mg, about 220 to about 250 mg, about 230 to about 260 mg, about 240 to about 270 mg, about 250 to about 280 mg, about 260 to about 290 mg, about 270 to about 300 mg, about 280 to about 310 mg, about 290 to about 320 mg, about 300 to about 330 mg, about 310 to about 340 mg, about 320 to about 350 mg, about 330 to about 360 mg, about 340 to about 370 mg, about 350 to about 380 mg, about 360 to about 390 mg, about 370 to about 400 mg, about 380 to about 410 mg, about 390 to about 420 mg, about 400 to about 430 mg, about 410 to about 440 mg, about 420 to about 450 mg, about 430 to about 460 mg, about 440 to about 470 mg, about 450 to about 480 mg, about 460 to about 490 mg, about 470 to about 500 mg, about 480 to about 510 mg, about 490 to about 520 mg, about 500 to about 530 mg, about 510 to about 540 mg, about 520 to about 550 mg, about 530 to about 560 mg, about 540 to about 570 mg, about 550 to about 580 mg, about 560 to about 590 mg, about 570 to about 600 mg, about 580 to about 610 mg, about 590 to about 620 mg, about 600 to about 630 mg, about 610 to about 640 mg, about 620 to about 650 mg, about 630 to about 660 mg, about 640 to about 670 mg, about 650 to about 680 mg, about 660 to about 690 mg, about 670 to about 700 mg, about 680 to about 710 mg, about 690 to about 720 mg, about 700 to about 730 mg, about 710 to about 740 mg, about 720 to about 750 mg, about 730 to about 760 mg, about 740 to about 770 mg, about 750 to about 780 mg, about 760 to about 790 mg, about 770 to about 800 mg, about 780 to about 810 mg, about 790 to about 820 mg, about 800 to about 830 mg, about 810 to about 840 mg, about 820 to about 850 mg, about 830 to about 860 mg, about 840 to about 870 mg, about 850 to about 880 mg, about 860 to about 890 mg, about 870 to about 900 mg, about 880 to about 910 mg, about 890 to about 920 mg, about 900 to about 930 mg, about 910 to about 940 mg, about 920 to about 950 mg, about 930 to about 960 mg, about 940 to about 970 mg, about 950 to about 980 mg, about 960 to about 990 mg, or about 970 to about 1,000 mg administered once, twice, three times, four times, or more daily in single or divided doses (which dose may be adjusted for the patient's weight in kg, body surface area in $m^2$, and age in years).

In one embodiment, for the methods disclosed herein comprising administering a compound of Formula (I) and a CDK4/6 inhibitor, the therapeutically effective amount of a compound of Formula (I) can also range from about 0.01 mg/kg per day to about 100 mg/kg per day, about 0.05 mg/kg per day to about 10 mg/kg per day, about 0.075 mg/kg per day to about 5 mg/kg per day, about 0.10 mg/kg per day to about 1 mg/kg per day, or about 0.20 mg/kg per day to about 0.70 mg/kg per day.

In one embodiment, for the methods disclosed herein comprising administering a compound of Formula (I) and a CDK4/6 inhibitor, the therapeutically effective amount of a compound of Formula (I) is about 0.10 mg/kg per day, about 0.15 mg/kg per day, about 0.20 mg/kg per day, about 0.25 mg/kg per day, about 0.30 mg/kg per day, about 0.35 mg/kg per day, about 0.40 mg/kg per day, about 0.45 mg/kg per day, about 0.50 mg/kg per day, about 0.55 mg/kg per day, about 0.60 mg/kg per day, about 0.65 mg/kg per day, about 0.70 mg/kg per day, about 0.75 mg/kg per day, about 0.80 mg/kg per day, about 0.85 mg/kg per day, about 0.90 mg/kg per day, about 0.95 mg/kg per day, or about 1.00 mg/kg per day.

In one embodiment, for the methods disclosed herein comprising administering a compound of Formula (I) and a CDK4/6 inhibitor, the therapeutically effective amount of a compound of Formula (I) is about 1.05 mg/kg per day, about 1.10 mg/kg per day, about 1.15 mg/kg per day, about 1.20 mg/kg per day, about 1.25 mg/kg per day, about 1.30 mg/kg per day, about 1.35 mg/kg per day, about 1.40 mg/kg per day, about 1.45 mg/kg per day, about 1.50 mg/kg per day, about 1.55 mg/kg per day, about 1.60 mg/kg per day, about 1.65 mg/kg per day, about 1.70 mg/kg per day, about 1.75 mg/kg per day, about 1.80 mg/kg per day, about 1.85 mg/kg per day, about 1.90 mg/kg per day, about 1.95 mg/kg per day, or about 2.00 mg/kg per day.

In one embodiment, for the methods disclosed herein comprising administering a compound of Formula (I) and a CDK4/6 inhibitor, the therapeutically effective amount of a compound of Formula (I) is about 2 mg/kg per day, about 2.5 mg/kg per day, about 3 mg/kg per day, about 3.5 mg/kg per day, about 4 mg/kg per day, about 4.5 mg/kg per day, about 5 mg/kg per day, about 5.5 mg/kg per day, about 6 mg/kg per day, about 6.5 mg/kg per day, about 7 mg/kg per day, about 7.5 mg/kg per day, about 8.0 mg/kg per day, about 8.5 mg/kg per day, about 9.0 mg/kg per day, about 9.5 mg/kg per day, or about 10 mg/kg per day.

In one embodiment, for the methods disclosed herein comprising administering a compound of Formula (I) and a CDK4/6 inhibitor, the therapeutically effective amount of a CDK4/6 inhibitor is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, thirty consecutive days, or, once, twice, three times, four times, or more daily, or for 2 months, 3 months, 4 months, 5 months, 6 months, or longer, in single or divided doses. In one embodiment, the CDK4/6 inhibitor is palbociclib.

In one embodiment, a compound of Formula (I) and palbociclib may be administered simultaneously. In one embodiment, a compound of Formula (I) is administered first, and palbociclib is administered second. In one embodiment, palbociclib is administered first and a compound of Formula (I) is administered second. For example, in some embodiments, the administration of a compound of Formula (I) and the administration of palbociclib is concomitant. In some embodiments, the administration of a compound of Formula (I) and the administration of palbociclib is sequential.

In one embodiment, the palbociclib is administered prior to the administration of a compound of Formula (I), such that the two compounds, and their respective excipients, do not mix in the subject's stomach. In one embodiment, the maximum time between the administration of the palbociclib and the administration of a compound of Formula (I) is such that the benefit of the combination is achieved. In one embodiment, palbociclib is administered at least 5, at least 10, at least 15, at least 20, at least 25, or at least 30 minutes before a compound of Formula (I) is administered. In one embodiment, palbociclib is administered between 5 and 35, between 10 and 40, between 15 and 25, between 20 and 50, between 25 and 55, or between 30 and 60 minutes before a compound of Formula (I) is administered. In one embodiment, palbociclib is administered between 30 and 60, between 30 and 70, between 30 and 80, between 30 and 90, between 30 and 120, between 30 and 180, between 30 and 240, between 30 and 300, between 30 and 360 minutes, between 30 and 480, between 30 and 600, or between 30 and 720 minutes before a compound of Formula (I) is administered.

In one embodiment, the palbociclib is administered after the administration of a compound of Formula (I), such that the two compounds, and their respective excipients (if present), do not mix in the subject's stomach. In one embodiment, the maximum time between the administration of the palbociclib and the administration of a compound of Formula (I) is such that the benefit of the combination is achieved. In one embodiment, palbociclib is administered at least 5, at least 10, at least 15, at least 20, at least 25, or at least 30 minutes after a compound of Formula (I) is administered. In one embodiment, palbociclib is administered between 5 and 35, between 10 and 40, between 15 and 25, between 20 and 50, between 25 and 55, or between 30 and 60 minutes after a compound of Formula (I) is administered. In one embodiment, palbociclib is administered between 30 and 60, between 30 and 70, between 30 and 80, between 30 and 90, between 30 and 120, between 30 and 180, between 30 and 240, between 30 and 300, between 30 and 360 minutes, between 30 and 480, between 30 and 600, or between 30 and 720 minutes after a compound of Formula (I) is administered.

In one embodiment, for the methods disclosed herein comprising administering a compound of Formula (I) and a CDK4/6 inhibitor, the therapeutically effective amount of a CDK4/6 inhibitor is 60 mg, 75 mg, 100 mg, or 125 mg administered once daily, in single or divided doses. In one embodiment, the therapeutically effective amount of a CDK4/6 inhibitor is administered once daily for 21 straight days, followed by 7 days of off treatment. In one embodiment, the CDK4/6 inhibitor is palbociclib.

The 21 straight days of treatment with a CDK4/6 inhibitor followed by 7 days of off treatment is referred to herein as a treatment cycle or cycle. In one embodiment, a treatment cycle of a CDK4/6 inhibitor may be repeated one, two, three, four, five, six, seven, eight, nine, ten, or more times. In one embodiment, a treatment cycle of a CDK4/6 inhibitor may be repeated as many times as necessary to achieve the intended affect. In one embodiment, the CDK4/6 inhibitor is palbociclib.

In one embodiment, for the methods disclosed herein comprising administering a compound of Formula (I) and a CDK4/6 inhibitor, the therapeutically effective amount of a CDK4/6 inhibitor is about 0.1 mg/kg per day, about 0.2 mg/kg per day, about 0.3 mg/kg per day, about 0.4 mg/kg per day, about 0.5 mg/kg per day, 0.6 mg/kg per day, about 0.7 mg/kg per day, about 0.8 mg/kg per day, about 0.9 mg/kg per day, about 1 mg/kg per day, about 1.1 mg/kg per day, about 1.2 mg/kg per day, about 1.3 mg/kg per day, about 1.4 mg/kg per day, about 1.5 mg/kg per day, 1.6 mg/kg per day, about 1.7 mg/kg per day, about 1.8 mg/kg per day, about 1.9 mg/kg per day, about 2 mg/kg per day, about 2.5 mg/kg per day, about 3 mg/kg per day, about 3.5 mg/kg per day, about 4 mg/kg per day, about 4.5 mg/kg per day, about 5 mg/kg per day, about 5.5 mg/kg per day, about 6 mg/kg per day, about 6.5 mg/kg per day, about 7 mg/kg per day, about 7.5 mg/kg per day, about 8.0 mg/kg per day, about 8.5 mg/kg per day, about 9.0 mg/kg per day, about 9.5 mg/kg per day, or about 10 mg/kg per day. In one embodiment, the CDK4/6 inhibitor is palbociclib.

In one embodiment, for the methods disclosed herein comprising administering a compound of Formula (I) and a CDK4/6 inhibitor, the therapeutically effective amount of a CDK4/6 inhibitor is about 0.5 mg/kg per day to about 3.0 mg/kg per day.

In one embodiment, for the methods disclosed herein comprising administering a compound of Formula (I) and a CDK4/6 inhibitor, the therapeutically effective amount of a compound of Formula (I) is administered to the subject once daily. In one embodiment, this daily dose of a compound of Formula (I) is administered to the subject all at once. In one embodiment, this daily dose of a compound of Formula (I) is administered to the subject in two portions (a divided dose). In one embodiment, this daily dose of a compound of Formula (I) is administered to the subject in three portions. In one embodiment, this daily dose of a compound of Formula (I) is administered to the subject in four portions. In one embodiment, this daily dose of a compound of Formula (I) is administered to the subject in five or more portions. In one embodiment, these portions are administered to the subject at regular intervals throughout the day, for example, every 12 hours, every 8 hours, every 6 hours, every 5 hours, every 4 hours, etc.

In one embodiment, for the methods disclosed herein comprising administering a compound of Formula (I) and a CDK4/6 inhibitor, the therapeutically effective amount of a CDK4/6 inhibitor is administered to the subject once daily. In one embodiment, this daily dose of a CDK4/6 inhibitor is administered to the subject all at once. In one embodiment, this daily dose of a CDK4/6 inhibitor is administered to the subject in two portions (a divided dose). In one embodiment, this daily dose of a CDK4/6 inhibitor is administered to the subject in three portions. In one embodiment, this daily dose of a CDK4/6 inhibitor is administered to the subject in four portions. In one embodiment, this daily dose of a CDK4/6 inhibitor is administered to the subject in five or more portions. In one embodiment, these portions are administered to the subject at regular intervals throughout the day, for example, every 12 hours, every 8 hours, every 6 hours, every 5 hours, every 4 hours, etc.

The therapeutically effective amount of a compound of Formula (I) and a CDK4/6 inhibitor can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of a compound of Formula (I) and/or a CDK4/6 inhibitor or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Pharmaceutical Compositions

The compounds of Formula (I) and CDK4/6 inhibitors can be administered according to the invention by any appropriate route, including oral, parenteral (subcutaneous, intramuscular, intravenous (bolus or infusion), depot, intraperitoneal), intrathecal, intranasal, intravaginal, sublingual, buccal, intraocular, or rectal.

In one embodiment, the compounds of Formula (I) and CDK4/6 inhibitors may be formulated into separate dosage forms. These separate dosage forms may be suitable for administration by any appropriate route, including, for example, oral, parenteral (subcutaneous, intramuscular, intravenous, depot), intrathecal, intranasal, intravaginal, sublingual, buccal, intraocular, or rectal.

In one embodiment, the compounds of Formula (I) and CDK4/6 inhibitors may be combined together and formulated into a single dosage form. This single dosage form may be suitable for administration by any appropriate route, including, for example, oral, parenteral (subcutaneous, intramuscular, intravenous, depot), intrathecal, intranasal, intravaginal, sublingual, buccal, intraocular, or rectal.

In one embodiment, the compounds of Formula (I) and CDK4/6 inhibitors may be formulated into separate dosage forms, each of which is suitable for oral administration. In one embodiment, the CDK4/6 inhibitor is SHR6390, trilaciclib, lerociclib, AT7519M, dinaciclib, ribociclib, abemaciclib, palbociclib, or any pharmaceutically acceptable salt thereof. In one embodiment, the CDK4/6 inhibitor is palbociclib, palbociclib dihydrochloride, or any other pharmaceutically acceptable salt of palbociclib.

In one embodiment, the compounds of Formula (I) and CDK4/6 inhibitors may be formulated into a single dosage form that is suitable for oral administration. In one embodiment, the CDK4/6 inhibitor is SHR6390, trilaciclib, lerociclib, AT7519M, dinaciclib, ribociclib, abemaciclib, palbociclib, or any pharmaceutically acceptable salt thereof. In one embodiment, the CDK4/6 inhibitor is palbociclib, palbociclib dihydrochloride, or any other pharmaceutically acceptable salt of palbociclib.

In one embodiment, the compounds of Formula (I) and CDK4/6 inhibitors are each formulated for oral administration, either separately or together. For example, in one embodiment, the compounds of Formula (I) and CDK4/6 inhibitor are both formulated, either separately or together, as tablets comprising zero, one, two, or more of each of the following: emulsifier, surfactant, binder, disintegrant, glidant, and lubricant, or alternatively, the compound of Formula (I) and the CDK4/6 inhibitor may be formulated separately or together in capsules or as oral liquids, or a combination thereof.

In one embodiment, the emulsifier is hypromellose.

In one embodiment, the surfactant is vitamin E polyethylene glycol succinate.

In one embodiment, the binder (also referred to herein as a filler) is selected from the group consisting of microcrystalline cellulose, lactose monohydrate, sucrose, glucose, and sorbitol.

In one embodiment, the disintegrant is croscarmellose sodium.

In one embodiment, the glidant refers to a substance used to promote powder flow by reducing interparticle cohesion.

In one embodiment, in the dosage forms of the disclosure, the glidant is selected from the group consisting of silicon dioxide, silica colloidal anhydrous, starch, and talc.

In one embodiment, the lubricant refers to a substance that prevents ingredients from sticking and/or clumping together in the machines used in preparation of the dosage forms of the disclosure. In one embodiment, in the dosage forms of the disclosure, the lubricant is selected from the group consisting of magnesium stearate, sodium stearyl fumarate, stearic acid, and vegetable stearin.

In some embodiments, this disclosure provides a liquid composition comprising a compound of Formula (I). In some embodiments, the liquid composition comprises a compound of Formula (I) and a surfactant. In some embodiments, the liquid composition comprises a compound of Formula (I) and a solvent. In some embodiments the composition comprises a therapeutically effective amount of a compound of Formula (I), a surfactant, and a solvent.

In some embodiments, this disclosure provides a liquid composition comprising a compound of Formula (I-c). In some embodiments, the liquid composition comprises a compound of Formula (I-c) and a surfactant. In some embodiments, the liquid composition comprises a compound of Formula (I-c) and a solvent. In some embodiments the composition comprises a therapeutically effective amount of a compound of Formula (I-c), a surfactant, and a solvent. In some embodiments, the ratio of the surfactant to the solvent in the composition is between 0.001 and 0.035 g surfactant to 1 mL solvent. In some embodiments, the ratio of the surfactant to the solvent in the composition is between 0.005 and 0.035 g surfactant to 1 mL solvent. In some embodiments, the ratio of surfactant to solvent in the composition is between 0.01 and 0.03 g surfactant to 1 mL solvent. In some embodiments, the ratio of surfactant to solvent in the composition is between 0.015 and 0.025 g surfactant to 1 mL solvent. In some embodiments, the ratio of surfactant to solvent in the composition is between 0.016 and 0.024 g surfactant to 1 mL solvent. In some embodiments, the ratio of surfactant to solvent in the composition is between 0.017 and 0.023 g surfactant to 1 mL solvent. In some embodiments, the ratio of surfactant to solvent in the composition is between 0.018 and 0.022 g surfactant to 1 mL solvent. In some embodiments, the ratio of surfactant to solvent in the composition is between 0.019 and 0.021 g surfactant to 1 mL solvent. In some embodiments, the ratio of surfactant to solvent in the composition is about 0.02 g surfactant to about 1 mL solvent. In some embodiments, the ratio of surfactant to solvent in the composition is 0.02 g surfactant to 1 mL solvent. In some embodiments, the surfactant is a sorbitan derivative. In some embodiments, the surfactant is Tween 80. In some embodiments, the solvent is a low molecular weight polyethylene glycol (PEG). In some embodiments, the solvent is polyethylene glycol (PEG)-400.

In some embodiments, this disclosure provides a liquid composition comprising a compound of Formula (I-c). In some embodiments, the liquid composition comprises a compound of Formula (I-c) and Tween 80. In some embodiments, the liquid composition comprises a compound of Formula (I-c) and polyethylene glycol (PEG)-400. In some embodiments the composition comprises a therapeutically effective amount of a compound of Formula (I-c), Tween 80, and PEG-400. In some embodiments, the ratio of Tween 80 to PEG-400 in the composition is between 0.001 and 0.035 g Tween 80 to 1 mL PEG-400. In some embodiments, the ratio of Tween 80 to PEG-400 in the composition is between 0.005 and 0.035 g Tween 80 to 1 mL PEG-400. In some embodiments, the ratio of Tween 80 to PEG-400 in the composition is between 0.01 and 0.03 g Tween 80 to 1 mL PEG-400. In some embodiments, the ratio of Tween 80 to PEG-400 in the composition is between 0.015 and 0.025 g Tween 80 to 1 mL PEG-400. In some embodiments, the ratio of Tween 80 to PEG-400 in the composition is between 0.016 and 0.024 g Tween 80 to 1 mL PEG-400. In some embodiments, the ratio of Tween 80 to PEG-400 in the composition is between 0.017 and 0.023 g Tween 80 to 1 mL PEG-400. In some embodiments, the ratio of Tween 80 to PEG-400 in the composition is between 0.018 and 0.022 g Tween 80 to 1 mL PEG-400. In some embodiments, the ratio of Tween 80 to PEG-400 in the composition is between 0.019 and 0.021 g Tween 80 to 1 mL PEG-400. In some embodiments, the ratio of Tween 80 to PEG-400 in the composition is about 0.02 g Tween 80 to about 1 mL PEG-400. In some embodiments, the ratio of Tween 80 to PEG-400 in the composition is 0.02 g Tween 80 to 1 mL PEG-400.

In some embodiments this disclosure provides a method of making a liquid composition comprising a surfactant, a solvent, and a compound of Formula (I-c) comprising the step of adding the solvent to a pre-aliquoted volume of the surfactant. In some embodiments, the method further comprises the step of adding a compound of Formula (I-c) to a mixture of the solvent and the surfactant. In some embodiments this disclosure provides a method of making a liquid composition comprising the steps of (i) adding the solvent to a pre-aliquoted volume of the surfactant and (ii) adding a compound of Formula (I-c) to a mixture of the solvent and the surfactant. In some embodiments, the surfactant is a sorbitan derivative. In some embodiments, the surfactant is Tween 80. In some embodiments, the solvent is a low molecular weight polyethylene glycol (PEG). In some embodiments, the solvent is polyethylene glycol (PEG)-400.

In some embodiments this disclosure provides a liquid composition comprising a surfactant, a solvent, and a compound of Formula (I-c) prepared by a method comprising the step of adding the solvent to a pre-aliquoted volume of the surfactant. In some embodiments, the method further comprises the step of adding a compound of Formula (I-c) to a mixture of the solvent and the surfactant. In some embodiments this disclosure provides a liquid composition comprising a surfactant, a solvent, and a compound of Formula (I-c) prepared by a method comprising the steps of (i) adding the solvent to a pre-aliquoted volume of the surfactant and (ii) adding a compound of Formula (I-c) to a mixture of the solvent and the surfactant. In some embodiments, the surfactant is a sorbitan derivative. In some embodiments, the surfactant is Tween 80. In some embodiments, the solvent is a low molecular weight polyethylene glycol (PEG). In some embodiments, the solvent is polyethylene glycol (PEG)-400.

The pharmaceutical compositions containing a compound of Formula (I) and CDK4/6 inhibitors (either separately or together) may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of a compound of Formula (I) into preparations that can be used pharmaceutically. Of course, the appropriate formulation is dependent upon the route of administration chosen.

Pharmaceutical compositions containing a compound of Formula (I) and CDK4/6 inhibitors (either separately or together) suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a compound of Formula (I) and/or CDK4/6 inhibitors in the required amount in an appropriate solvent with one or a combination of ingredients enumerated above, as required, followed by filtered sterilization. Generally, dispersions are prepared by incorporating the active agent or compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, a compound of Formula (I) and/or CDK4/6 inhibitors can be incorporated with excipients and used in the form of tablets, troches, or capsules. Oral compositions can also be prepared using a fluid carrier for use as a mouthwash, wherein the agent or compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, a compound of Formula (I) and/or CDK4/6 inhibitors are delivered in the form of an aerosol spray from pressured container or dispenser, which contains a suitable propellant, e.g., a gas such as carbon dioxide, or a nebulizer.

Systemic administration of a compound of Formula (I) and/or CDK4/6 inhibitors can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents or compounds are formulated into ointments, salves, gels, or creams as generally known in the art.

In one aspect, a compound of Formula (I) and/or CDK4/6 inhibitors is/are prepared with pharmaceutically acceptable carriers that will protect the agent or compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions of a compound of Formula (I) and/or CDK4/6 inhibitors in dosage unit form for ease of administration and uniformity of dosage. Dosage unit form as used herein refers to physically discrete units suited as unitary dosages for the subject to be treated; each unit containing a predetermined quantity of active agent or compound calculated to produce the desired therapeutic effect in association with the required pharmaceutical carrier. The specification for the dosage unit forms of the application are dictated by and directly dependent on the unique characteristics of a compound of Formula (I) and the particular therapeutic effect to be achieved.

The pharmaceutical compositions of a compound of Formula (I) and/or CDK4/6 inhibitors can be included in a container, pack, or dispenser together with instructions for administration.

Illustrative modes of administration for a compound of Formula (I) and/or CDK4/6 inhibitors includes systemic or local administration such as oral, nasal, parenteral, transdermal, subcutaneous, vaginal, buccal, rectal or topical administration modes. In one embodiment, the compound of Formula (I), or a pharmaceutically acceptable salt or hydrate thereof, is administered orally. In one embodiment, the compound of Formula (I) is administered as a tablet, capsule, caplet, solution, suspension, syrup, granule, bead, powder, or pellet.

Illustrative pharmaceutical compositions are tablets and gelatin capsules comprising a salt of compound of Formula (I) and/or CDK4/6 inhibitors and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the salt such as cyclodextrin, hydroxypropyl-cyclodextrin, PEG400, and/or PEG200.

For preparing pharmaceutical compositions from a compound of Formula (I) and/or CDK4/6 inhibitors, or any salt or hydrate thereof, inert, pharmaceutically acceptable carriers can be either solid or liquid. Solid form preparations include powders, pills, tablets, dispersible granules, capsules (including time-release capsules), cachets, and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington∝s Pharmaceutical Sciences, 18th Edition, (1990), Mack Publishing Co., Easton, Pa.

Liquid form preparations of a compound of Formula (I) and/or CDK4/6 inhibitors include solutions, suspensions, elixirs, tinctures, emulsions, syrups, suspensions, and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions a compound of Formula (I) and/or CDK4/6 inhibitors can, for example, be prepared by dissolution, dispersion, etc. For example, the disclosed salt is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Also included are solid form preparations of a compound of Formula (I) and/or CDK4/6 inhibitors that are intended to be converted, shortly before use, to liquid form preparations for either oral or parenteral administration. Such liquid forms include solutions, suspensions and emulsions.

Parental injectable administration of a compound of Formula (I) and/or CDK4/6 inhibitors is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations of a compound of Formula (I) and/or CDK4/6 inhibitors suitable for inhalation may include solutions and solids in powder form, which may be in combination with a pharmaceutically acceptable carrier, such as an inert compressed gas, e.g., nitrogen.

Pharmaceutical compositions of a compound of Formula (I) and/or CDK4/6 inhibitors can be prepared according to conventional mixing, granulating or coating methods, respectively, and the present pharmaceutical compositions can contain from about 0.1% to about 99%, from about 5% to about 90%, or from about 1% to about 20% of the compound of Formula (I) and/or CDK4/6 inhibitors by weight.

All amounts of any component of an oral dosage form described herein, e.g., a tablet, that are indicated based on % w/w refer to the total weight of the oral dosage form, unless otherwise indicated.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1—Compound (I-c)—ER Degrader for Subjects with Locally Advanced or Metastatic Breast Cancer Breast cancer is the second most common cancer in women. About 268,000 women are expected to be diagnosed with invasive breast cancer in the US in 2019. (American Cancer Society.) Metastatic breast cancer accounts for ~6% of newly diagnosed cases. (Malmgren, J. A., Breast Cancer Res Treat (2018) 167:579-590.) 80% of newly diagnosed breast cancers are estrogen receptor (ER) positive. (National Cancer Institute, Hormone Therapy for Breast Cancer.)

Fulvestrant has validated the relevance of ER degradation in breast cancer.

After 6 months of fulvestrant treatment, up to 50% of ER baseline levels remain (Gutteridge et al., Breast Cancer Res Treat 2004; 88 suppl 1:S177).

Compound (I-c) is a potent degrader ($DC_{50}$=1.8 nM) of the estrogen receptor, which is in development for the treatment of patients with ER+ locally advanced or metastatic breast cancer.

Example 2—Preclinical Efficacious Exposure Range for Compound (I-c)

In preclinical animal studies, administration of Compound (I-c) was performed at doses of 3 mg/kg, 10 mg/kg, and 30 mg/kg (oral, once daily). The pharmacokinetic results are shown below in Table 1. At doses of 3 mg/kg, 10 mg/kg, and 30 mg/kg of Compound (I-c), tumor growth inhibition (TGI) of 85%, 98%, and 124%, respectively, was observed compared to a control group in a MCF7 xenograft model.

FIG. 1 shows the results of the tumor growth inhibition experiments at the tested doses (mean tumor volume ($mm^3$) vs. time).

Figure 2:
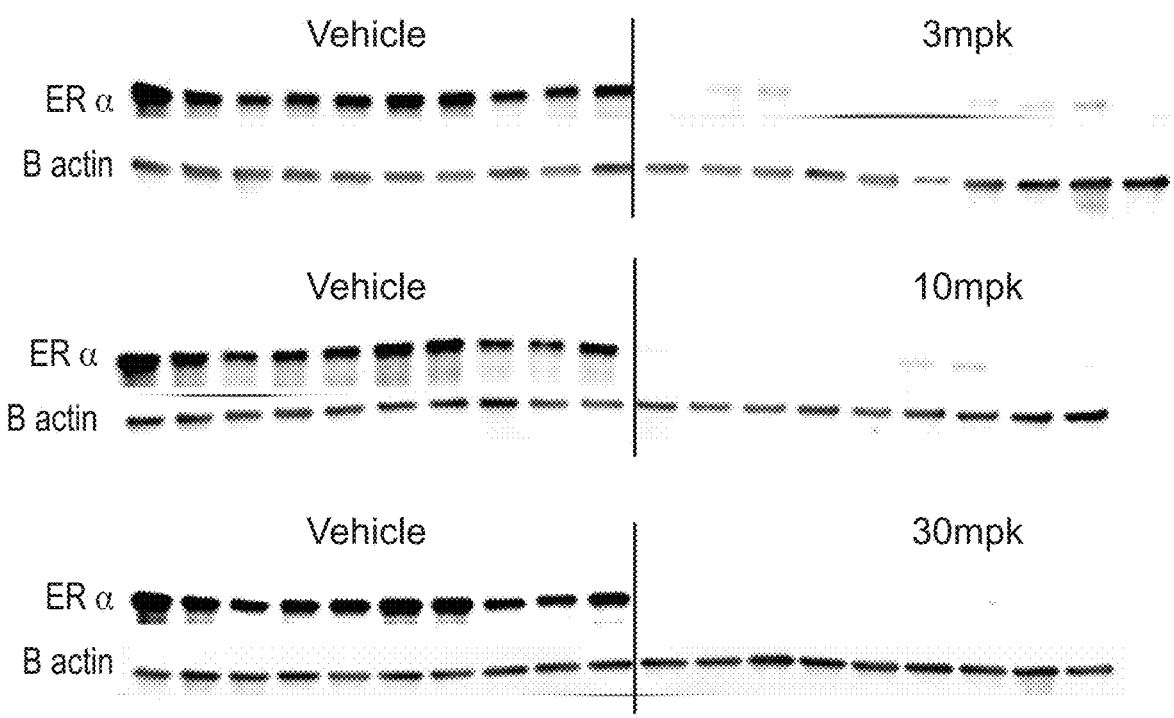
FIG. 2 is a Western Blot experiment that shows the reduction of ER in MCF7 xenograft tumors in response to dosing of Compound (I-c) of 3 mg/kg, 10 mg/kg, and 30 mg/kg (oral, once daily).

FIG. 2 shows the reduction of ER in MCF7 xenograft tumors in response to dosing of Compound (I-c) of 3 mg/kg, 10 mg/kg, and 30 mg/kg (oral, once daily).

TABLE 1

| Dose (oral, once daily) | Mean $AUC_{0-24}$ (ng*hr/mL) | Mean $C_{max}$ (ng/mL) |
|---|---|---|
| 3 mg/kg | 658 | 84 |
| 10 mg/kg | 2538 | 312 |
| 30 mg/kg[a] | 5717 | 962 |

[a]single dose

Values represent total drug concentrations

Example 3—Toxicology Studies

Animals were orally administered Compound (I-c) once daily for 28 days, followed by a 28-day recovery period for high dose-animals. In dogs, once daily, oral doses of 15 mg/kg, 45 mg/kg, or 90 mg/kg of Compound (I-c) were administered. In rats, once daily, oral doses of 3 mg/kg, 10 mg/kg, 30 mg/kg, or 100 mg/kg of Compound (I-c) were administered. These studies have shown no clinical signs of toxicity following oral, once daily doses of Compound (I-c) in doses up to 100 mg/kg/day in rats and 90 mg/kg/day in dogs. Additionally, no effects on the overall animal health or well-being of the animals were observed.

Example 4—Phase I Clinical Trial Study Design with Compound (I-c)

A Phase I Clinical Trial with Compound (I-c) was undertaken. A traditional 3+3 dose escalation design was implemented. Starting dose of Compound (I-c) was 30 mg administered orally, once daily with food. Dose increases were dependent on toxicities.

The key entry criteria for this trial were: ER+/HER2− advanced breast cancer; at least two prior endocrine therapies in any setting, and a CDK4/6 inhibitor; and up to three prior cytotoxic chemotherapy regimens.

The key objectives for this trial were obtaining the maximum tolerated dose of Compound (I-c) and the recommended Phase II trial dose. Additional objectives included assessing overall safety of Compound (I-c), pharmacokinetics, anti-tumor activity (for example, RECIST, CBR), and biomarkers, including, for example, ER gene (ESR1) mutational status in ctDNA and/or tumor tissue; and ER, Progesterone Receptor, and Ki-67 levels in pre- and post-treatment tumor biopsies in patients with accessible tumor tissue.

Example 5—Phase I Pharmacokinetic Data—Oral Administration of Compound (I-c)

In a Phase I clinical trial, Compound (I-c) was administered orally at a dose of 30 mg/day. It was observed that treatment with 30 mg/day of Compound (I-c) enters the preclinical efficacious range associated with tumor growth inhibition.

Figure 3:
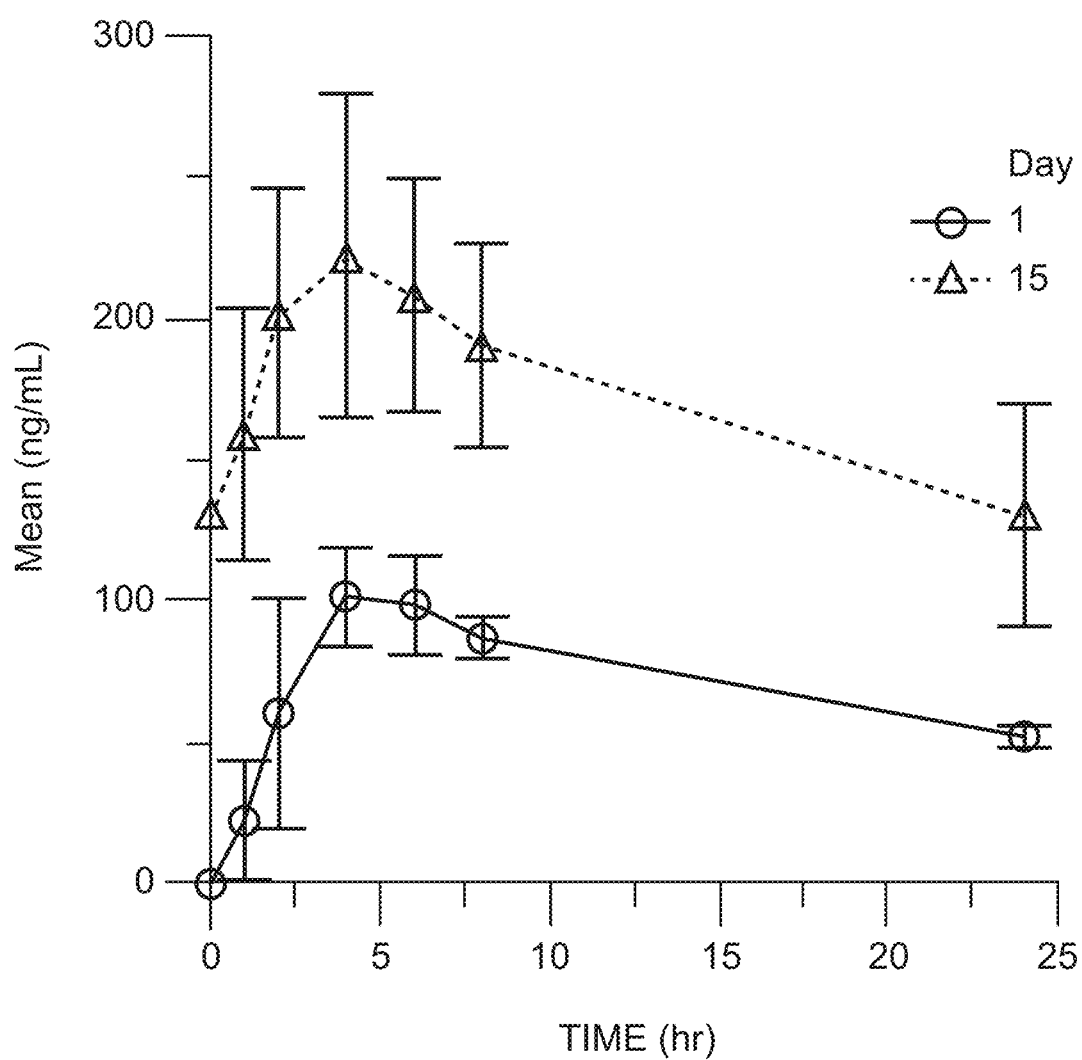
FIG. 3 is a pair of line graphs which show the mean concentration of the compound of Formula (I-c) (ng/mL) over the course of 24 hours post-dosing on both day 1 and day 15 in a Phase I clinical trial.
Figure 4:
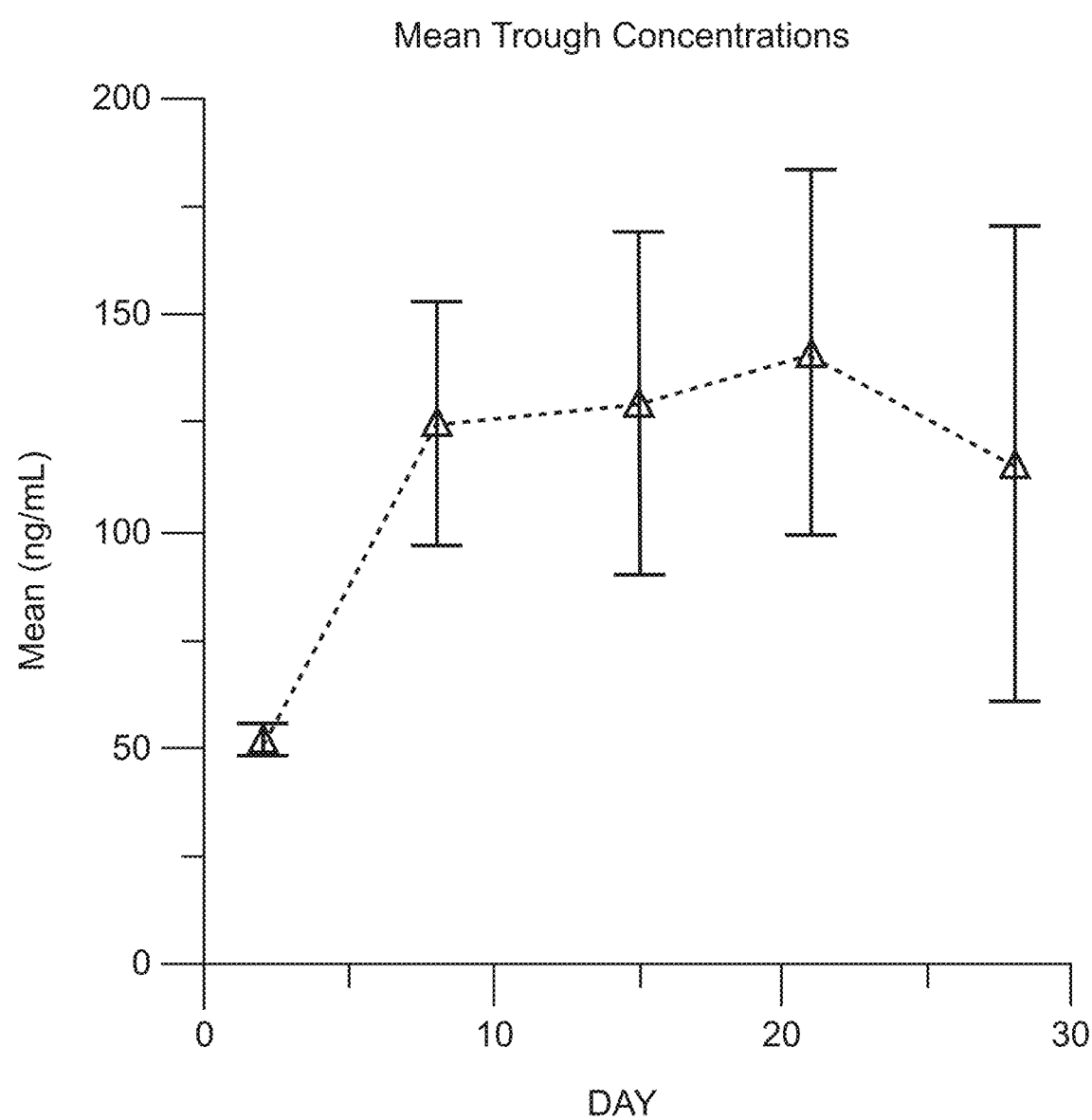
FIG. 4 is a line graph that provides a representation of mean trough concentrations of Compound (I-c) (ng/mL) throughout the course of a Phase I clinical trial.

The initial pharmacokinetic results are shown below in Table 2, as well as in FIG. 3 and FIG. 4. FIG. 3 provides a representation of the concentration of Compound (I-c) over the course of 24 hours post-dosing on both day 1 and day 15. FIG. 4 provides a representation of mean trough concentrations of Compound (I-c) throughout the course of the clinical trial.

TABLE 2

| Dose | Mean Day 1 $AUC_{TAU}$ (ng*hr/mL) | Mean Day 1 $C_{max}$ (ng/mL) | Mean Day 15 $AUC_{TAU}$ (ng*hr/mL)[a] | Mean Day 15 $C_{max}$ (ng/mL) |
|---|---|---|---|---|
| 30 mg | 1690 | 109 | 4100 | 224 |

[a]Day 15 AUCs calculated using imputed 24 hour values

Example 6—Phase I Dose Escalation Studies with Compound (I-c)

Compound (I-c) was administered orally to subjects at 30 mg/day or 60 mg/day. (n=3 for both dose groups.) In the 30 mg/day cohort, no dose limiting toxicity was observed. Also, no treatment related adverse events were observed in the 30 mg/day cohort group.

Example 7—Evaluation of Anti-Tumor and Estrogen Receptor Alpha Degradation Activity of Compound (I-c) in ER-positive Orthotopic Xenograft Model MCF7

Part 1: In Vivo ERα Degradation

Figure 5:
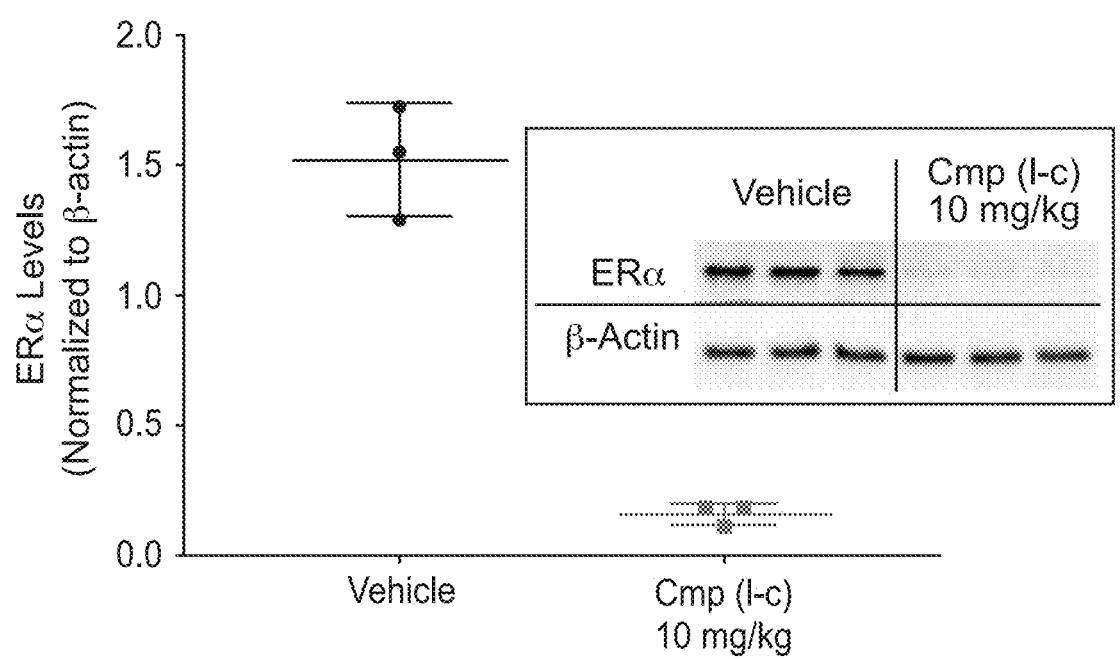
FIG. 5 is a graph and a Western Blot experiment that shows the ERa degradation activity of Compound (I-c) after 3 daily oral administrations at 10 mg/kg.

Acute estrogen receptor alpha (ERa) degradation activity of Compound (I-c) was evaluated in the MCF7 orthotopic xenograft model after 3 daily oral administrations of Compound (I-c). To assess Compound (I-c)-induced degradation of ERα in vivo, Compound (I-c) was administered at 10 mg/kg via oral gavage to MCF7-tumor bearing NOD/SCID mice, and changes in ERα levels were evaluated after 3 daily oral doses. As shown in FIG. 5, Compound (I-c) reduced tumor ERα levels by up to 95% when compared to ERα levels in tumors in vehicle-treated mice.

MCF7 tumor-bearing NOD/SCID mice were administered vehicle or Compound (I-c) (10 mg/kg, p.o.) once daily for three consecutive days. Approximately 18 hours after the final administration, mice were sacrificed, and MCF7 xenografts were harvested and lysed to determine ER levels by immunoblotting. Compound (I-c) reduced ER levels by up to 95% compared to vehicle (as represented by the 3 samples from each group in FIG. 5). β-actin served as the loading control for the immunoblots. Diet was supplemented with peanut butter to help maintain body weights.

Details of Animal Studies:

Species: NOD/SCID female mice (Charles River, 6-7 weeks old upon arrival).

Animal handling: Axial mammary fat pad implantation of $5 \times 10^6$ MCF7 cells/200 per mouse (17β-estradiol 0.36 mg 90-day pellet implanted day before).

Dosing: Oral (gavage), once a day (QD) for 3 days (QDx3). Vehicle: 2% Tween80/PEG400 ('PEG/Tween').

TABLE 3

Study arms.

| Group | Compound | mg/kg | Route/Days dosed | Vehicle | Dose Volume | # of Animals |
|---|---|---|---|---|---|---|
| 1 | Vehicle | 0 | Oral/QDx3 | PEG/Tween | 5 mL/kg | 6 |
| 2 | Compound (I-c) | 10 | Oral/QDx3 | PEG/Tween | 5 mL/kg | 6 |

Sampling: Terminal sacrifice was ~18 hrs after last dose; tumors were harvested, divided and flash frozen. ERα levels were determined by immunoblotting.

Detailed procedure for ERα degradation Assay:

Cell Lysis: flash frozen tumors were removed from −80° C. storage and placed on dry ice. RIPA lysis buffer and Halt protease inhibitors were used at 400 μl per tumor sample. A steel ball (5 mm) was placed in each sample for tissue disruption. Samples were lysed with TissueLyzer at 24 Hz for 4 minutes. The homogenization was stopped half way through the process and the block flipped over for the duration of the process. Steel beads were pulled out of the tubes and the lysates were spun down at 21,000×g for 15 minutes at 4° C. Lysates were then measured for total protein concentration by BCA (per manufacturer's protocol).

Detection of proteins by immunoblot: lysates were mixed with sample buffer and reducing agent (per manufacturer's protocol). Samples were denatured at 95° C. for 5 minutes in thermal cycler. Samples were cooled and spun down (5000×g; 1 minute) prior to loading on gel. Gels were loaded with 10 μg total protein per lane. Samples were loaded on 4-15% Criterion Tris/Glycine gels and run for 25 minutes at 250 constant volts in 1× Tris/Glycine/SDS buffer. Protein was transferred from gels to nitrocellulose with Bio-Rad Turbo on default setting. All blots were rinsed with distilled water and blocked for 1 hour at RT in 5% BSA in TBS-T (TBS with 0.1% Tween) on rocker. The blots were cut so that beta-actin and ERα can be detected from the same lane/sample.

Blots were incubated with primary antibody in 5% BSA in TBST (0.1%) overnight at 4° C. on rocker:

ERα from Bethyl labs (1:2000);

Beta-actin from CST (1:3000).

Blot was washed with TBST (0.1%) three times for 5 minutes on rocker at RT. Secondary antibody was added, and blots incubated at RT on rocker for 1 hour (1:18,000 anti-rabbit-HRP in TBS-T). Blots were washed 3 times in TBST (0.1%) for 5 minutes at RT on the rocker. Signal was developed with Pierce WestFemto maximum sensitivity substrate for 5 minutes and blots imaged on BioRad ChemiDoc.

Part 2: Anti-Tumor Effects in MCF7 Xenograft Model.

The anti-tumor activity and prolonged ERα degradation activity of Compound (I-c) was evaluated in a MCF7 orthotopic xenograft model.

Figure 6:
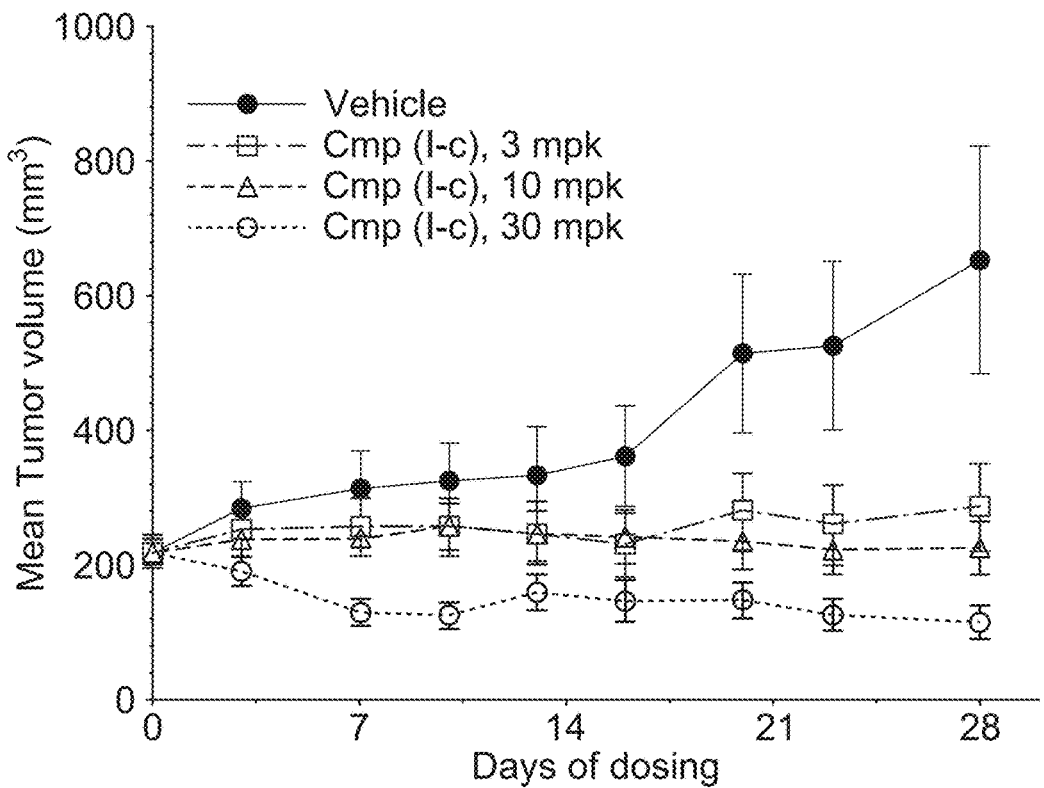
FIG. 6 shows the results of tumor growth inhibition experiments (mean tumor volume (mm$^3$) vs. time) associated with oral, once daily administration of Compound (I-c) for 28 days at doses of 3 mg/kg, 10 mg/kg, and 30 mg/kg compared to vehicle. At doses of 3 mg/kg, 10 mg/kg, and 30 mg/kg of Compound (I-c), tumor growth inhibition (TGI) of 85%, 98%, and 124%, respectively, was observed compared to a control group in a MCF7 xenograft model.

In this MCF7-xenograft model, Compound (I-c) displayed dose-dependent efficacy (FIG. 6) with doses of 3 and 10 mg/kg/day showing tumor growth inhibition (TGI) of 85% and 98%, respectively, relative to vehicle, and 30 mg/kg/day leading to tumor shrinkage (124% TGI) (Table 4).

In the experiments, dose-dependent inhibition of tumor growth by Compound (I-c) in an orthotopic MCF7 mouse xenograft model. Female NOD/SCID mice were implanted with MCF7 cells in the mammary fat pad, and Compound (I-c) administration (QDx28; p.o.) was initiated once the tumors reached 200 mm³. Tumor volumes were evaluated twice per week for twenty-eight days. Compound (I-c) at 3, 10, or 30 mg/kg inhibited growth of estradiol-stimulated MCF7 xenografts (85%, 98%, and 124% TGI, respectively).

TABLE 4

Tumor Growth Inhibition (TGI)

| | Vehicle (n = 10) | Compound (I-c), 3 mg/kg (n = 10) | Compound (I-c), 10 mg/kg (n = 9) | Compound (I-c), 30 mg/kg (n = 10) |
|---|---|---|---|---|
| Day 0 Tumor volume *(mm³) | 218 ± 69 | 217 ± 67 | 218 ± 65 | 217 ± 66 |
| Day 28 Tumor volume* (mm³) | 656 ± 536 | 286 ± 206 | 226 ± 118 | 115 ± 79 |
| TGI (% vehicle) | n/a | 85 | 98 | 124 |

*Tumor volumes are mean ± SD.

Sampling: Tumors were measured twice weekly. Terminal sacrifice was ~18 hr after last dose; tumors were harvested, divided, and flash frozen. ERα levels were determined by immunoblotting.

Tumor volume calculation: Tumor Volume=(width× width×length)/2, where all measurements are in mm and the tumor volume is in mm³.

Tumor Growth Inhibition (TGI) calculation: TGI (%)

$$TGI\ (\%) = \left[1 - \frac{(\text{Tumor volume, compound, Day } X) - (\text{Tumor volume, compound, Day } O)}{(\text{Tumor volume, vehicle, Day } X) - (\text{Tumor volume, vehicle, Day } O)}\right] \times 100 \text{ where}$$

tumor volume is in $mm^3$.

Figure 7:
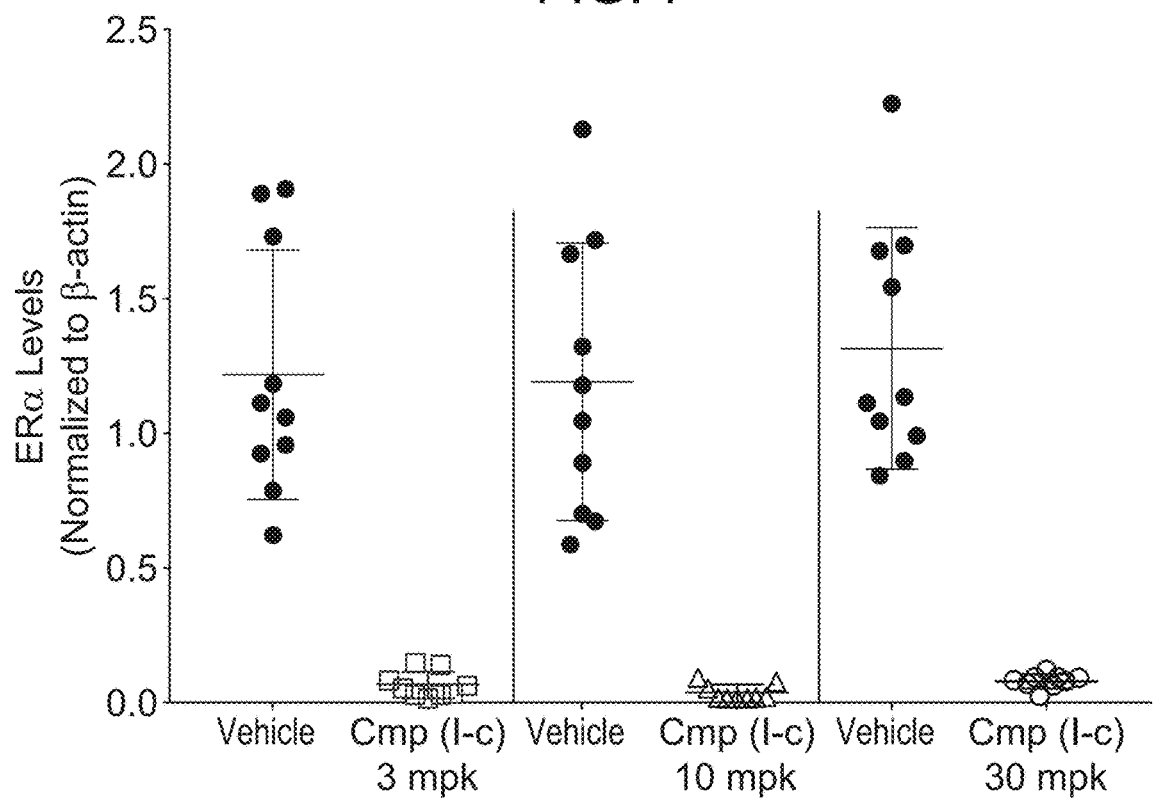
FIG. 7 are graphs that show that daily oral doses of 3 mg/kg, 10 mg/kg, and 30 mg/kg of Compound (I-c) for 28 days reduce ERa levels by >94% compared to mice administered vehicle only.

At study termination, the tumors were removed from the mice, and ERα levels were determined by immunoblotting the tumor homogenates. As seen in FIG. 7, all doses of Compound (I-c) significantly reduced ERα levels (by >94%) when compared to mice administered vehicle only. Taken together, these data demonstrate that Compound (I-c) displays potent anti-tumor activity against a well-established in vivo ER-positive breast cancer model, concurrent with robust degradation of ERα in the tumors.

TABLE 5

Study Arms:

| Group | Compound | mg/kg | Route/Days dosed | Vehicle | Dose Volume | # animals |
|---|---|---|---|---|---|---|
| 1 | Vehicle | 0 | Oral/QDx28 | PEG/Tween | 5 mL/kg | 10 |
| 2 | Compound (I-c) | 3 | Oral/QDx28 | PEG/Tween | 5 mL/kg | 10 |
| 3 | Compound (I-c) | 10 | Oral/QDx28 | PEG/Tween | 5 mL/kg | 10 |
| 4 | Compound (I-c) | 30 | Oral/QDx28 | PEG/Tween | 5 mL/kg | 10 |

Part 2: Anti-Tumor Effects in Combination with CDK4/6 Inhibitor

To evaluate anti-tumor activity of Compound (I-c) in the MCF7 orthotopic xenograft model in combination with a CDK4/6 inhibitor, the effects of combining Compound (I-c) with a CDK4/6 inhibitor were assessed in MCF7-tumor bearing mice.

NOD/SCID female mice (Charles River, 6-7 weeks old upon arrival) received implantation of $5 \times 10^6$ MCF7 cells/200 μL per mouse in axial mammary fat pad (17β-estradiol 0.36 mg 90-day pellet implanted day before). Compound administration was initiated once the tumors reached 200 $mm^3$. Diet was supplemented with peanut butter to help maintain body weights.

Figure 8:
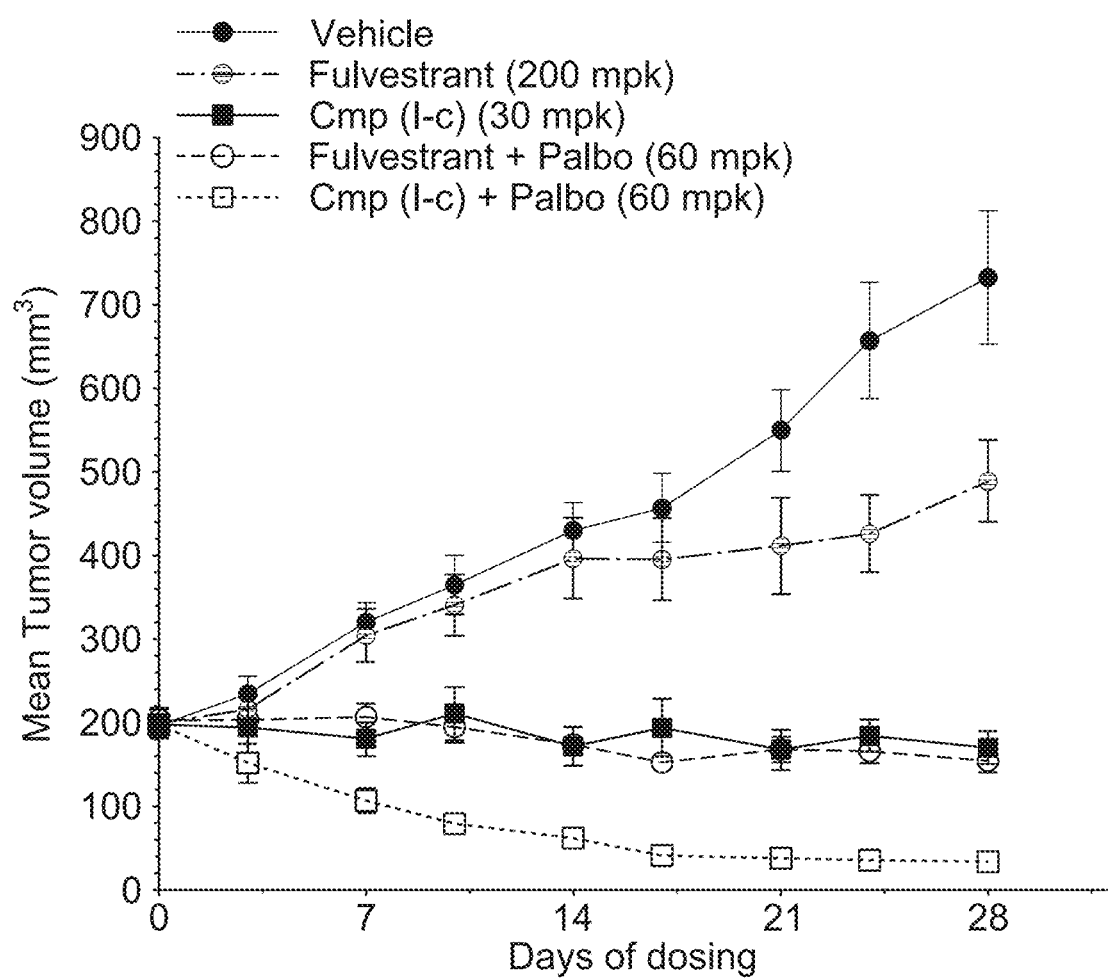
FIG. 8 shows the results of tumor growth inhibition experiments (mean tumor volume (mm$^3$) vs. time) associated with oral, once daily administration of Compound (I-c) at a dose of 30 mg/kg for 28 days, Compound (I-c) (30 mg/kg, oral, once daily for 28 days) plus palbociclib (oral, once daily administration at 60 mg/kg for 28 days), fulvestrant (200 mg/kg, subcutaneous twice/week for 2 weeks), and fulvestrant (200 mg/kg, subcutaneous twice/week for 2 weeks) plus palbociclib (oral, once daily administration at 60 mg/kg for 28 days compared to vehicle. When compared to single-agent Compound (I-c) activity in this model (105% TGI), combination of Compound (I-c) and palbociclib provided significant tumor regressions (131% TGI). In contrast, single-agent fulvestrant, which was dosed subcutaneously, resulted in only modest tumor growth inhibition (46% TGI), while the combination of fulvestrant and palbociclib resulted in improved inhibition of tumor growth (108% TGI), but not to the levels of that achieved with Compound (I-c) and palbociclib.

Compound (I-c) (30 mg/kg/day) and the CDK4/6 inhibitor palbociclib (60 mg/kg/day) were administered for twenty-eight days. When compared to single-agent Compound (I-c) activity (105% TGI) in this model, combination of Compound (I-c) and palbociclib provided significant tumor regressions (131% TGI). In contrast, single-agent fulvestrant, which was dosed subcutaneously, resulted in only modest tumor growth inhibition (46% TGI), while the combination of fulvestrant and palbociclib resulted in improved inhibition of tumor growth (108% TGI) but not to the levels of that achieved with Compound (I-c) and palbociclib. (FIG. 8 and Table 6.)

TABLE 6

Tumor Growth Inhibition (TGI) Studies.

| | Vehicle (n = 15) | Fulvestrant, 200 mg/kg (n = 10) | Compound (I-c), 30 mg/kg (n = 10) | Fulvestrant, 200 mg/kg + Palbociclib, 60 mg/kg (n = 10) | Compound (I-c), 30 mg/kg + Palbociclib, 60 mg/kg (n = 10) |
|---|---|---|---|---|---|
| Day 0 Tumor Volume* ($mm^3$) | 197 ± 56 | 199 ± 50 | 199 ± 55 | 204 ± 42 | 198 ± 49 |
| Day 28 Tumor Volume* ($mm^3$) | 733 ± 309 | 489 ± 154 | 170 ± 62 | 154 ± 42 | 33 ± 16 |
| TGI (% vehicle) | | 46 | 105 | 108 | 131 |

*Tumor volumes are mean ± SD.

Dosing:

Compound (I-c) and palbociclib: Oral (gavage), once a day for 28 days (QDx28)

Palbociclib is dosed 30-60 minutes prior to dosing with Compound (I-c). Without wishing to be bound by theory, this is to prevent palbociclib and Compound (I-c), and their respective excipients, from mixing in the acidic compartment of the stomach.

Fulvestrant: Subcutaneous (SC), twice a week (BIW) for 2 weeks (BIW×2), followed by once a week (QW) for 2 weeks (QW×2)

Vehicles:

For Compound (I-c): 2% Tween 80/PEG-400 ('PEG/Tween'). The ratio of Tween 80 to PEG-400 is 0.02 g Tween 80 to 1 ml PEG-400. PEG-400 is added to a pre-aliquoted volume of Tween 80.

For fulvestrant: 10% w/v Ethanol, 10% w/v Benzyl Alcohol, and 15% w/v Benzyl Benzoate as co-solvents and made up to 100% w/v with Castor Oil ('EBB/Castor Oil')

For palbociclib: 50 mM sodium lactate, pH 4.0 ('Sodium lactate')

TABLE 7

Study arms.

| Group | Compound(s) | mg/kg | Route/Days dosed | Vehicle | Dose Volume | # Animals |
|---|---|---|---|---|---|---|
| 1 | Vehicle | 0 | Oral/QDx28 | PEG/Tween | 5 mL/kg | 15 |
| 2 | Fulvestrant | 200 | SC/BIWx2, QWx2 | EBB/Castor Oil | 4 mL/kg | 10 |
| 3 | Compound (I-c) | 30 | Oral/QDx28 | PEG/Tween | 5 mL/kg | 10 |
| 4 | Fulvestrant + Palbociclib | 200/60 | SC/BIWx2, QWx2; Oral/QDx28 | EBB/Castor Oil; Sodium lactate | 4 mL/kg; 5 mL/kg | 10 |
| 5 | Compound (I-c) + Palbociclib | 30/60 | Oral/QDx28 | PEG/Tween Sodium lactate | 5 mL/kg | 10 |

Sampling: tumors were measured twice weekly. Terminal sacrifice was ~18 hr after last dose; tumors were harvested, divided, and flash frozen. ERα levels were determined by immunoblotting.

Figure 9:
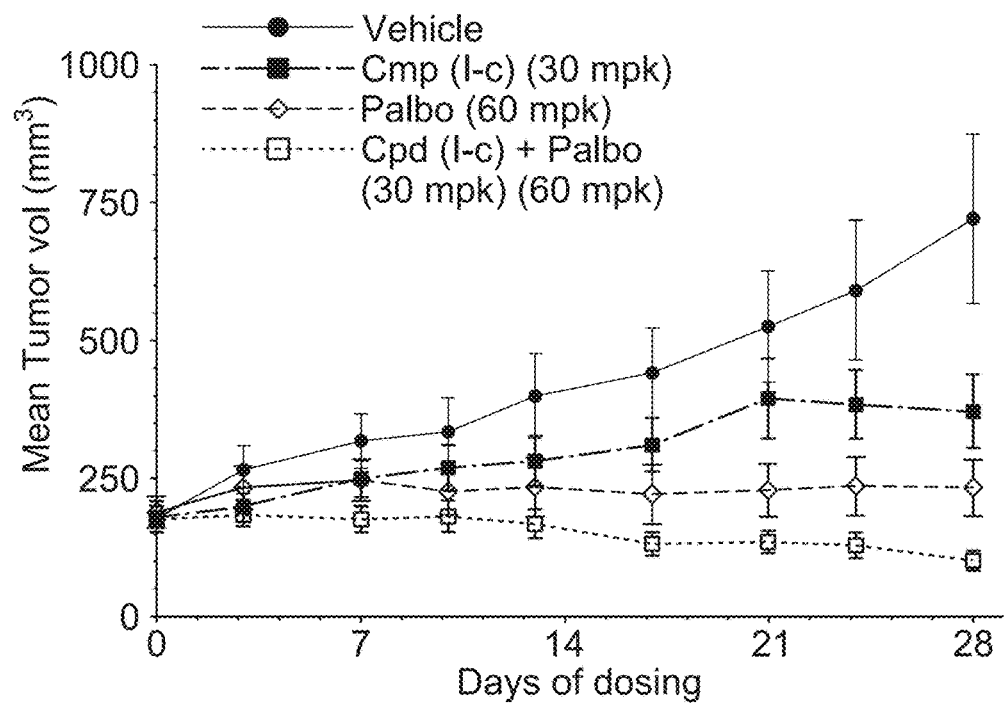
FIG. 9 shows the results of tamoxifen-resistant MCF7 xenograft growth inhibition experiments (mean tumor volume (mm$^3$) vs. time) associated with oral, once daily administration of Compound (I-c) at a dose of 30 mg/kg for 28 days compared to palbociclib (60 mg/kg, oral, once daily for 28 days), Compound (I-c) (30 mg/kg, oral, once daily for 28 days) plus palbociclib (60 mg/kg, oral, once daily for 28 days), and vehicle. When Compound (I-c) was combined with 60 mg/kg/day palbociclib, the combination regimen caused greater tumor growth inhibition (113% TGI) when compared to the single-agent arm of palbociclib (91% TGI).

Example 8—Evaluation of Anti-Tumor and Estrogen Receptor Alpha Degradation Activity of Compound (I-c) in ER-positive Orthotopic Xenograft Model of Tamoxifen-Resistant MCF7 Cells The anti-tumor activity of Compound (I-c) in a tamoxifen-resistant estrogen receptor positive (ER+) breast cancer orthotopic xenograft model was evaluated as a single agent and in combination with a CDK4/6-inhibitor. Additionally, the ERα degradation activity of Compound (I-c) was evaluated in a tamoxifen-resistant ER+ breast cancer orthotopic xenograft model Data Summary In FIG. 9 and Table 8, growth of tamoxifen-resistant MCF7 xenografts was inhibited by 65% after once daily oral administration of 30 mg/kg/day Compound (I-c) for 28 days. When Compound (I-c) was combined with 60 mg/kg/day palbociclib, the combination regimen caused greater tumor growth inhibition (113% TGI) when compared to the single-agent arm of palbociclib (91% TGI).

Figure 10:
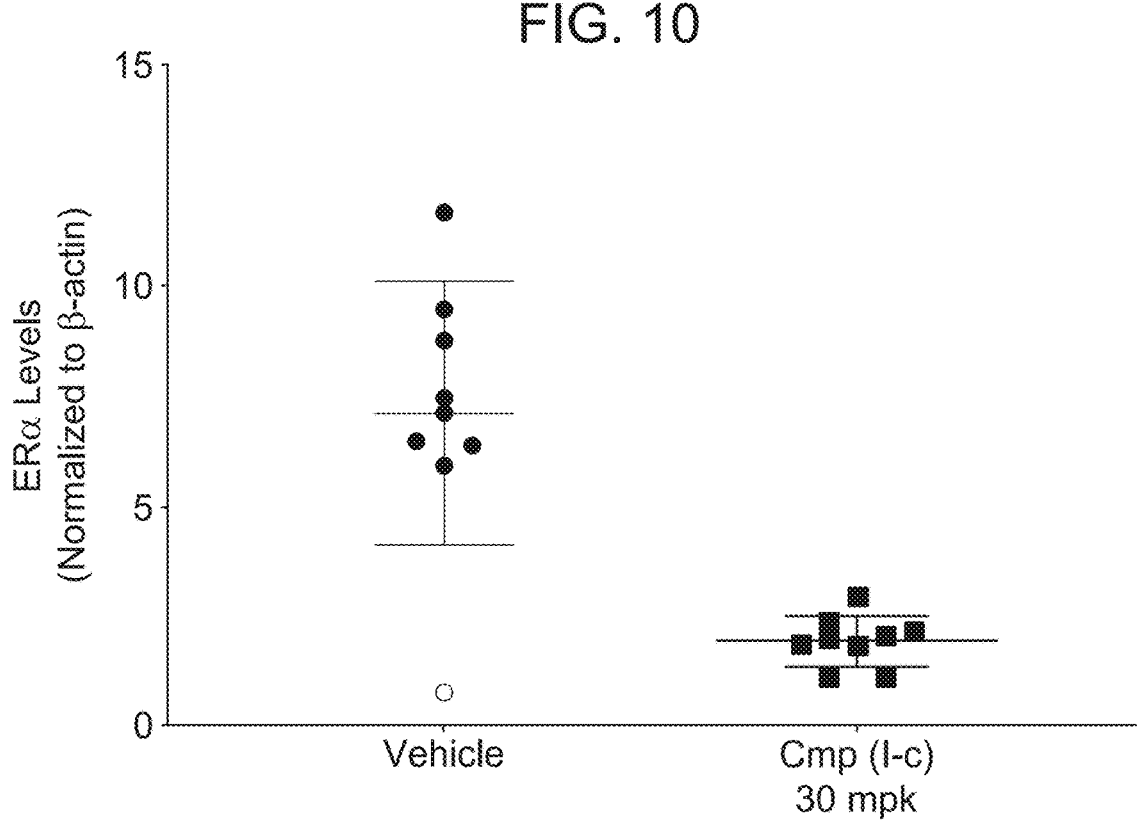
FIG. 10, FIG. 11, and FIG. 12 are graphs that show the effects of doses of Compound (I-c) (30 mg/kg, oral, once daily for 28 days, FIG. 10), palbociclib (60 mg/kg, oral, once daily for 28 days, FIG. 12), and Compound (I-c) (30 mg/kg, oral, once daily for 28 days) plus palbociclib (60 mg/kg, oral, once daily for 28 days) (FIG. 11) on in vivo ERa levels in tamoxifen-resistant MCF7 xenografts experiments.
Figure 11:
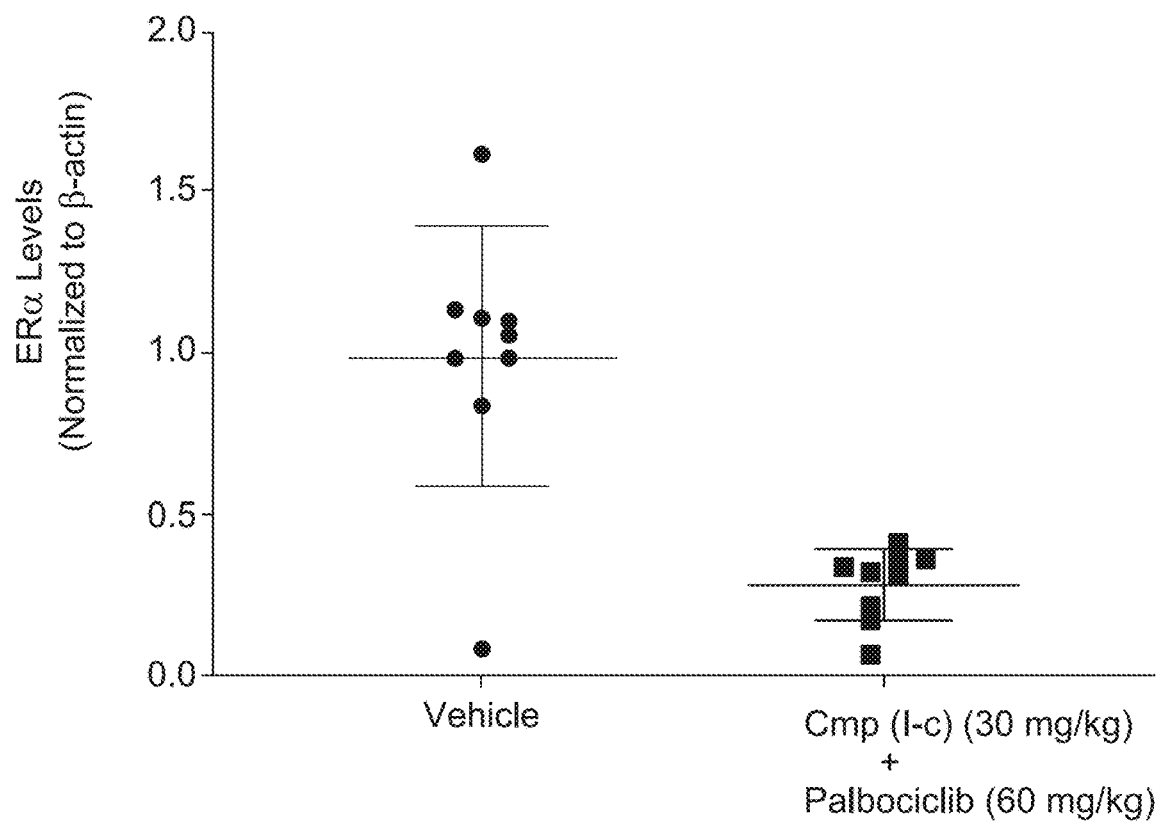
Figure 12:
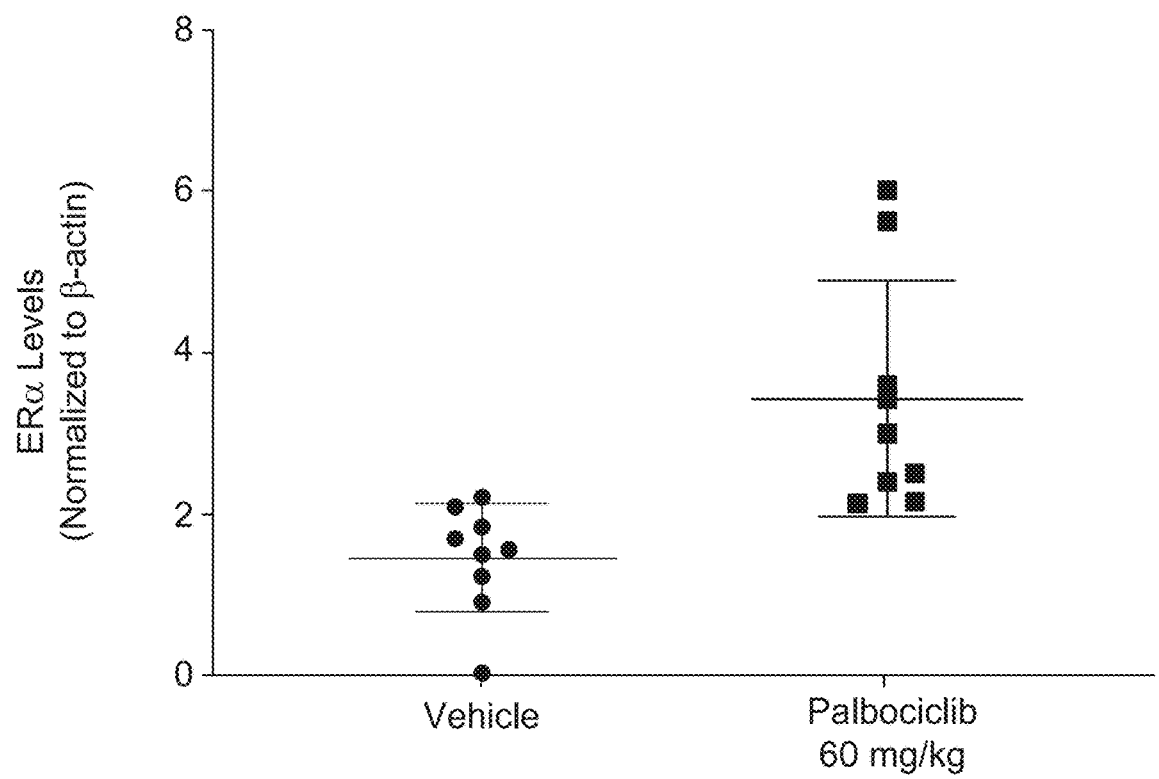

At study termination, the tumors were removed from the mice, and ERα levels were determined by immunoblotting the tumor homogenates. As seen in FIG. 10, compared to vehicle, 30 mg/kg Compound (I-c) reduced ERα levels by 73%, and the combination with 60 mg/kg palbociclib similarly reduced ERα levels by 72% (FIG. 11). Palbociclib alone (60 mg/kg), however, did not reduce ERα levels (FIG. 12). ERα levels from the various compound arms were compared to vehicle-treated animals by analyzing the tumor lysates on separate immunoblots (graphs in FIG. 10, FIG. 11, and FIG. 12 depict data from individual immunoblots) and the average ERα levels with standard deviation is shown.

TABLE 8

Tumor Growth Inhibition (TGI)

| | Vehicle (n = 9) | Compound (I-c), 30 mg/kg (n = 9) | Palbociclib, 60 mg/kg (n = 9) | Compound (I-c), (30 mg/kg) and Palbociclib (60 mg/kg) |
|---|---|---|---|---|
| Day 0 Tumor volume* (mm³) | 179 ± 69 | 178 ± 76 | 180 ± 80 | 176 ± 70 |
| Day 28 Tumor volume* (mm³) | 721 ± 459 | 361 ± 181 | 222 ± 139 | 102 ± 53 |
| TGI (% vehicle) | n/a | 65 | 91 | 113 |

*Tumor volumes are mean ± SD.

Details of Animal Studies:

Species: Ovariectomized Nu/Nu female mice. Animal handling: Axial mammary fat pad implantation of tamoxifen-resistant tumor fragment (from E45 passage. SC per mouse. Tamoxifen pellet (5 mg, 60-day release) was implanted under the same anesthesia as tumor fragment (pellet—dorsal; tumor—ventral).

Dosing: Oral (gavage), once a day for 28 days (QDx28)

Vehicles: for Compound (I-c): 2% Tween80/PEG400 ('PEG/Tween'); for palbociclib: 50 mM sodium lactate, pH 4 ('Sodium lactate')

TABLE 9

Study arms.

| Groups | Compound | Dose (mg/kg) | Route, Days dosed | Vehicle | Dosing Volume | # animals |
|---|---|---|---|---|---|---|
| 1 | Vehicle | 0 | Oral, QDx28 | PEG/Tween | 5 mL/kg | 9 |
| 2 | Compound (I-c) | 30 | Oral, QDx28 | PEG/Tween | 5 mL/kg | 9 |
| 3 | Palbociclib | 60 | Oral, QDx28 | Sodium lactate | 5 mL/kg | 9 |
| 4 | Compound (I-c)/ Palbociclib | 30/60 | Oral, QDx28 | PEG/Tween/ Sodium lactate | 5 mL/kg | 9 |

Sampling: Tumors were measured twice weekly. Terminal sacrifice was ~18 hr after last dose; tumors were harvested, divided, and flash frozen. ERα levels were determined by immunoblotting (see Appendix 1 for details).

Detailed Procedure for ERα Degradation Assay:

Cell Lysis

Flash frozen tumors were removed from −80° C. storage and placed on dry ice. RIPA lysis buffer and Halt protease inhibitors were used at 400 µl per tumor sample. A steel ball (5 mm) was placed in each sample for tissue disruption. Samples were lysed with TissueLyzer at 24 Hz for 4 minutes. The homogenization was stopped half way through the process and the block flipped over for the duration of the process. Steel beads were pulled out of the tubes and the lysates were spun down at 21,000×g for 15 minutes at 4° C. Lysates were then measured for total protein concentration by BCA (per manufacturer's protocol).

Detection of Proteins by Immunoblot.

Lysates were mixed with sample buffer and reducing agent (per manufacturer's protocol). Samples were denatured at 95° C. for 5 minutes in thermal cycler. Samples were cooled and spun down (5000×g; 1 minute) prior to loading on gel. Gels were loaded with 10 µg total protein per lane. Samples were loaded on 4-15% Criterion Tris/Glycine gels and run for 25 minutes at 250 constant volts in 1× Tris/Glycine/SDS buffer.

Protein was transferred from gels to nitrocellulose with Bio-Rad Turbo on default setting. All blots were rinsed with distilled water and blocked for 1 hour at RT in 5% BSA in TBS-T (TBS with 0.1% Tween) on rocker. The blots were cut so that beta-actin and ERα can be detected from the same lane/sample. Blots were incubated with primary antibody in 5% BSA in TBST (0.1%) overnight at 4° C. on rocker.

ERα from Bethyl labs (1:2000)

Beta-actin from CST (1:3000)

Blot was washed with TBST (0.1%) three times for 5 minutes on rocker at RT. Secondary antibody was added, and blots incubated at RT on rocker for 1 hour (1:18,000 anti-rabbit-HRP in TBS-T). Blots were washed 3 times in TBST (0.1%) for 5 minutes at RT on the rocker. Signal was developed with Pierce WestFemto maximum sensitivity substrate for 5 minutes and blots imaged on BioRad Chemi-Doc.

Example 9—Summary of In Vivo Data for Compound (I-c)

The compounds of Formula (I) disclosed herein, including Compound (I-c), are hetero-bifunctional molecules that facilitate the interactions between ER alpha and an intracellular E3 ligase complex, leading to the ubiquitination and subsequent degradation of estrogen receptors via the proteasome. Orally-bioavailable Compound (I-c) demonstrates single-digit nanomolar ERα degradation potency in wild-type and variant ERα expressing cell lines.

Figure 13:
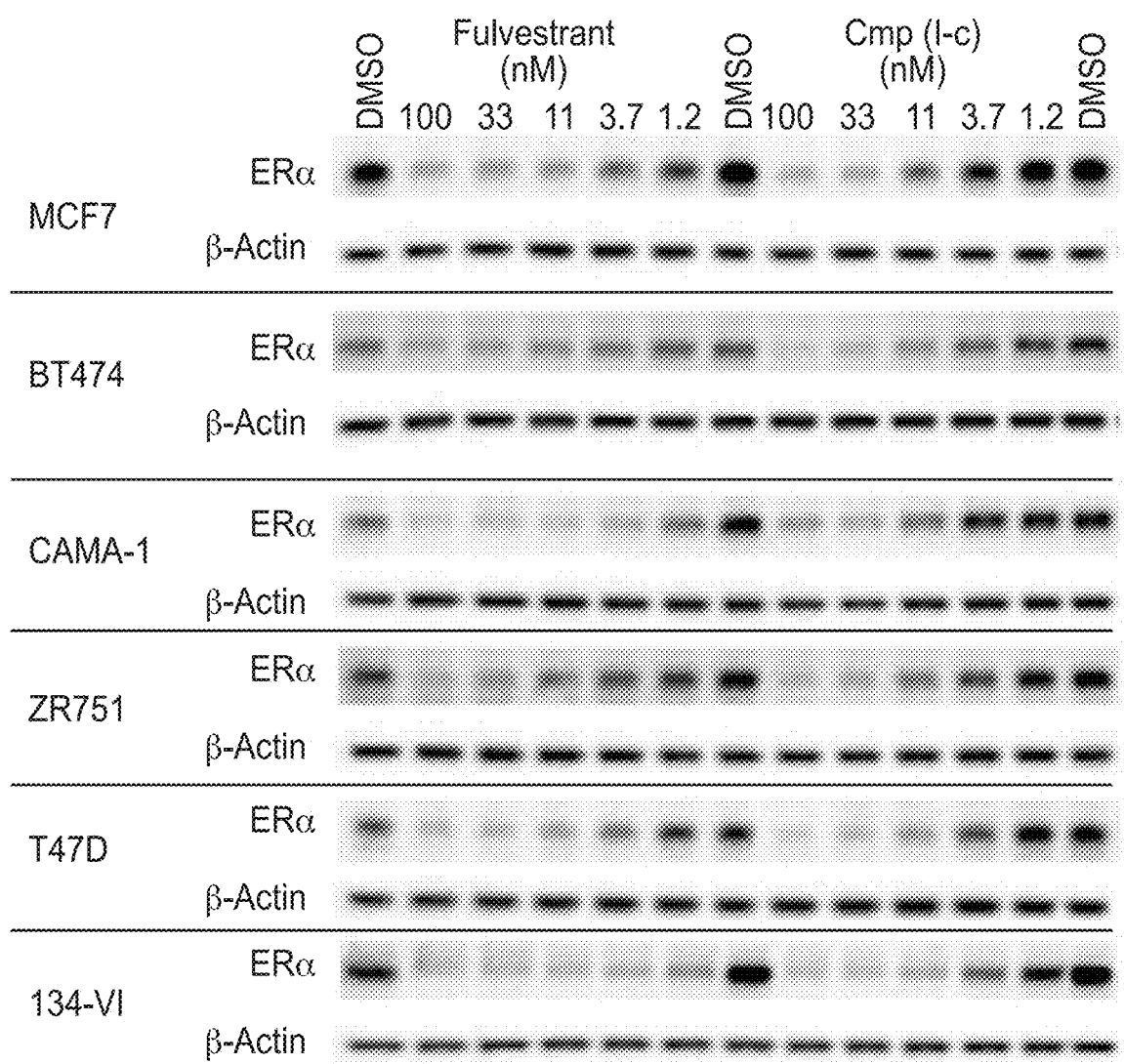
FIG. 13 provides the results of several Western Blot experiments that compares the in vitro ERα degradation activity of fulvestrant and Compound (I-c) at various concentrations in several ER-positive breast cancer cell lines.
Figure 14:
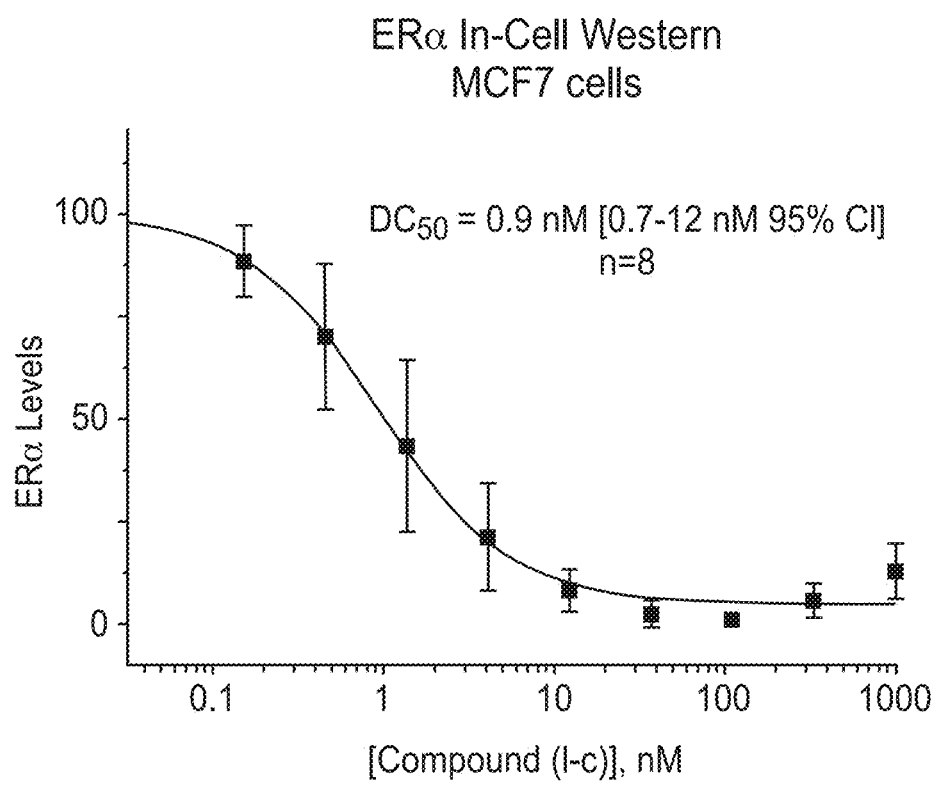
FIG. 14 is a graph that shows that the half-maximal degradation concentration ($DC_{50}$) of Compound (I-c) is 0.9 nM in MCF7 cells.
Figure 15:
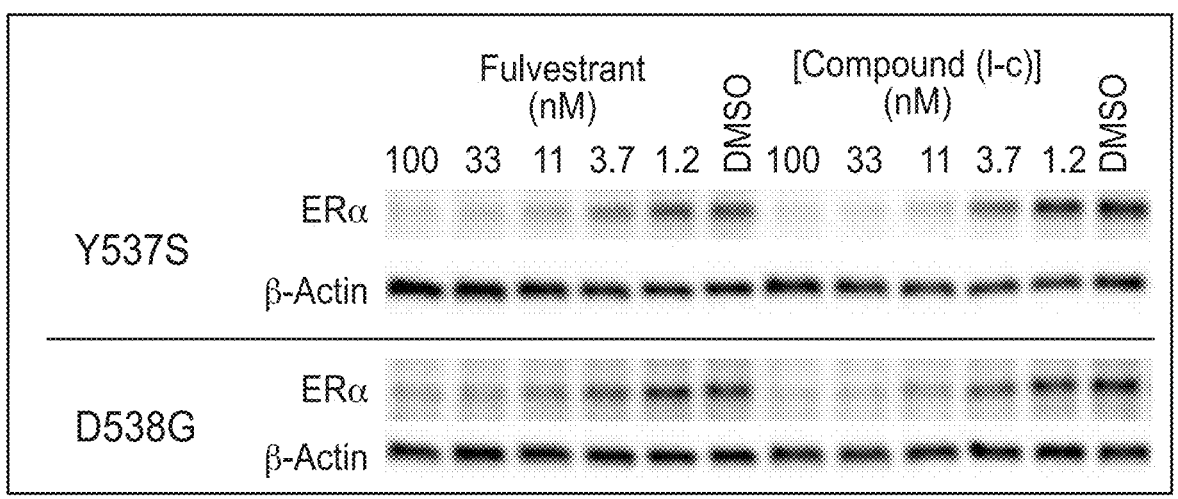
FIG. 15 provides the results of several Western Blot experiments that compare the in vitro ERα degradation activity of fulvestrant and Compound (I-c) at various concentrations in clinically-relevant ESR1 cell line variants Y537S and D538G.
Figure 16:
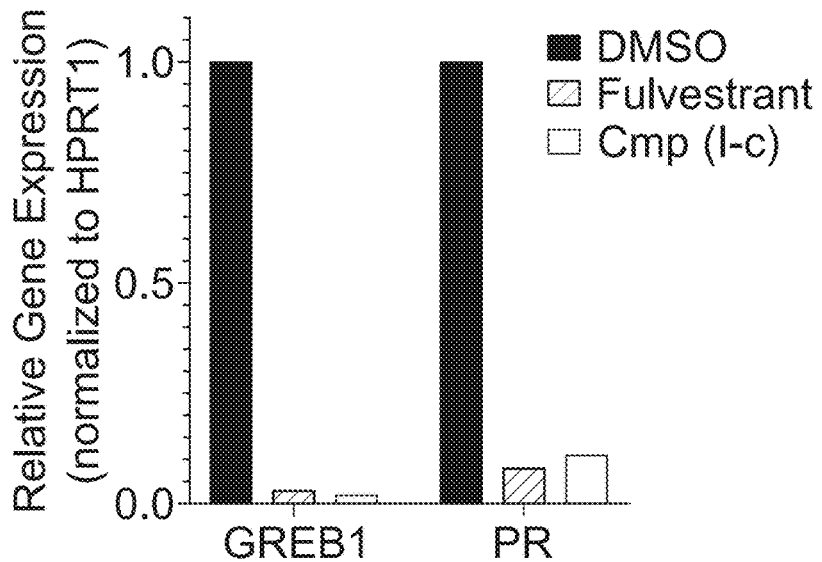
FIG. 16 is a graph showing the relative expression of GREB1 and PR in experiments with fulvestrant and Compound (I-c) compared to vehicle (DMSO).
Figure 17:
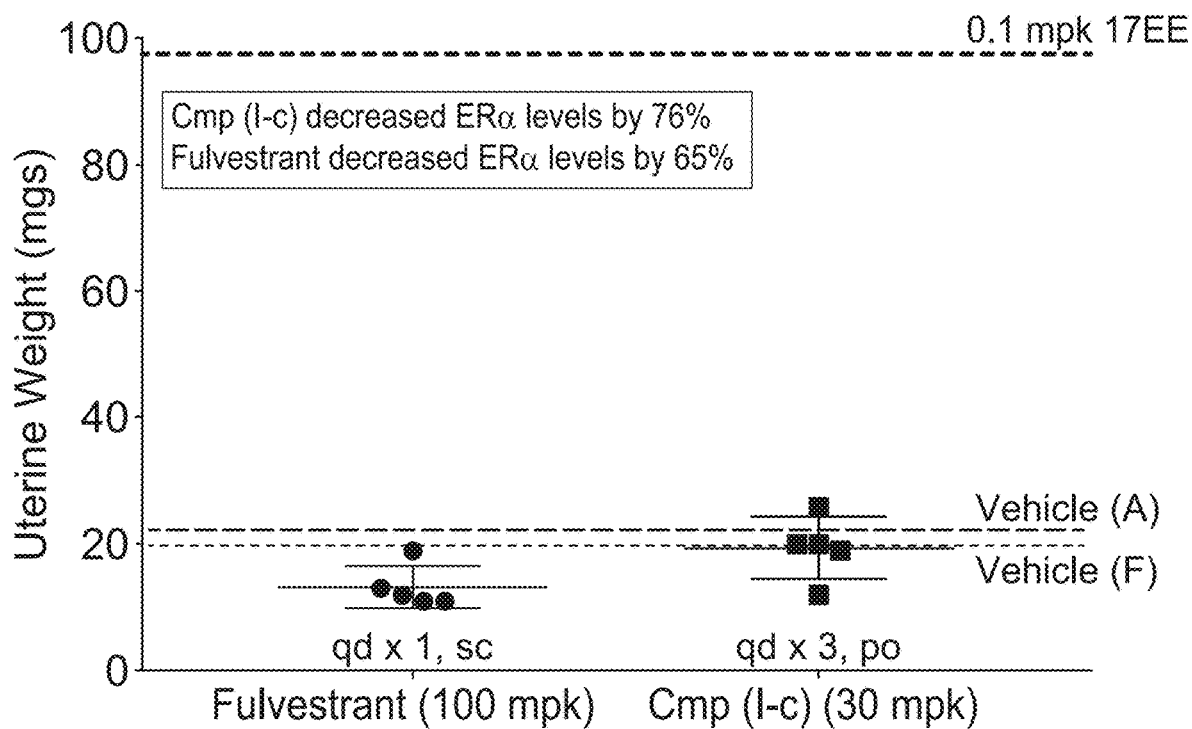
FIG. 17 is a graph showing the effect on uterine weight of fulvestrant (100 mg/kg once per day, subcutaneous administration) and Compound (I-c) (30 mg/kg once a day, oral administration) compared to vehicle.
Figure 18:
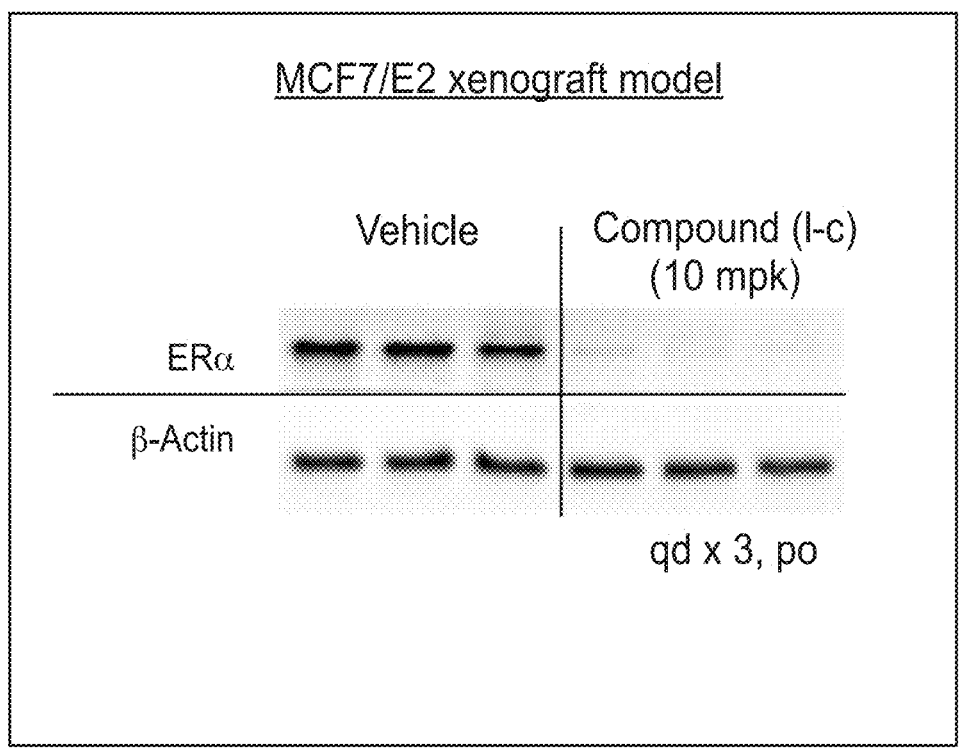
FIG. 18 is a Western Blot comparing the in vivo ERα degradation activity of Compound (I-c) (oral administration at 10 mg/kg for 3 days) to vehicle in a MCF7/E2 xenograft model.
Figure 22:
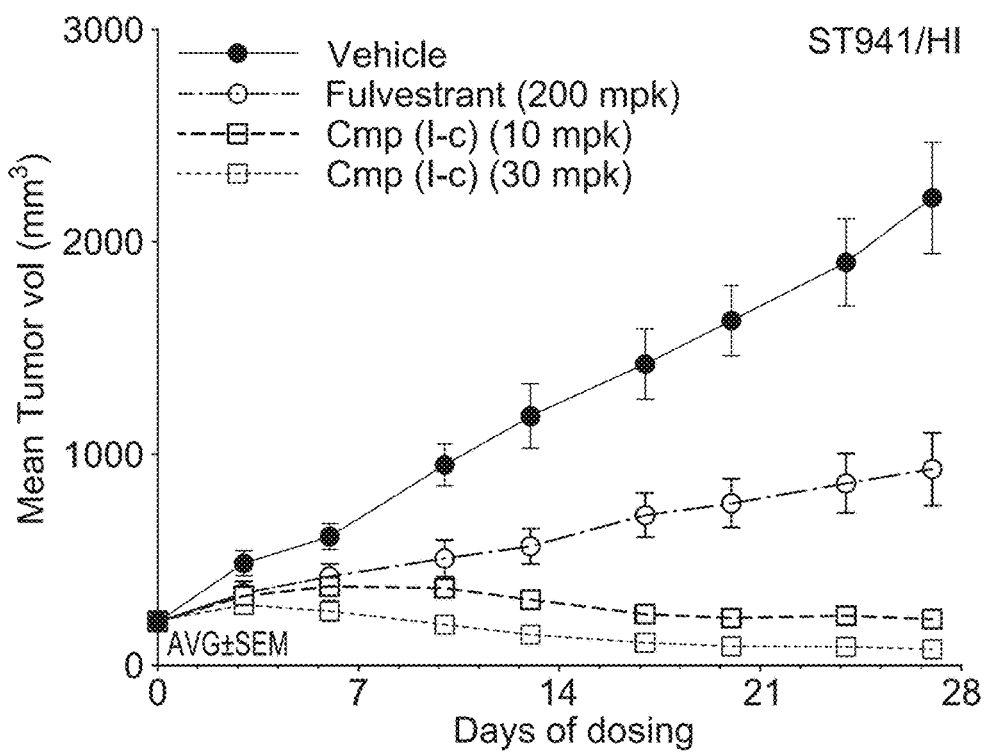
FIG. 22 shows the results of tumor growth inhibition (mean tumor volume (mm$^3$) vs. time) experiments in a ESR1 (Y537S) PDX model associated with administration of Compound (I-c) at an oral, once daily dose of 10 mg/kg or 30 mg/kg for 28 days, or fulvestrant (200 mg/kg, subcutaneous twice/week, for 2 weeks). At either the 10 mg/kg or 30 mg/kg dose, Compound (I-c) reduced tumor ERα levels in greater amounts compared to fulvestrant (79/88% vs. 63%) and resulted in an improved inhibition of tumor growth compared to fulvestrant (99/106% vs. 62%).

Compound (I-c) robustly degrades ER in ER-positive breast cancer cell lines with a half-maximal degradation concentration ($DC_{50}$) of ~1 nM (FIG. 13 and FIG. 14). ER degradation mediated by Compound (I-c) decreases the expression of classically-regulated ER-target genes MCF7 and T47D (FIG. 13 through FIG. 16) and inhibits cell proliferation of ER-dependent cell lines. Additionally, Compound (I-c) degrades clinically-relevant ESR1 variants Y537S and D538G (FIG. 15), and inhibits growth of cell lines expressing those variants. In an immature rat uterotrophic model, Compound (I-c) degrades rat uterine ER and demonstrates no agonist activity (FIG. 17). Daily, oral-administration of single agent Compound (I-c) (3, 10, and 30 mg/kg) leads to significant anti-tumor activity of estradiol-dependent MCF7 xenografts and concomitant tumor ER protein reductions of >90% at study termination (FIG. 1, FIG. 5, and FIG. 7). Moreover, when a CDK4/6 inhibitor is combined with Compound (I-c) in the MCF7 model, even more pronounced tumor growth inhibition is observed (131% TGI)(FIG. 8). Compound (I-c) inhibited growth by 65% in a tamoxifen-resistant MCF7 xenograft and when Compound (I-c) was combined with palbociclib resulted in even greater tumor growth inhibition (113% TGI) when compared to the single-agent arm of palbociclib (91% TGI) (Table 8 and FIG. 9). In the clinically relevant ESR1 Y537S mutant model, a hormone-independent patient-derived xenograft model, Compound (I-c) at 10 mg/kg completely inhibited growth and also significantly reduced mutant ER protein levels (FIG. 22). Taken together, the preclinical data of Compound (I-c) supports its continued development as an orally bioavailable ER protein degrader.

TABLE 10

Summary of In vivo Studies with Compound (I-c).

| | MCF7/estradiol | | Tamoxifen-resistant MCF7 | | ESR1 (Y537S) PDX | |
|---|---|---|---|---|---|---|
| | % TGI | % ERα ↓ | % TGI | % ERα ↓ | % TGI | % ERα ↓ |
| Compound (I-c) (3 mg/kg) | 85 | 95 | nd | nd | Nd | Nd |
| Compound (I-c) (10 mg/kg) | 94 | 97 | nd | nd | 99 | 79 |
| Compound (I-c) (30 mg/kg) | 105-124 | 94 | 65 | 73 | 106 | 88 |
| 200 mg/kg fulvestrant | 46 | None | nd | nd | 62 | 63 |
| Compound (I-c) (30 mg/kg) + Palbociclib (60 mg/kg) | 131 | 89 | 113 | 72 | Nd | Nd |
| 200 mg/kg fulvestrant + Palbociclib (60 mg/kg) | 108 | None | nd | nd | Nd | Nd | nd = not determined

Figure 19:
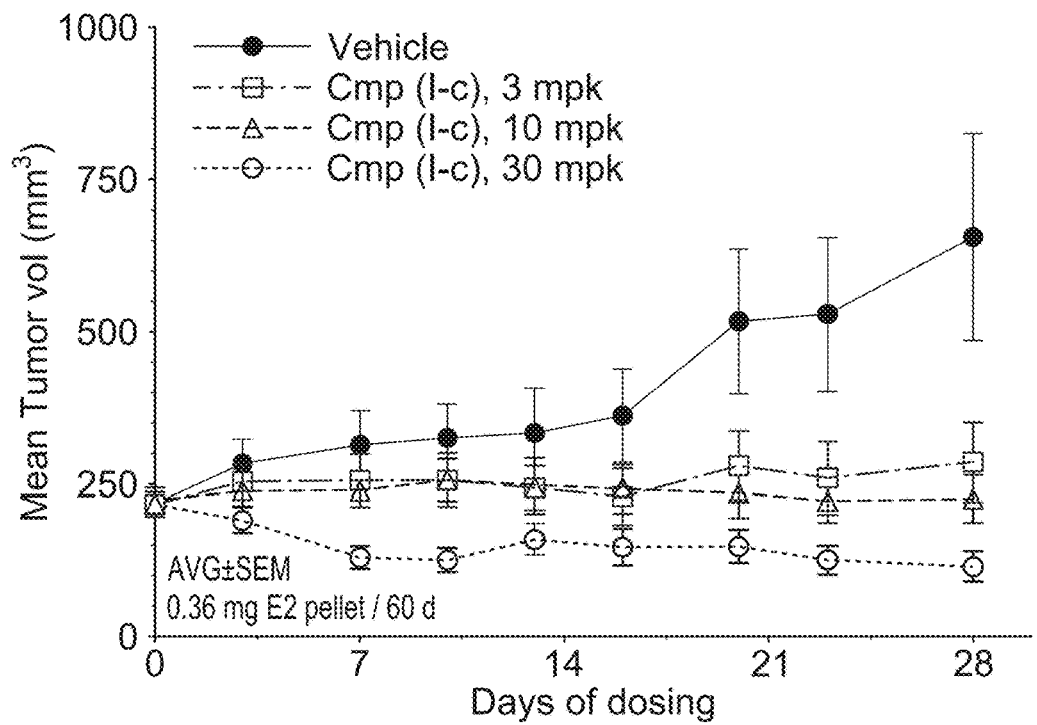
FIG. 19 shows the results of tumor growth inhibition experiments (mean tumor volume (mm$^3$) vs. time) associated with oral, once daily administration of Compound (I-c) at doses of 3 mg/kg, 10 mg/kg, and 30 mg/kg for 28 days compared to vehicle. At doses of 3 mg/kg, 10 mg/kg, and 30 mg/kg of Compound (I-c), tumor growth inhibition (TGI) of 85%, 98%, and 124%, respectively, was observed compared to a control group in a MCF7/estradiol xenograft model.
Figure 20:
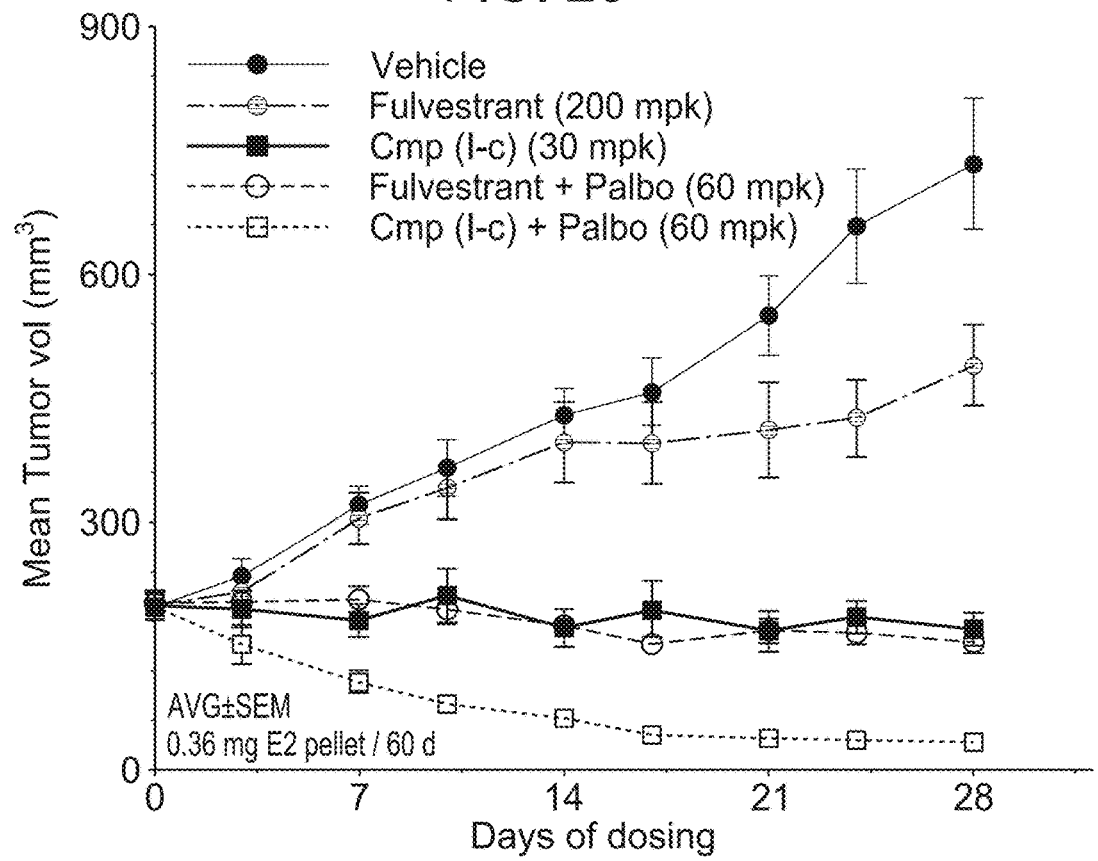
FIG. 20 shows the results of tumor growth inhibition (mean tumor volume (mm$^3$) vs. time) experiments in a MCF7/estradiol model associated with administration of Compound (I-c) at an oral, once daily dose of 30 mg/kg for 28 days, fulvestrant (200 mg/kg, subcutaneous twice/week for 2 weeks), Compound (I-c) (oral, once daily dose of 30 mg/kg for 28 days) plus palbociclib (oral, once daily dose of 60 mg/kg for 28 days), and fulvestrant (200 mg/kg, subcutaneous twice/week, for 2 weeks) plus palbociclib (oral, once daily dose of 60 mg/kg for 28 days) compared to vehicle. When compared to single-agent Compound (I-c) activity in this model (105% TGI), the combination of Compound (I-c) and palbociclib provided significant tumor regressions (131% TGI). In contrast, single-agent fulvestrant, which was dosed subcutaneously, resulted in only modest tumor growth inhibition (46% TGI), while the combination of fulvestrant and palbociclib resulted in improved inhibition of tumor growth (108% TGI) but not to the levels of that achieved with Compound (I-c) and palbociclib (131% TGI).
Figure 21:
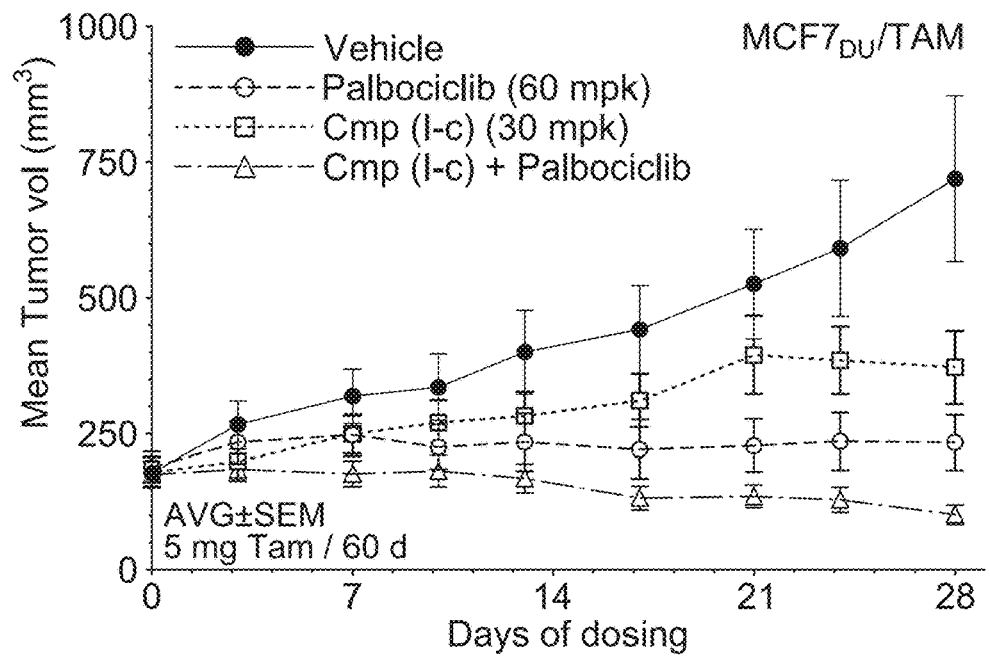
FIG. 21 shows the results of tumor growth inhibition (mean tumor volume (mm$^3$) vs. time) experiments in a tamoxifen-resistant MCF7 model associated with administration of Compound (I-c) at an oral, once daily dose of 30 mg/kg for 28 days, palbociclib (oral, once daily dose of 60 mg/kg for 28 days), and Compound (I-c) (oral, once daily dose of 30 mg/kg for 28 days) plus palbociclib (oral, once daily dose of 60 mg/kg for 28 days) compared to vehicle. While Compound (I-c) alone reduced tumor growth, the combination of Compound (I-c) and palbociclib resulted in an improved inhibition of tumor growth compared to Compound (I-c) alone (113% vs. 65%).

Oral administration of Compound (I-c) provides more robust tumor growth inhibition and ERα degradation compared to fulvestrant in an orthotopic MCF7/estradiol xenograft model (FIG. 19 and FIG. 20, Table 10). Combination of Compound (I-c) and palbociclib results in significant tumor regressions and overall superior antitumor activity when compared to fulvestrant and palbociclib combination (FIG. 20 through FIG. 22 and Table 10).

Compound (I-c) inhibits growth of tamoxifen-resistant and ESR1 (Y537S) tumors while also reducing tumor ERα levels (FIG. 22, Table 10).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The methods of the disclosure have been described herein by reference to certain preferred embodiments. However, as particular variations thereon will become apparent to those skilled in the art, based on the disclosure set forth herein, the disclosure is not to be considered as limited thereto.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise.

It is to be understood that at least some of the descriptions of the disclosure have been simplified to focus on elements that are relevant for a clear understanding of the disclosure, while eliminating, for purposes of clarity, other elements that those of ordinary skill in the art will appreciate may also comprise a portion of the disclosure. However, because such elements are well known in the art, and because they do not necessarily facilitate a better understanding of the disclosure, a description of such elements is not provided herein.

Further, to the extent that a method does not rely on the particular order of steps set forth herein, the particular order of the steps recited in a claim should not be construed as a limitation on that claim.

All patents, patent applications, references and publications cited herein are fully and completely incorporated by reference as if set forth in their entirety. Such documents are not admitted to be prior art to the present disclosure.

What is claimed is:

1. A method of treating metastatic breast cancer in a subject, comprising administering to the subject an effective amount of palbociclib and an effective amount of a compound of Formula (I-c):

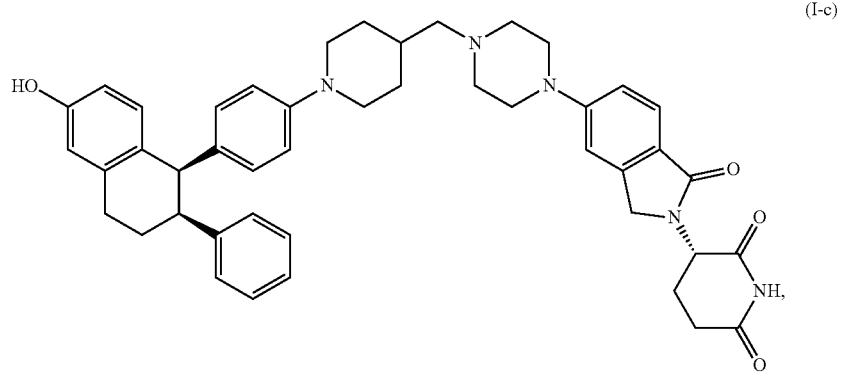 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(I-c)

or a pharmaceutically acceptable salt thereof, wherein the effective amount of the compound of Formula (I-c), or a pharmaceutically acceptable salt thereof, is about 10 mg to about 1000 mg.

2. The method of claim 1, wherein the metastatic breast cancer is ER+, HER2−.

3. The method of claim 1, wherein the compound of Formula (I-c), or a pharmaceutically acceptable salt thereof, is administered orally to the subject.

4. The method of claim 1, wherein the effective amount of the compound of Formula (I-c), or a pharmaceutically acceptable salt thereof, is administered to the subject once a day, twice a day, three times a day, or four times a day.

5. The method of claim 4, wherein the effective amount of the compound of Formula (I-c), or a pharmaceutically acceptable salt thereof, is administered to the subject once a day.

6. The method of claim 1, wherein the effective amount of the compound of Formula (I-c), or a pharmaceutically acceptable salt thereof, is administered to the subject all at once or is administered in two, three, or four portions.

7. The method of claim 1, wherein the effective amount of the compound of Formula (I-c), or a pharmaceutically acceptable salt thereof, is about 10 mg, about 15 mg, about 20 mg, about 25 mg, or about 30 mg.

8. The method of claim 1, wherein the effective amount of the compound of Formula (I-c), or a pharmaceutically acceptable salt thereof, is about 20 mg to about 750 mg.

9. The method of claim 8, wherein the effective amount of the compound of Formula (I-c), or a pharmaceutically acceptable salt thereof, is about 30 mg to about 500 mg.

10. The method of claim 9, wherein the effective amount of the compound of Formula (I-c), or a pharmaceutically acceptable salt thereof, is about 30 mg to about 120 mg.

11. The method of claim 1, wherein the effective amount of the compound of Formula (I-c), or a pharmaceutically acceptable salt thereof, results in a mean day 15 $AUC_{TAU}$ of greater than about 3,500 ng*hr/mL, greater than about 3,600 ng*hr/mL, greater than about 3,700 ng*hr/mL, greater than about 3,800 ng*hr/mL, greater than about 3,900 ng*hr/mL, greater than about 4,000 ng*hr/mL, greater than about 4,100 ng*hr/mL, greater than about 4,200 ng*hr/mL, greater than about 4,300 ng*hr/mL, greater than about 4,400 ng*hr/mL, greater than about 4,500 ng*hr/mL, greater than about 4,600 ng*hr/mL, greater than about 4,700 ng*hr/mL, greater than about 4,800 ng*hr/mL, greater than about 4,900 ng*hr/mL, or greater than about 5,000 ng*hr/mL.

12. The method of claim 11, wherein the effective amount of the compound of Formula (I-c), or a pharmaceutically acceptable salt thereof, results in a mean day 15 $AUC_{TAU}$ of greater than about 4,000 ng*hr/mL and less than about 4,500 ng*hr/mL.

13. The method of claim 1, wherein the effective amount of the compound of Formula (I-c), or a pharmaceutically acceptable salt thereof, results in a mean day 15 $C_{max}$ of greater than about 200 ng/mL, greater than about 205 ng/mL, greater than about 210 ng/mL, greater than about 215 ng/mL, greater than about 220 ng/mL, greater than about 225 ng/mL, greater than about 230 ng/mL, greater than about 235 ng/mL, greater than about 240 ng/mL, greater than about 245 ng/mL, or greater than about 250 ng/mL.

14. The method of claim 13, wherein the effective amount of the compound of Formula (I-c), or a pharmaceutically acceptable salt thereof, results in a mean day 15 $C_{max}$ of greater than about 215 ng/mL and less than about 235 ng/mL.

15. The method of claim 1, wherein the effective amount of palbociclib is administered to the subject once a day.

16. The method of claim 1, wherein the effective amount of palbociclib is 60 mg, 75 mg, 100 mg, or 125 mg.

17. The method of claim 1, wherein the palbociclib is administered once daily for up to 21 consecutive days, followed by up to 7 consecutive days off treatment, wherein the cycle of treatment with palbociclib followed by off treatment is repeated one, two, three, four, five, or more times.

18. The method of claim 1, wherein the compound of Formula (I-c), or a pharmaceutically acceptable salt thereof, is administered once daily for up to 21 consecutive days, followed by up to 7 consecutive days off treatment, wherein the cycle of treatment with the compound of Formula (I-c), or a pharmaceutically acceptable salt thereof, followed by off treatment is repeated one, two, three, four, five, or more times.

19. A method of treating metastatic breast cancer in a subject, comprising oral administration of an effective amount of palbociclib and an effective amount of a compound of Formula (I-c),

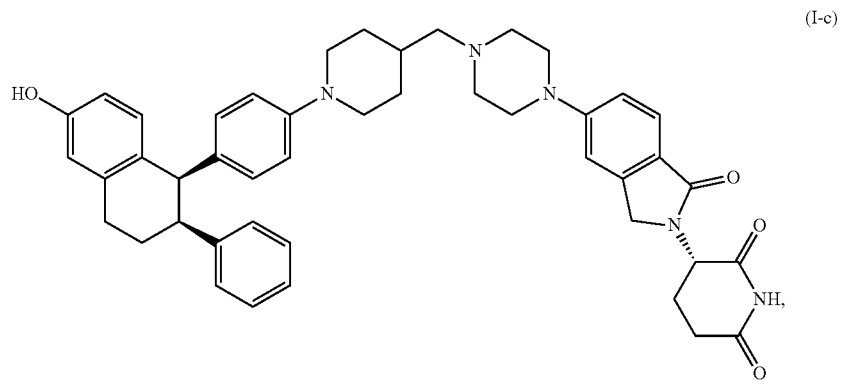 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(I-c)

or a pharmaceutically acceptable salt thereof, wherein the effective amount of the compound of Formula (I-c), or a pharmaceutically acceptable salt thereof, is about 30 mg to about 1000 mg.

20. The method of claim 19, wherein the effective amount of the compound of Formula (I-c), or a pharmaceutically acceptable salt thereof, is administered to the subject all at once or is administered in two, three, or four portions.

21. The method of claim 19, wherein the compound of Formula (I-c), or a pharmaceutically acceptable salt thereof, is formulated as a tablet.

22. The method of claim 19, wherein the effective amount of palbociclib is administered to the subject once a day.

23. The method of claim 19, wherein the effective amount of palbociclib is 60 mg, 75 mg, 100 mg, or 125 mg.

24. The method of claim 19, wherein the palbociclib is administered once daily for up to 21 consecutive days, followed by up to 7 consecutive days off treatment, wherein the cycle of treatment with palbociclib followed by off treatment is repeated one, two, three, four, five, or more times.

25. The method of claim 19, wherein the compound of Formula (I-c), or a pharmaceutically acceptable salt thereof, is administered once daily for up to 21 consecutive days, followed by up to 7 consecutive days off treatment, wherein the cycle of treatment with the compound followed by off treatment is repeated one, two, three, four, five, or more times.

26. The method of claim 19, wherein the administration of palbociclib occurs before the administration of the compound of Formula (I-c), or a pharmaceutically acceptable salt thereof.

27. The method of claim 26, wherein the administration of palbociclib occurs at least 30 minutes before the administration of the compound of Formula (I-c), or a pharmaceutically acceptable salt thereof.

28. The method of claim 19, wherein the administration of palbociclib occurs after the administration of the compound of Formula (I-c), or a pharmaceutically acceptable salt thereof.

29. The method of claim 28, wherein the administration of palbociclib occurs at least 30 minutes after the administration of the compound of Formula (I-c), or a pharmaceutically acceptable salt thereof.

30. The method of claim 15, wherein the effective amount of palbociclib is 60 mg, 75 mg, 100 mg, or 125 mg.

31. A method of treating metastatic breast cancer in a subject, comprising administering to the subject an effective amount of palbociclib and an effective amount of a compound of Formula (I-c):

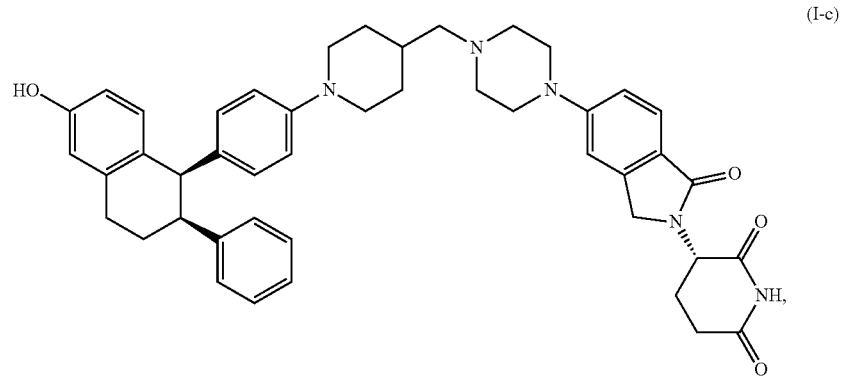 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

(I-c)

wherein the effective amount of the compound of Formula (I-c) is about 10 mg to about 1000 mg.

* * * * *